United States Patent
Anchel

(10) Patent No.: US 11,279,748 B2
(45) Date of Patent: Mar. 22, 2022

(54) RECOMBINANT ANIMAL-FREE FOOD COMPOSITIONS AND METHODS OF MAKING THEM

(71) Applicant: Clara Foods Co., South San Francisco, CA (US)

(72) Inventor: David Anchel, San Francisco, CA (US)

(73) Assignee: CLARA FOODS CO., South San Francisco, CA (US)

(*) Notice: Subject to any disclaimer, the term of this patent is extended or adjusted under 35 U.S.C. 154(b) by 0 days.

(21) Appl. No.: 16/701,022

(22) Filed: Dec. 2, 2019

(65) Prior Publication Data

US 2020/0138066 A1 May 7, 2020

Related U.S. Application Data

(63) Continuation of application No. 15/522,986, filed as application No. PCT/US2015/060147 on Nov. 11, 2015.

(60) Provisional application No. 62/078,385, filed on Nov. 11, 2014.

(51) Int. Cl.
| | |
|---|---|
| *A23L 15/00* | (2016.01) |
| *C07K 14/77* | (2006.01) |
| *A23J 3/04* | (2006.01) |
| *A23J 3/20* | (2006.01) |
| *A23J 1/08* | (2006.01) |
| *A23L 33/195* | (2016.01) |
| *C07K 14/79* | (2006.01) |
| *C07K 14/465* | (2006.01) |
| *C12P 21/02* | (2006.01) |
| *A23J 1/18* | (2006.01) |
| *A21D 2/26* | (2006.01) |
| *A23J 1/09* | (2006.01) |
| *C12N 15/81* | (2006.01) |

(52) U.S. Cl.
CPC .............. *C07K 14/77* (2013.01); *A21D 2/262* (2013.01); *A23J 1/08* (2013.01); *A23J 1/09* (2013.01); *A23J 1/18* (2013.01); *A23J 3/04* (2013.01); *A23J 3/20* (2013.01); *A23L 15/35* (2016.08); *A23L 33/195* (2016.08); *C07K 14/465* (2013.01); *C07K 14/79* (2013.01); *C12N 15/815* (2013.01); *C12P 21/02* (2013.01); *A23V 2002/00* (2013.01)

(58) Field of Classification Search
CPC ...... C07K 14/77; C07K 14/465; C07K 14/79; A23L 33/195; A23L 15/35; A21D 2/262; A23J 1/08; A23J 1/09; A23J 1/18; A23J 3/04; A23J 3/20; C12N 15/815; C12P 21/02; A23V 2002/00
See application file for complete search history.

(56) References Cited

U.S. PATENT DOCUMENTS

| | | | |
|---|---|---|---|
| 897,192 A | 8/1908 | Joseph | |
| 3,251,697 A * | 5/1966 | Lineweaver | A23B 5/18 426/322 |
| 3,806,608 A | 4/1974 | Perret | |
| 4,355,022 A | 10/1982 | Rabussay | |
| 4,430,428 A | 2/1984 | Fraser et al. | |
| 4,675,201 A | 6/1987 | Lee et al. | |
| 4,810,508 A | 3/1989 | Dell'Acqua et al. | |
| 4,880,643 A | 11/1989 | Bamforth et al. | |
| 5,019,411 A | 5/1991 | Johnson et al. | |
| 5,149,521 A | 9/1992 | Hirose et al. | |
| 5,283,236 A | 2/1994 | Chiou | |
| 5,336,609 A | 8/1994 | Oberto et al. | |
| 5,643,792 A | 7/1997 | Okabayashi et al. | |
| 5,849,477 A | 12/1998 | O'Malley et al. | |
| 6,204,012 B1 | 3/2001 | Hellmuth et al. | |
| 6,316,034 B1 | 11/2001 | Daeschel et al. | |
| 6,465,254 B1 | 10/2002 | Saito et al. | |
| 6,495,344 B1 | 12/2002 | Carr et al. | |
| 6,645,739 B2 | 11/2003 | Clark | |
| 6,699,691 B2 | 3/2004 | Inan et al. | |
| 6,730,499 B1 | 5/2004 | Cregg | |
| 6,803,225 B2 | 10/2004 | Contreras et al. | |
| 6,875,588 B2 | 4/2005 | Harvey et al. | |
| 6,933,146 B2 | 8/2005 | Helliwell et al. | |
| 6,994,876 B1 | 2/2006 | Sher et al. | |
| 7,029,872 B2 | 4/2006 | Gerngross | |
| 7,037,895 B2 | 5/2006 | Assaly et al. | |
| 7,078,488 B2 | 7/2006 | Jiang et al. | |
| 7,205,018 B2 | 4/2007 | Sherwood et al. | |
| 7,252,933 B2 | 8/2007 | Contreras et al. | |
| 7,294,507 B2 | 11/2007 | Harvey et al. | |
| 7,326,681 B2 | 2/2008 | Gerngross | |
| 7,335,761 B2 | 2/2008 | Harvey et al. | |
| 7,345,150 B2 | 3/2008 | Assaly et al. | |
| 7,348,312 B2 | 3/2008 | Assaly et al. | |
| 7,507,573 B2 | 3/2009 | Contreras et al. | |
| 7,595,186 B2 | 9/2009 | Gerdes et al. | |
| 7,598,055 B2 | 10/2009 | Bobrowicz et al. | |
| 7,629,163 B2 | 12/2009 | Gerngross | |

(Continued)

FOREIGN PATENT DOCUMENTS

| | | | | |
|---|---|---|---|---|
| AU | 2005264767 A1 * | 1/2006 | | A61K 38/38 |
| CA | 2574558 A1 | 1/2006 | | |
| CN | 1214729 C | 8/2005 | | |
| CN | 101022737 A | 8/2007 | | |
| CN | 101623111 A | 1/2010 | | |

(Continued)

OTHER PUBLICATIONS

Babu Dissertation, Jan. 2006. (Year: 2006).*

(Continued)

*Primary Examiner* — Catherine S Hibbert
(74) *Attorney, Agent, or Firm* — Wilson Sonsini Goodrich & Rosati

(57) ABSTRACT

Provided herein are recombinant animal-free food compositions comprising egg-white proteins such as ovalbumin, ovotransferrin and lysozyme and methods of making such food compositions.

18 Claims, 18 Drawing Sheets

Specification includes a Sequence Listing.

(56) References Cited

U.S. PATENT DOCUMENTS

| | | |
|---|---|---|
| 7,745,200 B2 | 6/2010 | Cregg |
| 7,794,770 B2 | 9/2010 | Sherwood et al. |
| 7,799,363 B2 | 9/2010 | Sherwood et al. |
| 7,842,326 B2 | 11/2010 | Sherwood et al. |
| 7,884,068 B2 | 2/2011 | Assaly et al. |
| 7,897,192 B2 | 3/2011 | Sherwood et al. |
| 7,906,160 B2 | 3/2011 | Sherwood et al. |
| 7,923,430 B2 | 4/2011 | Gerngross |
| 7,923,431 B2 | 4/2011 | Wolff |
| 7,972,809 B2 | 7/2011 | Kobayashi et al. |
| 8,058,053 B2 | 11/2011 | Contreras et al. |
| 8,067,551 B2 | 11/2011 | Gerngross et al. |
| 8,075,919 B2 | 12/2011 | Brown et al. |
| 8,211,691 B2 | 7/2012 | Gerngross |
| 8,222,032 B2 | 7/2012 | Parker et al. |
| 8,227,207 B2 | 7/2012 | Miguel Castro et al. |
| 8,227,436 B2 | 7/2012 | McMillan et al. |
| 8,354,268 B2 | 1/2013 | Contreras et al. |
| 8,445,227 B2 | 5/2013 | Bobrowicz et al. |
| 8,546,136 B2 | 10/2013 | Serber et al. |
| 8,642,017 B2 | 2/2014 | Wagstaff |
| 8,663,971 B2 | 3/2014 | Contreras et al. |
| 8,697,394 B2 | 4/2014 | Bobrowicz et al. |
| 8,753,698 B2* | 6/2014 | Van Amerongen .... A61K 38/47 426/63 |
| 8,778,659 B2 | 7/2014 | Govindappa et al. |
| 8,809,259 B2 | 8/2014 | Berry et al. |
| 8,815,580 B2 | 8/2014 | Callewaert et al. |
| 8,822,412 B2 | 9/2014 | Berry et al. |
| 8,877,462 B2 | 11/2014 | Gerngross et al. |
| 8,883,445 B2 | 11/2014 | Contreras et al. |
| 8,883,483 B2 | 11/2014 | Gerngross et al. |
| 8,932,825 B2 | 1/2015 | Wildt et al. |
| 8,986,773 B2 | 3/2015 | Beckhoven Van et al. |
| 9,012,175 B2 | 4/2015 | Hartner et al. |
| 9,206,454 B2 | 12/2015 | Weis et al. |
| 9,220,292 B2 | 12/2015 | Jenkins |
| 9,279,129 B2 | 3/2016 | Hartner et al. |
| 9,359,628 B2 | 6/2016 | Contreras et al. |
| 9,598,474 B2 | 3/2017 | Berry et al. |
| 9,605,040 B2 | 3/2017 | Von Maltzahn et al. |
| 9,611,298 B2 | 4/2017 | Berry et al. |
| 9,617,550 B2 | 4/2017 | Gehlsen et al. |
| 9,689,016 B2 | 6/2017 | Marcel et al. |
| 9,700,071 B2 | 7/2017 | Silver et al. |
| 9,757,328 B2 | 9/2017 | Ferrari et al. |
| 2002/0098198 A1 | 7/2002 | Watts et al. |
| 2003/0069395 A1 | 4/2003 | Sato et al. |
| 2004/0142906 A1 | 7/2004 | Wang |
| 2004/0231010 A1 | 11/2004 | Murray et al. |
| 2005/0026264 A1 | 2/2005 | Jiang et al. |
| 2005/0090001 A1* | 4/2005 | Parker .................. C12N 5/0682 435/349 |
| 2005/0266140 A1 | 12/2005 | Kastenmayer et al. |
| 2006/0228769 A1 | 10/2006 | Yano et al. |
| 2006/0280804 A1 | 12/2006 | Castro et al. |
| 2006/0280840 A1 | 12/2006 | Robertson |
| 2007/0065555 A1 | 3/2007 | Soane et al. |
| 2007/0141139 A1 | 6/2007 | Vandenberg |
| 2007/0231448 A1 | 10/2007 | Takahashi |
| 2008/0166447 A1 | 7/2008 | Strohbehn et al. |
| 2008/0214485 A1 | 9/2008 | McMillan et al. |
| 2008/0260913 A1 | 10/2008 | Orcutt et al. |
| 2009/0029005 A1 | 1/2009 | Van et al. |
| 2009/0042249 A1 | 2/2009 | Lubys et al. |
| 2009/0178147 A1* | 7/2009 | Harvey ................ C12N 9/1051 800/4 |
| 2009/0191157 A1 | 7/2009 | Albrecht et al. |
| 2009/0263863 A1 | 10/2009 | Contreras et al. |
| 2009/0290005 A1* | 11/2009 | Wanibe ................ B41J 2/17566 347/86 |
| 2011/0020811 A1 | 1/2011 | Crowell |
| 2012/0093994 A1 | 4/2012 | Hsieh et al. |
| 2013/0084361 A1* | 4/2013 | Shepheard ........... A23L 29/262 426/62 |
| 2014/0170268 A1 | 6/2014 | Graeber et al. |
| 2014/0345004 A1 | 11/2014 | Callewaert et al. |
| 2014/0356507 A1 | 12/2014 | Tetrick et al. |
| 2015/0152427 A1 | 6/2015 | Wildt et al. |
| 2015/0191607 A1 | 7/2015 | McDaniel |
| 2015/0284693 A1 | 10/2015 | Nagaoka |
| 2015/0305368 A1 | 10/2015 | Dake et al. |
| 2015/0307562 A1 | 10/2015 | Basu et al. |
| 2016/0024511 A1 | 1/2016 | Tolstorukov et al. |
| 2016/0038428 A1 | 2/2016 | Harel et al. |
| 2016/0039911 A1 | 2/2016 | Lesnicki et al. |
| 2016/0051593 A1 | 2/2016 | Raff |
| 2016/0068880 A1 | 3/2016 | Gerngross |
| 2016/0083722 A1 | 3/2016 | Young et al. |
| 2016/0106137 A1 | 4/2016 | Jenkins |
| 2016/0183567 A1 | 6/2016 | Choi et al. |
| 2017/0029827 A1 | 2/2017 | Gasser et al. |
| 2017/0037418 A1 | 2/2017 | Mattanovich et al. |
| 2017/0159094 A1 | 6/2017 | Natunen et al. |
| 2018/0084814 A1 | 3/2018 | Challakere et al. |
| 2018/0355020 A1 | 12/2018 | Anchel |

FOREIGN PATENT DOCUMENTS

| | | |
|---|---|---|
| CN | 101496575 B | 10/2010 |
| CN | 101496579 B | 10/2010 |
| CN | 102076221 A | 5/2011 |
| CN | 102429307 A | 5/2012 |
| CN | 102308940 B | 8/2012 |
| CN | 102978268 A | 3/2013 |
| CN | 102630865 B | 5/2013 |
| CN | 102008076 B | 7/2013 |
| CN | 103445263 A | 12/2013 |
| CN | 104172168 A | 12/2014 |
| CN | 104172186 A | 12/2014 |
| CN | 104187634 A | 12/2014 |
| CN | 104187666 A | 12/2014 |
| CN | 104256633 A | 1/2015 |
| CN | 104256648 A | 1/2015 |
| CN | 104431285 A | 3/2015 |
| CN | 104694560 A | 6/2015 |
| CN | 104738624 A | 7/2015 |
| CN | 104824674 A | 8/2015 |
| CN | 104855977 A | 8/2015 |
| CN | 104957356 A | 10/2015 |
| CN | 104961823 A | 10/2015 |
| CN | 105012941 A | 11/2015 |
| CN | 105039189 A | 11/2015 |
| CN | 103182074 B | 3/2016 |
| CN | 104146248 B | 6/2016 |
| CN | 105876440 A | 8/2016 |
| CN | 106173829 A | 12/2016 |
| CN | 106259946 A | 1/2017 |
| EP | 0265884 B1 | 12/1992 |
| EP | 1156719 B1 | 5/2003 |
| EP | 1278511 B1 | 8/2004 |
| EP | 1119264 B1 | 3/2005 |
| EP | 1297172 B1 | 11/2005 |
| EP | 1655308 A1 | 5/2006 |
| EP | 1211310 B1 | 12/2006 |
| EP | 1294910 B1 | 11/2008 |
| EP | 1522590 B1 | 8/2009 |
| EP | 2376349 B1 | 10/2012 |
| EP | 2001312 B1 | 5/2014 |
| EP | 2339013 B1 | 7/2014 |
| EP | 2271222 B1 | 2/2015 |
| EP | 2862933 A2 | 4/2015 |
| EP | 2964775 A1 | 1/2016 |
| EP | 3083966 A1 | 10/2016 |
| EP | 1467615 B2 | 3/2017 |
| ES | 2188336 A1 | 6/2003 |
| ES | 2329316 B1 | 10/2010 |
| FR | 2458585 A1 | 1/1981 |
| GB | 1211361 A | 11/1970 |
| GB | 2033905 B | 10/1982 |
| JP | 2007259805 A | 10/2007 |
| JP | 2008507270 A | 3/2008 |
| JP | 5048487 B2 | 10/2012 |
| JP | 2014171424 A | 9/2014 |

(56) References Cited

FOREIGN PATENT DOCUMENTS

| WO | WO-0200856 A2 | 1/2002 | |
|----|----|----|----|
| WO | WO-03102187 A1 | 12/2003 | |
| WO | WO-2004065593 A1 | 8/2004 | |
| WO | WO-2007106731 A2 | 9/2007 | |
| WO | WO-2012129036 A2 | 9/2012 | |
| WO | WO-2013148330 A1 * | 10/2013 | ............. A23L 33/18 |
| WO | WO-2015048339 A2 | 4/2015 | |
| WO | WO-2015048342 A2 | 4/2015 | |
| WO | WO-2016014900 A2 | 1/2016 | |
| WO | WO-2016077457 A1 | 5/2016 | |
| WO | WO-2016081645 A1 | 5/2016 | |
| WO | WO-2016160655 A1 | 10/2016 | |
| WO | WO-2016183056 A1 | 11/2016 | |
| WO | WO-2020041483 A1 | 2/2020 | |

OTHER PUBLICATIONS

Rupa & Mine BBRC Apr. 14, 2006: vol. 342 pp. 710-717) (Year: 2006).*

Ramat Thesis entitled: Protein Purification Using Expanded Bed Chromatography 2004 (Year: 2004).*

Masuda et al (Protein Expression and Purification, 2004, vol. 39, pp. 35-42. (Year: 2004).*

Abeyrathne et al (Poultry Science 2013 vol. 92: pp. 3292-3299). (Year: 2013).*

Lechevalier (Food Chemistry 2005 vol 92: pp. 79-87). (Year: 2005).*

Ambort et al., Perspectives on Mucus Properties and Formation—Lessons from the Biochemical World, Cold Spring Harb Perspect Med; 2:a014159 (9 pages) (2012).

Callewaert et al., Use of HDEL-tagged Trichoderma reesei mannosyl oligosaccharide 1,2-α-D-mannosidase for N-glycan engineering in Pichia pastoris, FEBS Letters, 503:173-178 (2001).

EP15858729.5 Extended European Report dated Aug. 13, 2018.

EP15858729.5 Partial Supplementary European Search Report dated May 11, 2018.

International Search Report and Written Opinion dated Feb. 1, 2016 for International Application No. PCT/US2015/060147.

Ito et al., Structural Characteristics of Hen Egg Ovalbumin Expressed in Yeast *Pichia pastoris*, Biosci. Biotechnol. Biochem., 69(4): 755-761 (2005).

Kato et al. Chicken ovomucoid: determination of its amino acid sequence, determination of the trypsin reactive site, and preparation of all three of its domains. Biochemistry 26(1):193-201 (Jan. 13, 1987).

Krainer et al. Biotechnological advances towards an enhanced peroxidase production in Pichia pastoris. Journal of Biotechnology 233:181-189 (2016).

Mainwaring et al. Effect of pH on hen egg white lysozyme production and evolution of a recombinant strain of *Aspergillus niger*. Journal of Biotechnology 75(1):1-10 (Sep. 24, 1999). DOI: 10.1016/S0168-1656(99)00123-6.

Masuda et al. High yield secretion of the sweet-tasting protein lysozyme from the yeast *Pichia pastoris*. Protein Expression and Purification 39:35-42 (Nov. 2, 2004).

Mine et al. Reduction of antigenicity and allergenicity of genetically modified egg white allergen, ovomucoid third domain. Biochemical and Biophysical Research Communications 302:133-137 (2003).

Mizutani et al., Structural and Functional Characterization of Ovotransferrin Produced by Pichia pastoris, Biosci. Biotechnol. Biochem., 68(2): 376-383 (2004).

Nilsson et al., Intestinal MUC2 mucin supramolecular topology by packing and release resting on D3 domain assembly, J Mol Biol., 426(14): 2567-2579 (2014).

Partow et al. Characterization of different promoters for designing a new expression vector in *Saccharomyces cerevisiae*. Yeast 27:955-964 (2010). Published online Jul. 12, 2010. DOI: 10.1002/yea.1806.

Rajamanickam et al. A novel bi-directional promoter system allows tunable recombinant protein production in Pichia pastoris. Microb Cell Fact 16:152 (2017). 7 pages. DOI 10.1186/s12934-017-0768-8.

Rupa et al. Engineered recombinant ovomucoid third domain can modulate allergenic response in Balb/c mice model. Biochemical and Biophysical Research Communications 342:710-717 (2006).

Rupa et al. Genetically glycosylated ovomucoid third domain can modulate Immunoglobin E antibody production and cytokine response in BALB/c mice. Clinical and Experimental Allergy 37:918-928 (2007).

Rupa et al. Structural and immunological characterization of recombinant ovomucoid expressed in *Escherichia coli*. Biotechnology Letters 25:427-433 (2003).

Score report to Mcmillan et al per instant SEQ ID No. 1 (U.S. Pat. No. 8,227,436 issued Jul. 24, 2012 & published as 2008/0214485) (Year: 2012).

Score result for SEQ ID No. 3 for Berry et al (WO2015048339 & Silver et al WO2015048342 published Apr. 2, 2015) (Year: 2015).

Score result for SEQ ID No. 9 for Koentgen (WO2003102187-A1 published Dec. 11, 2003) (Year: 2003).

Wang et al., Proteomic analysis of fertilized egg white during early incubation, EuPA Open Proteomics, 2: 38-59 (2014).

Zocchi et al. Expression and purification of a recombinant avidin with a lowered isoelectric point in Pichia pastoris. Protein Expression and Purification 32:167-174 (2003).

Arntfield et al. Characteristics of heat-induced networks for mixtures of ovalbumin and lysozyme. J Agric. Food Chem 41:2291-2295 (1993).

Buell et al. Isolation of recombinant plasmids bearing cDNA to hen ovomucoid and lysozyme mRNAs. J Biol Chem 254(18): 9277-9283 (Sep. 25, 1979).

Catterall et al. Primary sequence of ovomucoid messenger RNA as determined from cloned complementary DNA. J Cell Biol 87(2 Pt 1):480-7 (Nov. 1980).

Digan et al. Continuous Production of a Novel Lysozyme via Secretion from the Yeast, *Pichia pastoris*.Bio/Technology 7:160-164(1989).

Fraser et al. Chicken ovalbumin is synthesized and secreted by *Escherichia coli*. Proc Natl Acad Sci U S A. 75(12): 5936-5940 (Dec. 1978).

Hughey et al. Antimicrobial activity of lysozyme against bacteria involved in food spoilage and food-borne disease. Appl Environ Microbiol 53(9):2165-70 (Sep. 1987).

Hynes et al. mRNA complexity and egg white protein mRNA content in mature and hormone-withdrawn oviduct. Cell 11:923-932 (Aug. 1977).

Ito et al. Importance of N-glycosylation positioning for secretion and folding of ovalbumin,Biochemical and Biophysical Research Communications 361(3):725-731 (2007). Available online Jul. 24, 2007.

Johnson et al. Gelation Properties of Albumen Proteins, Singly and in Combination. Poultry Science 60:2071-2083 (1981).

Lai et al. Molecular structure and flanking nucleotide sequences of the natural chicken ovomucoid gene. Cell 18:829-842 (1979).

Lindenmaier et al. Isolation and characterization of the chicken ovomucoid gene. Nucleic Acids Res 7(5):1221-32 (Nov. 10, 1979).

Liu et al. Improved antioxidant activity and physicochemical properties of curcumin by adding ovalbumin and its structural characterization. Food Hydrocolloids 72:304-311 (2017). Available online Jun. 9, 2017.

Mercereau-Puijalon et al. Synthesis of a chicken ovalbumin-like protein in the yeast *Saccharomyces cerevisiae*. Gene 11:163-167 (1980).

Palmieri et al. [Topical treatment of some dystrophic and inflammatory lesions of the skin and soft tissues.] Archivio per le Scienze Mediche, Oct.-Dec. 1977, 134(4):481-485.

Proctor et al. The chemistry of lysozyme and its use as a food preservative and a pharmaceutical. Crit Rev Food Sci Nutr 26(4):359-95 (1988).

U.S. Appl. No. 15/522,986 Office Action dated Aug. 8, 2019.

U.S. Appl. No. 15/522,986 Office Action dated Jan. 25, 2019.

(56) References Cited

OTHER PUBLICATIONS

Xiong et al. Effects of site-specific phosphorylation on the mechanical properties of ovalbumin-based hydrogels. International Journal of Biological Macromolecules 102:1286-1296 (2017). Available online May 8, 2017.

Alleoni et al. Albumen foam stability and s-ovalbumin contents in eggs coated with whey protein concentrate. Brazilian Journal of Poultry Science, vol. 6, No. 2, pp. 105-110 (Apr.-Jun. 2004).

Anumula et al., A comprehensive procedure for preparation of partially methylated alditol acetates from glycoprotein carbohydrates, Anal Biochem., 203(1): 101-108 (1992).

AOAC Official Method 925.09. Solids (Total) and Moisture in Flour, Vacuum Oven Method. Final Action. JAOAC 8, 665(1925); 9, 39, 88(1926); 34, 278(1951). In Official Methods of Analysis of AOAC International, 16th Edition, vol. 2 (Copyright 1995, 1996, 1997, 1998, 1999).

AOAC Official Method 997.02. Yeast and Mold Counts in Foods, Dry Rehydratable Film Method (Petrifilm Method). First Action 1997, Final Action 2000. J AOAC Int 80, 806 (1997). Revised Mar. 2002. AOAC International. One page.

Arii et al. Structural properties of recombinant ovalbumin and its transformation into a thermostabilized form by alkaline treatment. Biosci Biotechnol Biochem. Aug. 1999;63(8):1392-9.doi: 10.1271/bbb.63.1392.

Aw et al. Can too many copies spoil the broth? Microb Cell Fact. 2013; 12: 128.Published online Dec. 20, 2013. doi: 10.1186/1475-2859-12-128. 9 pages.

Charoenrat et al. Oxygen-limited fed-batch process: an alternative control for Pichia pastoris recombinant protein processes. Bioprocess Biosyst Eng. Oct. 2005;27(6):399-406. doi: 10.1007/s00449-005-0005-4. Epub Nov. 3, 2005.

Co-pending U.S. Appl. No. 16/891,835, filed Jun. 3, 2020.
Co-pending U.S. Appl. No. 16/986,016, filed Aug. 5, 2020.
Cre-Lox recombination, Wikipedia, downloaded Jun. 12, 2017.

Damasceno et al. An optimized fermentation process for high-level production of a single-chain Fv antibody fragment in Pichia pastoris. Protein Expr Purif. Sep. 2004;37(1):18-26.doi: 10.1016/j.pep.2004.03.019.

Jensen. The Basics of Western Blotting. Anat Rec (Hoboken) Mar. 2012;295(3):369-71.doi: 10.1002/ar.22424. Epub Feb. 3, 2012.

Julshamin et al. Determination of Arsenic, Cadmium, Mercury, and Lead by Inductively Coupled Plasma/Mass Spectrometry in Foods after Pressure Digestion: NMKL Interlaboratory Study. Journal of AOAC International 90(3):844-856 (2007).

Lin et al. Synthesis, Purification, and Active Site Mutagenesis of Recombinant Porcine Pepsinogen. The Journal of Biological Chemistry 264(8):4482-4489 (Mar. 15, 1989).

Lv et al. Structural and Functional Properties of Ovalbumin Glycated by Dry-Heating in the Presence of Maltodextrin. International Journal of Food Properties, 18:1326-1333, 2015. DOI: 10.1080/10942912.2011.620204. Published online Mar. 3, 2015.

Martinet et al. Modification of the protein glycosylation pathway in the methylotrophic yeast *Pichia pastoris*. Biotechnology Letters 20(12):1171-1177 (Dec. 1998).

Martinez, D. et al.) GenBank Accession No. EGR49218. Version No. EGR49218.1. glycoside hydrolase family 79 [Trichoderma reesei QM6a] (Jul. 25, 2016). Retrieved Dec. 9, 2019 at URL: https://www.ncbi.nlm.nih.gov/protein/EGR49218.1. 2 pages.

Martinez et al. Genome sequencing and analysis of the biomass-degrading fungus *Trichoderma reesei* (syn. *Hypocrea jecorina*). Nat Biotechnol 26(5):553-60 (May 2008). Epub May 4, 2008. doi: 10.1038/nbt1403.

Muñoz et al. Cloning of the authentic bovine gene encoding pepsinogen a and its expression in microbial cells. Appl Environ Microbiol. May 2004;70(5):2588-95.doi: 10.1128/aem.70.5.2588-2595.2004.

Nakayama et al., Substrate specificity of $\alpha$-1,6-mannosyltransferase that initiates N-linked mannose outer chain elongation in *Saccharomyces cerevisiae*, FEBS Letters, 412(3): 547-550 (1997).

PCT/US2019/047521 International Search Report and Written Opinion dated Jan. 2, 2020.

Pepsin Activity, Food Chemicals Codex, 11th ed, Pharmacopeial Convention, pp. 1386-1387 (2018). Retrieved Jun. 9, 2020 at URL: https://app.knovel.com/web/view/khtml/print.v/rcid:kpFCCE0042/cid:kt011MEBGL/viewerType:khtml/?notes=off.

Ramon et al. Sorbitol co-feeding reduces metabolic burden caused by the overexpression of a Rhizopus oryzae lipase in Pichia pastoris. J Biotechnol. May 31, 2007;130(1):39-46.doi: 10.1016/j.jbiotec.2007.02.025. Epub Mar. 3, 2007.

Roth et al., Identification and Quantification of Protein Glycosylation, International Journal of Carbohydrate Chemistry, vol. 2012, Article ID 640923, 10 pages.

Teh et al., Expression and analysis of the glycosylation properties of recombinant human erythropoietin expressed in Pichia pastoris, Genetics and Molecular Biology, 34(3):464-470 (2011).

Thiex et al. Determination of Ash in Animal Feed: AOAC Official Method 942.05 Revisited. J AOAC Int Sep.-Oct. 2012;95(5):1392-7.

Towbin. Western Blotting. In Encyclopedia of Immunology Second Edition, P. J. Delves, ed., pp. 2503-2507 (1998).Elsevier Ltd.

USP, Pepsin Activity. Ninth Edition of the Food Chemicals Codex (FCC 9). United States Pharmacopeia Convention, Rockville, MD, 2015e, pp. 1410-1411. Retrieved Jun. 9, 2020 at URL: https://app.knovel.com/web/view/khtml/print.v/rcid:kpFCCE0021/cid:kt00U53N01/viewerType:khtml/?notes=off.

Wang et al. Methanol-Independent Protein Expression by AOX1 Promoter with trans-Acting Elements Engineering and Glucose-Glycerol-Shift Induction in Pichia pastoris. Sci Rep. 2017; 7: 41850. Sci Rep. 2017; 7: 41850.Published online Feb. 2, 2017. doi: 10.1038/srep41850.

Yang et al. Cloning of a novel ovalbumin gene from quail oviduct and its heterologous expression in Pichia pastoris. J Basic Microbiol. Sep. 2009;49 Suppl 1:S73-8.doi: 10.1002/jobm.200900018.

Yoshimasu et al. Soluble expression and purification of porcine pepsinogen from Pichia pastoris. Protein Expression and Purification 25(2):229-236 (2002).

Zhang et al. Fermentation strategies for recombinant protein expression in the methylotrophic yeast *Pichia pastoris*. Biotechnol Bioprocess Eng 5, 275-287 (2000). DOI: https://doi.org/10.1007/BF02942184.

Duan et al. Effect of oxidative modification on structural and foaming properties of egg white protein. Food Hydrocolloids, vol. 75, pp. 223-228, (Feb. 2018). Available online Aug. 13, 2017.

Froning, Glenn W. Chapter 8: Egg Products Industry and Future Perspectives. In Egg Bioscience and Biotechnology, pp. 307-325, Mine, Ed., John Wiley & Sons, Inc. (2008).

Fredericq et al. Studies on Ovomucoid. J Biol Chem 181:499-510 (1949).

Ovalbumin, Uptima. Interchim, France. Retrieved Nov. 12, 2020 at the world wide web interchim.fr/ft/R/R5851B.pdf. Published on Apr. 8, 2009 as per Google Search results. 2 pages.

* cited by examiner

FIG. 1

Amino acid sequence of ovalbumin (SEQ ID NO: 1):

GSIGAASMEFCFDVFKELKVHHANENIFYCPIAIMSALAMVYLGAKDSTRTQINKVVRFDKLPGF
GDSIEAQCGTSVNVHSSLRDILNQITKPNDVYSFSLASRLYAEERYPILPEYLQCVKELYRGGLE
PINFQTAADQARELINSWVESQTNGIIRNVLQPSSVDSQTAMVLVNAIVFKGLWEKTFKDEDTQA
MPFRVTEQESKPVQMMYQIGLFRVASMASEKMKILELPFASGTMSMLVLLPDEVSGLEQLESIIN
FEKLTEWTSSNVMEERKIKVYLPRMKMEEKYNLTSVLMAMGITDVFSSSANLSGISSAESLKISQ
AVHAAHAEINEAGREVVGSAEAGVDAASVSEEFRADHPFLFCIKHIATNAVLFFGRCVSP

FIG. 2

Amino acid sequence of ovotransferrin (SEQ ID NO: 2):

APPKSVIRWCTISSPEEKKCNNLRDLTQQERISLTCVQKATYLDCIKAIANNEADAISLDGGQVF
EAGLAPYKLKPIAAEIYEHTEGSTTSYYAVAVVKKGTEFTVNDLQGKNSCHTGLGRSAGWNIPIG
TLLHWGAIEWEGIESGSVEQAVAKFFSASCVPGATIEQKLCRQCKGDPKTKCARNAPYSGYSGAF
HCLKDGKGDVAFVKHTTVNENAPDLNDEYELLCLDGSRQPVDNYKTCNWARVAAHAVVARDDNKV
EDIWSFLSKAQSDFGVDTKSDFHLFGPPGKKDPVLKDFLFKDSAIMLKRVPSLMDSQLYLGFEYY
SAIQSMRKDQLTPSPRENRIQWCAVGKDEKSKCDRWSVVSNGDVECTVVDETKDCIIKIMKGEAD
AVALDGGLVYTAGVCGLVPVMAERYDDESQCSKTDERPASYFAVAVARKDSNVNWNNLKGKKSCH
TAVGRTAGWVIPMGLIHNRTGTCNFDEYFSEGCAPGSPPNSRLCQLCQGSGGIPPEKCVASSHEK
YFGYTGALRCLVEKGDVAFIQHSTVEENTGGKNKADWAKNLQMDDFELLCTDGRRANVMDYRECN
LAEVPTHAVVVRPEKANKIRDLLERQEKRFGVNGSEKSKFMMFESQNKDLLFKDLTKCLFKVREG
TTYKEFLGDKFYTVISNLKTCNPSDILQMCSFLEGK

FIG. 3

Amino acid sequence of ovomucoid (SEQ ID NO: 3):

AEVDCSRFPNATDMEGKDVLVCNKDLRPICGTDGVTYTNDCLLCAYSVEFGTNISKEHDGECKET
VPMNCSSYANTTSEDGKVMVLCNRAFNPVCGTDGVTYDNECLLCAHKVEQGASVDKRHDGGCRKE
LAAVSVDCSEYPKPDCTAEDRPLCGSDNKTYGNKCNFCNAVVESNGTLTLSHFGKC

FIG. 4

Amino acid sequence of G162M F167A ovomucoid (SEQ ID NO: 4):

AEVDCSRFPNATDMEGKDVLVCNKDLRPICGTDGVTYTNDCLLCAYSVEFGTNISKEHDGECKET
VPMNCSSYANTTSEDGKVMVLCNRAFNPVCGTDGVTYDNECLLCAHKVEQGASVDKRHDGGCRKE
LAAVSVDCSEYPKPDCTAEDRPLCGSDNKTYMNKCNACNAVVESNGTLTLSHFGKC

FIG. 5

Amino acid sequence of ovoglobulin G2 (SEQ ID NO: 5):

TRAPDCGGILTPLGLSYLAEVSKPHAEVVLRQDLMAQRASDLFLGSMEPSRNRITSVKVADLWLS
VIPEAGLRLGIEVELRIAPLHAVPMPVRISIRADLHVDMGPDGNLQLLTSACRPTVQAQSTREAE
SKSSRSILDKVVDVDKLCLDVSKLLLFPNEQLMSLTALFPVTPNCQLQYLPLAAPVFSKQGIALS
LQTTFQVAGAVVPVPVSPVPFSMPELASTSTSHLILALSEHFYTSLYFTLERAGAFNMTIPSMLT
TATLAQKITQVGSLYHEDLPITLSAALRSSPRVVLEEGRAALKLFLTVHIGAGSPDFQSFLSVSA
DVTAGLQLSVSDTRMMISTAVIEDAELSLAASNVGLVRAALLEELFLAPVCQQVPAWMDDVLREG
VHLPHLSHFTYTDVNVVVHKDYVLVPCKLKLRSTMA

FIG. 6

Amino acid sequence of ovoglobulin G3 (SEQ ID NO: 6):

```
MDSISVTNAKFCFDVFNEMKVHHVNENILYCPLSILTALAMVYLGARGNTESQMKKVLHFDSITG
AGSTTDSQCGSSEYVHNLFKELLSEITRPNATYSLEIADKLYVDKTFSVLPEYLSCARKFYTGGV
EEVNFKTAAEEARQLINSWVEKETNGQIKDLLVSSSIDFGTTMVFINTIYFKGIWKIAFNTEDTR
EMPFSMTKEESKPVQMMCMNNSFNVATLPAEKMKILELPYASGDLSMLVLLPDEVSGLERIEKTI
NFDKLREWTSTNAMAKKSMKVYLPRMKIEEKYNLTSILMALGMTDLFSRSANLTGISSVDNLMIS
DAVHGVFMEVNEEGTEATGSTGAIGNIKHSLELEEFRADHPFLFFIRYNPTNAILFFGRYWSP
```

FIG. 7

Amino acid sequence of α-ovomucin (SEQ ID NO: 7):

KEPVQIVQVSTVGRSECTTWGNFHFHTFDHVKFTFPGTCTYVFASHCNDSYQDFNIKIRRSDKNS
HLIYFTVTTDGVILEVKETGITVNGNQIPLPFSLKSILIEDTCAYFQVTSKLGLTLKWNWADTLL
LDLEETYKEKICGLCGNYDGNKKNDLILDGYKMHPRQFGNFHKVEDPSEKCPDVRPDDHTGRHPT
EDDNRCSKYKKMCKKLLSRFGNCPKVVAFDDYVATCTEDMCNCVVNSSHSDLVSSCICSTLNQYS
RDCVLSKGDPGEWRTKELCYQECPSNMEYMECGNSCADTCADPERSKICKAPCTDGCFCPPGTIL
DDLGGKKCVPRDSCPCMFQGKVYSSGGTYSTPCQNCTCKGGHWSCTSLPCSGSCSIDGGFHITTF
DNKKFNFHGNCHYVLAKNTDDTFVVIGEIIQCGTSKTMTCLKNVLVTLGRTTIKICSCGSIYMNN
FIVKLPVSKDGITIFRPSTFFIKILSSTGVQIRVQMKPVMQLSITVDHSYQNRTSGLCGNFNNIQ
TDDFRTATGAVEDSAAAFGNSWKTRASCFDVEDSFEDPCSNSVDKEKFAQHWCALLSNISSTFAA
CHSVVDPSVYIKRCMYDTCNAEKSEVALCSVLSTYSRDCAAAGMTLKGWRQGICDPSEECPETMV
YNYSVKYCNQSCRSLDEPDPLCKVQIAPMEGCGCPEGTYLNDEEECVTPDDCPCYYKGKIVQPGN
SFQEDKLLCKCIQGRLDCIGETVLVKDCPAPMYYFNCSSAGPGAIGSECQKSCKTQDMHCYVTEC
VSGCMCPDGLVLDGSGGCIPKDQCPCVHGGHFYKPGETIRVDCNTCTCNKRQWNCTDSPCKGTCT
VYGNGHYMSFDGEKFDFLGDCDYILAQDFCPNNMDAGTFRIVIQNNACGKSLSICSLKITLIFES
SEIRLLEGRIQEIATDPGAEKNYKVDLRGGYIVIETTQGMSFMWDQKTTVVVHVTPSFQGKVCGL
CGDFDGRSRNDFTTRGQSVEMSIQEFGNSWKITSTCSNINMTDLCADQPFKSALGQKHCSIIKSS
VFEACHSKVNPIPYYESCVSDFCGCDSVGDCECFCTSVAAYARSCSTAGVCINWRTPAICPVFCD
YYNPPDKHEWFYKPCGAPCLKTCRNPQGKCGNILYSLEGCYPECSPDKPYFDEERRECVSLPDCT
SCNPEEKLCTEDSKDCLCCYNGKTYPLNETIYSQTEGTKCGNAFCGPNGMIIETFIPCSTLSVPA
QEQLMQPVTSAPLLSTEATPCFCTDNGQLIQMGENVSLPMNISGHCAYSICNASCQIELIWAECK
VVQTEALETCEPNSEACPPTAAPNATSLVPATALAPMSDCLGLIPPRKFNESWDFGNCQIATCLG
EENNIKLSSITCPPQQLKLCVNGFPFMKHHDETGCCEVFECQCICSGWGNEHYVTFDGTYYHFKE
NCTYVLVELIQPSSEKFWIHIDNYYCGAADGAICSMSLLIFHSNSLVILTQAKEHGKGTNLVLFN
DKKVVPDISKNGIRITSSGLYIIVEIPELEVYVSYSRLAFYIKLPFGKYYNNTMGLCGTCTNQKS
DDARKRNGEVTDSFKEMALDWKAPVSTNRYCNPGISEPVKIENYQHCEPSELCKIIWNLTECHRV
VPPQPYYEACVASRCSQQHPSTECQSMQTYAALCGLHGICVDWRGQTNGQCEATCARDQVYKPCG
EAKRNTCFSREVIVDTLLSRNNTPVFVEGCYCPDGNILLNEHDGICVSVCGCTAQDGSVKKPREA
WEHDCQYCTCDEETLNISCFPRPCAKSPPINCTKEGFVRKIKPRLDDPCCTETVCECDIKTCIIN
KTACDLGFQPVVAISEDGCCPIFSCIPKGVCVSEGVEFKPGAVVPKSSCEDCVCTDEQDAVTGTN
RIQCVPVKCQTTCQQGFRYVEKEGQCCSQCQQVACVANFPFGSVTIEVGKSYKAPYDNCTQYTCT
ESGGQFSLTSTVKVCLPFEESNCVPGTVDVTSDGCCKTCIDLPHKCKRSMKEQYIVHKHCKSAAP
VPVPFCEGTCSTYSVYSFENNEMEHKCICCHEKKSHVEKVELVCSEHKTLKFSYVHVDECGCVET
KCPMRRT

FIG. 8

Partial amino acid sequence of β-ovomucin (SEQ ID NO: 8):

```
CSTWGGGHFSTFDKYQYDFTGTCNYIFATVCDESSPDFNIQFRRGLDKKIARIIELGPSVIIVE
KDSISVRSVGVIKLPYASNGIQIAPYGRSVRLVAKLMEMELVVMWNNEDYLMVLTEKKYMGKTCG
MCGNYDGYELNDFVSEGKLLDTYKFAALQKMDDPSEICLSEEISIPAIPHKKYAVICSQLLNLVS
PTCSVPKDGFVTRCQLDMQDCSEPGQKNCTCSTLSEYSRQCAMSHQVVFNWRTENFCSVGKCSAN
QIYEECGSPCIKTCSNPEYSCSSHCTYGCFCPEGTVLDDISKNRTCVHLEQCPCTLNGETYAPGD
TMKAACRTCKCTMGQWNCKELPCPGRCSLEGGSFVTTFDSRSYRFHGVCTYILMKSSSLPHNGTL
MAIYEKSGYSHSETSLSAIIYLSTKDKIVISQNELLTDDDELKRLPYKSGDITIFKQSSMFIQMH
TEFGLELVVQTSPVFQAYVKVSAQFQGRTLGLCGNYNGDTTDDFMTSMDITEGTASLFVDSWRAG
NCLPAMERETDPCALSQLNKISAETHCSILTKKGTVFETCHAVVNPTPFYKRCVYQACNYEETFP
YICSALGSYARTCSSMGLILENWRNSMDNCTITCTGNQTFSYNTQACERTCLSLSNPTLECHPTD
IPIEGCNCPKGMYLNHKNECVRKSHCPCYLEDRKYILPDQSTMTGGITCYCVNGRLSCTGKLQNP
AESCKAPKKYISCSDSLENKYGATCAPTCQMLATGIECIPTKCESGCVCADGLYENLDGRCVPPE
ECPCEYGGLSYGKGEQIQTECEICTRKGKWKCVQKSRCSSTCNLYGEGHITTFDGQRFVFDGNC
EYILAMDGCNVNRPLSSFKIVTENVICGKSGVTCSRSISIYLGNLTIILRDETYSISGKNLQVKY
NVKKNALHLMFDIIIPGKYNMTLIWNKHMNFFIKISRETQETICGLCGNYNGNMKDDFETRSKYV
ASNELEFVNSWKENPLCGDVYFVVDPCSKNPYRKAWAEKTCSIINSQVFSACHNKVNRMPYYEAC
VRDSCGCDIGGDCECMCDAIAVYAMACLDKGICIDWRTPEFCPVYCEYYNSHRKTGSGGAYSYGS
SVNCTWHYRPCNCPNQYYKYVNIEGCYNCSHDEYFDYEKEKCMPCAMQPTSVTLPTATQPTSPST
SSASTVLTETTNPPV
```

FIG. 9

Amino acid sequence of lysozyme (SEQ ID NO: 9):

KVFGRCELAAAMKRHGLDNYRGYSLGNWVCVAKFESNFNTQATNRNTDGSTDYGILQINSRWWCN
DGRTPGSRNLCNIPCSALLSSDITASVNCAKKIVSDGNGMSAWVAWRNRCKGTDVQAWIRGCRL

FIG. 10

Amino acid sequence of ovoinhibitor (SEQ ID NO: 10):

```
IEVNCSLYASGIGKDGTSWVACPRNLKPVCGTDGSTYSNECGICLYNREHGANVEKEYDGECRPK
HVMIDCSPYLQVVRDGNTMVACPRILKPVCGSDSFTYDNECGICAYNAEHHTNISKLHDGECKLE
IGSVDCSKYPSTVSKDGRTLVACPRILSPVCGTDGFTYDNECGICAHNAEQRTHVSKKHDGKCRQ
EIPEIDCDQYPTRKTTGGKLLVRCPRILLPVCGTDGFTYDNECGICAHNAQHGTEVKKSHDGRCK
ERSTPLDCTQYLSNTQNGEAITACPFILQEVCGTDGVTYSNDCSLCAHNIELGTSVAKKHDGRCR
EEVPELDCSKYKTSTLKDGRQVVACTMIYDPVCATNGVTYASECTLCAHNLEQRTNLGKRKNGRC
EEDITKEHCREFQKVSPICTMEYVPHCGSDGVTYSNRCFFCNAYVQSNRTLNLVSMAAC
```

FIG. 11

Amino acid sequence of cystatin (SEQ ID NO: 11):

MAGARGCVVLLAAALMLVGAVLGSEDRSRLLGAPVPVDENDEGLQRALQFAMAEYNRASN
DKYSSRVVRVISAKRQLVSGIKYILQVEIGRTTCPKSSGDLQSCEFHDEPEMAKYTTCTF
VVYSIPWLNQIKLLESKCQ

FIG. 12

Amino acid sequence of ovalbumin related protein X (SEQ ID NO: 12):

MFFYNTDFRMGSISAANAEFCFDVFNELKVQHTNENILYSPLSIIVALAMVYMGARGNTEYQMEK
ALHFDSIAGLGGSTQTKVQKPKCGKSVNIHLLFKELLSDITASKANYSLRIANRLYAEKSRPILP
IYLKCVKKLYRAGLETVNFKTASDQARQLINSWVEKQTEGQIKDLLVSSSTDLDTTLVLVNAIYF
KGMWKTAFNAEDTREMPFHVTKEESKPVQMMCMNNSFNVATLPAEKMKILELPFASGDLSMLVLL
PDEVSGLERIEKTINFEKLTEWTNPNTMEKRRVKVYLPQMKIEEKYNLTSVLMALGMTDLFIPSA
NLTGISSAESLKISQAVHGAFMELSEDGIEMAGSTGVIEDIKHSPELEQFRADHPFLFLIKHNPT
NTIVYFGRYWSP

FIG. 13

Amino acid sequence of ovalbumin related protein Y (SEQ ID NO: 13):

MDSISVTNAKFCFDVFNEMKVHHVNENILYCPLSILTALAMVYLGARGNTESQMKKVLHFDSITG
AGSTTDSQCGSSEYVHNLFKELLSEITRPNATYSLEIADKLYVDKTFSVLPEYLSCARKFYTGGV
EEVNFKTAAEEARQLINSWVEKETNGQIKDLLVSSSIDFGTTMVFINTIYFKGIWKIAFNTEDTR
EMPFSMTKEESKPVQMMCMNNSFNVATLPAEKMKILELPYASGDLSMLVLLPDEVSGLERIEKTI
NFDKLREWTSTNAMAKKSMKVYLPRMKIEEKYNLTSILMALGMTDLFSRSANLTGISSVDNLMIS
DAVHGVFMEVNEEGTEATGSTGAIGNIKHSLELEEFRADHPFLFFIRYNPTNAILFFGRYWSP

SEQUENCE LISTING

```
<160> NUMBER OF SEQ ID NOS: 86

<210> SEQ ID NO 1
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gly Ser Ile Gly Ala Ala Ser Met Glu Phe Cys Phe Asp Val Phe Lys
1               5                   10                  15

Glu Leu Lys Val His His Ala Asn Glu Asn Ile Phe Tyr Cys Pro Ile
            20                  25                  30

Ala Ile Met Ser Ala Leu Ala Met Val Tyr Leu Gly Ala Lys Asp Ser
        35                  40                  45

Thr Arg Thr Gln Ile Asn Lys Val Val Arg Phe Asp Lys Leu Pro Gly
    50                  55                  60

Phe Gly Asp Ser Ile Glu Ala Gln Cys Gly Thr Ser Val Asn Val His
65                  70                  75                  80

Ser Ser Leu Arg Asp Ile Leu Asn Gln Ile Thr Lys Pro Asn Asp Val
                85                  90                  95

Tyr Ser Phe Ser Leu Ala Ser Arg Leu Tyr Ala Glu Glu Arg Tyr Pro
            100                 105                 110

Ile Leu Pro Glu Tyr Leu Gln Cys Val Lys Glu Leu Tyr Arg Gly Gly
        115                 120                 125

Leu Glu Pro Ile Asn Phe Gln Thr Ala Ala Asp Gln Ala Arg Glu Leu
    130                 135                 140

Ile Asn Ser Trp Val Glu Ser Gln Thr Asn Gly Ile Ile Arg Asn Val
145                 150                 155                 160

Leu Gln Pro Ser Ser Val Asp Ser Gln Thr Ala Met Val Leu Val Asn
                165                 170                 175

Ala Ile Val Phe Lys Gly Leu Trp Glu Lys Thr Phe Lys Asp Glu Asp
            180                 185                 190

Thr Gln Ala Met Pro Phe Arg Val Thr Glu Gln Glu Ser Lys Pro Val
        195                 200                 205

Gln Met Met Tyr Gln Ile Gly Leu Phe Arg Val Ala Ser Met Ala Ser
    210                 215                 220

Glu Lys Met Lys Ile Leu Glu Leu Pro Phe Ala Ser Gly Thr Met Ser
225                 230                 235                 240

Met Leu Val Leu Leu Pro Asp Glu Val Ser Gly Leu Glu Gln Leu Glu
                245                 250                 255

Ser Ile Ile Asn Phe Glu Lys Leu Thr Glu Trp Thr Ser Ser Asn Val
            260                 265                 270

Met Glu Glu Arg Lys Ile Lys Val Tyr Leu Pro Arg Met Lys Met Glu
        275                 280                 285
```

```
Glu Lys Tyr Asn Leu Thr Ser Val Leu Met Ala Met Gly Ile Thr Asp
        290                 295                 300

Val Phe Ser Ser Ser Ala Asn Leu Ser Gly Ile Ser Ser Ala Glu Ser
305                 310                 315                 320

Leu Lys Ile Ser Gln Ala Val His Ala Ala His Ala Glu Ile Asn Glu
                325                 330                 335

Ala Gly Arg Glu Val Val Gly Ser Ala Glu Gly Val Asp Ala Ala
            340                 345                 350

Ser Val Ser Glu Glu Phe Arg Ala Asp His Pro Phe Leu Phe Cys Ile
            355                 360                 365

Lys His Ile Ala Thr Asn Ala Val Leu Phe Phe Gly Arg Cys Val Ser
370                 375                 380

Pro
385

<210> SEQ ID NO 2
<211> LENGTH: 686
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Pro Pro Lys Ser Val Ile Arg Trp Cys Thr Ile Ser Ser Pro Glu
1               5                   10                  15

Glu Lys Lys Cys Asn Asn Leu Arg Asp Leu Thr Gln Gln Glu Arg Ile
            20                  25                  30

Ser Leu Thr Cys Val Gln Lys Ala Thr Tyr Leu Asp Cys Ile Lys Ala
        35                  40                  45

Ile Ala Asn Asn Glu Ala Asp Ala Ile Ser Leu Asp Gly Gly Gln Val
    50                  55                  60

Phe Glu Ala Gly Leu Ala Pro Tyr Lys Leu Lys Pro Ile Ala Ala Glu
65                  70                  75                  80

Ile Tyr Glu His Thr Glu Gly Ser Thr Thr Ser Tyr Tyr Ala Val Ala
                85                  90                  95

Val Val Lys Lys Gly Thr Glu Phe Thr Val Asn Asp Leu Gln Gly Lys
            100                 105                 110

Asn Ser Cys His Thr Gly Leu Gly Arg Ser Ala Gly Trp Asn Ile Pro
        115                 120                 125

Ile Gly Thr Leu Leu His Trp Gly Ala Ile Glu Trp Glu Gly Ile Glu
    130                 135                 140

Ser Gly Ser Val Glu Gln Ala Val Ala Lys Phe Phe Ser Ala Ser Cys
145                 150                 155                 160

Val Pro Gly Ala Thr Ile Glu Gln Lys Leu Cys Arg Gln Cys Lys Gly
                165                 170                 175

Asp Pro Lys Thr Lys Cys Ala Arg Asn Ala Pro Tyr Ser Gly Tyr Ser
            180                 185                 190

Gly Ala Phe His Cys Leu Lys Asp Gly Lys Gly Asp Val Ala Phe Val
        195                 200                 205

Lys His Thr Thr Val Asn Glu Asn Ala Pro Asp Leu Asn Asp Glu Tyr
    210                 215                 220

Glu Leu Leu Cys Leu Asp Gly Ser Arg Gln Pro Val Asp Asn Tyr Lys
225                 230                 235                 240

Thr Cys Asn Trp Ala Arg Val Ala Ala His Ala Val Val Ala Arg Asp
                245                 250                 255
```

```
Asp Asn Lys Val Glu Asp Ile Trp Ser Phe Leu Ser Lys Ala Gln Ser
            260                 265                 270

Asp Phe Gly Val Asp Thr Lys Ser Asp Phe His Leu Phe Gly Pro Pro
            275                 280                 285

Gly Lys Lys Asp Pro Val Leu Lys Asp Phe Leu Phe Lys Asp Ser Ala
            290                 295                 300

Ile Met Leu Lys Arg Val Pro Ser Leu Met Asp Ser Gln Leu Tyr Leu
305                 310                 315                 320

Gly Phe Glu Tyr Tyr Ser Ala Ile Gln Ser Met Arg Lys Asp Gln Leu
                325                 330                 335

Thr Pro Ser Pro Arg Glu Asn Arg Ile Gln Trp Cys Ala Val Gly Lys
            340                 345                 350

Asp Glu Lys Ser Lys Cys Asp Arg Trp Ser Val Val Ser Asn Gly Asp
            355                 360                 365

Val Glu Cys Thr Val Val Asp Glu Thr Lys Asp Cys Ile Ile Lys Ile
            370                 375                 380

Met Lys Gly Glu Ala Asp Ala Val Ala Leu Asp Gly Gly Leu Val Tyr
385                 390                 395                 400

Thr Ala Gly Val Cys Gly Leu Val Pro Val Met Ala Glu Arg Tyr Asp
                405                 410                 415

Asp Glu Ser Gln Cys Ser Lys Thr Asp Glu Arg Pro Ala Ser Tyr Phe
            420                 425                 430

Ala Val Ala Val Ala Arg Lys Asp Ser Asn Val Asn Trp Asn Asn Leu
            435                 440                 445

Lys Gly Lys Lys Ser Cys His Thr Ala Val Gly Arg Thr Ala Gly Trp
450                 455                 460

Val Ile Pro Met Gly Leu Ile His Asn Arg Thr Gly Thr Cys Asn Phe
465                 470                 475                 480

Asp Glu Tyr Phe Ser Glu Gly Cys Ala Pro Gly Ser Pro Pro Asn Ser
                485                 490                 495

Arg Leu Cys Gln Leu Cys Gln Gly Ser Gly Gly Ile Pro Pro Glu Lys
            500                 505                 510

Cys Val Ala Ser Ser His Glu Lys Tyr Phe Gly Tyr Thr Gly Ala Leu
            515                 520                 525

Arg Cys Leu Val Glu Lys Gly Asp Val Ala Phe Ile Gln His Ser Thr
            530                 535                 540

Val Glu Glu Asn Thr Gly Gly Lys Asn Lys Ala Asp Trp Ala Lys Asn
545                 550                 555                 560

Leu Gln Met Asp Asp Phe Glu Leu Leu Cys Thr Asp Gly Arg Arg Ala
                565                 570                 575

Asn Val Met Asp Tyr Arg Glu Cys Asn Leu Ala Glu Val Pro Thr His
            580                 585                 590

Ala Val Val Val Arg Pro Glu Lys Ala Asn Lys Ile Arg Asp Leu Leu
            595                 600                 605

Glu Arg Gln Glu Lys Arg Phe Gly Val Asn Gly Ser Glu Lys Ser Lys
            610                 615                 620

Phe Met Met Phe Glu Ser Gln Asn Lys Asp Leu Leu Phe Lys Asp Leu
625                 630                 635                 640

Thr Lys Cys Leu Phe Lys Val Arg Glu Gly Thr Thr Tyr Lys Glu Phe
                645                 650                 655
```

```
Leu Gly Asp Lys Phe Tyr Thr Val Ile Ser Asn Leu Lys Thr Cys Asn
            660                 665                 670

Pro Ser Asp Ile Leu Gln Met Cys Ser Phe Leu Glu Gly Lys
        675                 680                 685

<210> SEQ ID NO 3
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Glu Val Asp Cys Ser Arg Phe Pro Asn Ala Thr Asp Met Glu Gly
1               5                   10                  15

Lys Asp Val Leu Val Cys Asn Lys Asp Leu Arg Pro Ile Cys Gly Thr
            20                  25                  30

Asp Gly Val Thr Tyr Thr Asn Asp Cys Leu Leu Cys Ala Tyr Ser Val
        35                  40                  45

Glu Phe Gly Thr Asn Ile Ser Lys Glu His Asp Gly Glu Cys Lys Glu
    50                  55                  60

Thr Val Pro Met Asn Cys Ser Ser Tyr Ala Asn Thr Thr Ser Glu Asp
65                  70                  75                  80

Gly Lys Val Met Val Leu Cys Asn Arg Ala Phe Asn Pro Val Cys Gly
                85                  90                  95

Thr Asp Gly Val Thr Tyr Asp Asn Glu Cys Leu Leu Cys Ala His Lys
            100                 105                 110

Val Glu Gln Gly Ala Ser Val Asp Lys Arg His Asp Gly Gly Cys Arg
        115                 120                 125

Lys Glu Leu Ala Ala Val Ser Val Asp Cys Ser Glu Tyr Pro Lys Pro
    130                 135                 140

Asp Cys Thr Ala Glu Asp Arg Pro Leu Cys Gly Ser Asp Asn Lys Thr
145                 150                 155                 160

Tyr Gly Asn Lys Cys Asn Phe Cys Asn Ala Val Val Glu Ser Asn Gly
                165                 170                 175

Thr Leu Thr Leu Ser His Phe Gly Lys Cys
            180                 185

<210> SEQ ID NO 4
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Glu Val Asp Cys Ser Arg Phe Pro Asn Ala Thr Asp Met Glu Gly
1               5                   10                  15

Lys Asp Val Leu Val Cys Asn Lys Asp Leu Arg Pro Ile Cys Gly Thr
            20                  25                  30

Asp Gly Val Thr Tyr Thr Asn Asp Cys Leu Leu Cys Ala Tyr Ser Val
        35                  40                  45

Glu Phe Gly Thr Asn Ile Ser Lys Glu His Asp Gly Glu Cys Lys Glu
    50                  55                  60

Thr Val Pro Met Asn Cys Ser Ser Tyr Ala Asn Thr Thr Ser Glu Asp
65                  70                  75                  80
```

```
Gly Lys Val Met Val Leu Cys Asn Arg Ala Phe Asn Pro Val Cys Gly
             85                  90                  95

Thr Asp Gly Val Thr Tyr Asp Asn Glu Cys Leu Leu Cys Ala His Lys
        100                 105                 110

Val Glu Gln Gly Ala Ser Val Asp Lys Arg His Asp Gly Gly Cys Arg
            115                 120                 125

Lys Glu Leu Ala Ala Val Ser Val Asp Cys Ser Glu Tyr Pro Lys Pro
130                 135                 140

Asp Cys Thr Ala Glu Asp Arg Pro Leu Cys Gly Ser Asp Asn Lys Thr
145                 150                 155                 160

Tyr Met Asn Lys Cys Asn Ala Cys Asn Ala Val Val Glu Ser Asn Gly
                165                 170                 175

Thr Leu Thr Leu Ser His Phe Gly Lys Cys
            180                 185

<210> SEQ ID NO 5
<211> LENGTH: 426
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Thr Arg Ala Pro Asp Cys Gly Gly Ile Leu Thr Pro Leu Gly Leu Ser
1               5                  10                  15

Tyr Leu Ala Glu Val Ser Lys Pro His Ala Glu Val Val Leu Arg Gln
            20                  25                  30

Asp Leu Met Ala Gln Arg Ala Ser Asp Leu Phe Leu Gly Ser Met Glu
        35                  40                  45

Pro Ser Arg Asn Arg Ile Thr Ser Val Lys Val Ala Asp Leu Trp Leu
    50                  55                  60

Ser Val Ile Pro Glu Ala Gly Leu Arg Leu Gly Ile Glu Val Glu Leu
65                  70                  75                  80

Arg Ile Ala Pro Leu His Ala Val Pro Met Pro Val Arg Ile Ser Ile
                85                  90                  95

Arg Ala Asp Leu His Val Asp Met Gly Pro Asp Gly Asn Leu Gln Leu
            100                 105                 110

Leu Thr Ser Ala Cys Arg Pro Thr Val Gln Ala Gln Ser Thr Arg Glu
        115                 120                 125

Ala Glu Ser Lys Ser Ser Arg Ser Ile Leu Asp Lys Val Val Asp Val
    130                 135                 140

Asp Lys Leu Cys Leu Asp Val Ser Lys Leu Leu Leu Phe Pro Asn Glu
145                 150                 155                 160

Gln Leu Met Ser Leu Thr Ala Leu Phe Pro Val Thr Pro Asn Cys Gln
                165                 170                 175

Leu Gln Tyr Leu Pro Leu Ala Ala Pro Val Phe Ser Lys Gln Gly Ile
            180                 185                 190

Ala Leu Ser Leu Gln Thr Thr Phe Gln Val Ala Gly Ala Val Val Pro
        195                 200                 205

Val Pro Val Ser Pro Val Pro Phe Ser Met Pro Glu Leu Ala Ser Thr
    210                 215                 220

Ser Thr Ser His Leu Ile Leu Ala Leu Ser Glu His Phe Tyr Thr Ser
225                 230                 235                 240

Leu Tyr Phe Thr Leu Glu Arg Ala Gly Ala Phe Asn Met Thr Ile Pro
                245                 250                 255
```

```
Ser Met Leu Thr Thr Ala Thr Leu Ala Gln Lys Ile Thr Gln Val Gly
            260                 265                 270

Ser Leu Tyr His Glu Asp Leu Pro Ile Thr Leu Ser Ala Ala Leu Arg
            275                 280                 285

Ser Ser Pro Arg Val Val Leu Glu Glu Gly Arg Ala Ala Leu Lys Leu
290                 295                 300

Phe Leu Thr Val His Ile Gly Ala Gly Ser Pro Asp Phe Gln Ser Phe
305                 310                 315                 320

Leu Ser Val Ser Ala Asp Val Thr Ala Gly Leu Gln Leu Ser Val Ser
                325                 330                 335

Asp Thr Arg Met Met Ile Ser Thr Ala Val Ile Glu Asp Ala Glu Leu
            340                 345                 350

Ser Leu Ala Ala Ser Asn Val Gly Leu Val Arg Ala Ala Leu Leu Glu
            355                 360                 365

Glu Leu Phe Leu Ala Pro Val Cys Gln Gln Val Pro Ala Trp Met Asp
370                 375                 380

Asp Val Leu Arg Glu Gly Val His Leu Pro His Leu Ser His Phe Thr
385                 390                 395                 400

Tyr Thr Asp Val Asn Val Val His Lys Asp Tyr Val Leu Val Pro
            405                 410                 415

Cys Lys Leu Lys Leu Arg Ser Thr Met Ala
            420                 425

<210> SEQ ID NO 6
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asp Ser Ile Ser Val Thr Asn Ala Lys Phe Cys Phe Asp Val Phe
1               5                   10                  15

Asn Glu Met Lys Val His His Val Asn Glu Asn Ile Leu Tyr Cys Pro
            20                  25                  30

Leu Ser Ile Leu Thr Ala Leu Ala Met Val Tyr Leu Gly Ala Arg Gly
        35                  40                  45

Asn Thr Glu Ser Gln Met Lys Lys Val Leu His Phe Asp Ser Ile Thr
    50                  55                  60

Gly Ala Gly Ser Thr Thr Asp Ser Gln Cys Gly Ser Ser Glu Tyr Val
65                  70                  75                  80

His Asn Leu Phe Lys Glu Leu Leu Ser Glu Ile Thr Arg Pro Asn Ala
                85                  90                  95

Thr Tyr Ser Leu Glu Ile Ala Asp Lys Leu Tyr Val Asp Lys Thr Phe
            100                 105                 110

Ser Val Leu Pro Glu Tyr Leu Ser Cys Ala Arg Lys Phe Tyr Thr Gly
        115                 120                 125

Gly Val Glu Glu Val Asn Phe Lys Thr Ala Ala Glu Glu Ala Arg Gln
    130                 135                 140

Leu Ile Asn Ser Trp Val Glu Lys Glu Thr Asn Gly Gln Ile Lys Asp
145                 150                 155                 160

Leu Leu Val Ser Ser Ser Ile Asp Phe Gly Thr Thr Met Val Phe Ile
                165                 170                 175

Asn Thr Ile Tyr Phe Lys Gly Ile Trp Lys Ile Ala Phe Asn Thr Glu
            180                 185                 190
```

```
Asp Thr Arg Glu Met Pro Phe Ser Met Thr Lys Glu Glu Ser Lys Pro
            195                 200                 205

Val Gln Met Met Cys Met Asn Asn Ser Phe Asn Val Ala Thr Leu Pro
    210                 215                 220

Ala Glu Lys Met Lys Ile Leu Glu Leu Pro Tyr Ala Ser Gly Asp Leu
225                 230                 235                 240

Ser Met Leu Val Leu Leu Pro Asp Glu Val Ser Gly Leu Glu Arg Ile
                245                 250                 255

Glu Lys Thr Ile Asn Phe Asp Lys Leu Arg Glu Trp Thr Ser Thr Asn
            260                 265                 270

Ala Met Ala Lys Lys Ser Met Lys Val Tyr Leu Pro Arg Met Lys Ile
    275                 280                 285

Glu Glu Lys Tyr Asn Leu Thr Ser Ile Leu Met Ala Leu Gly Met Thr
290                 295                 300

Asp Leu Phe Ser Arg Ser Ala Asn Leu Thr Gly Ile Ser Ser Val Asp
305                 310                 315                 320

Asn Leu Met Ile Ser Asp Ala Val His Gly Val Phe Met Glu Val Asn
                325                 330                 335

Glu Glu Gly Thr Glu Ala Thr Gly Ser Thr Gly Ala Ile Gly Asn Ile
            340                 345                 350

Lys His Ser Leu Glu Leu Glu Glu Phe Arg Ala Asp His Pro Phe Leu
    355                 360                 365

Phe Phe Ile Arg Tyr Asn Pro Thr Asn Ala Ile Leu Phe Phe Gly Arg
370                 375                 380

Tyr Trp Ser Pro
385

<210> SEQ ID NO 7
<211> LENGTH: 2087
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Lys Glu Pro Val Gln Ile Val Gln Val Ser Thr Val Gly Arg Ser Glu
1               5                   10                  15

Cys Thr Thr Trp Gly Asn Phe His Phe His Thr Phe Asp His Val Lys
            20                  25                  30

Phe Thr Phe Pro Gly Thr Cys Thr Tyr Val Phe Ala Ser His Cys Asn
        35                  40                  45

Asp Ser Tyr Gln Asp Phe Asn Ile Lys Ile Arg Arg Ser Asp Lys Asn
    50                  55                  60

Ser His Leu Ile Tyr Phe Thr Val Thr Thr Asp Gly Val Ile Leu Glu
65                  70                  75                  80

Val Lys Glu Thr Gly Ile Thr Val Asn Gly Asn Gln Ile Pro Leu Pro
                85                  90                  95

Phe Ser Leu Lys Ser Ile Leu Ile Glu Asp Thr Cys Ala Tyr Phe Gln
            100                 105                 110

Val Thr Ser Lys Leu Gly Leu Thr Leu Lys Trp Asn Trp Ala Asp Thr
        115                 120                 125

Leu Leu Leu Asp Leu Glu Glu Thr Tyr Lys Glu Lys Ile Cys Gly Leu
    130                 135                 140

Cys Gly Asn Tyr Asp Gly Asn Lys Lys Asn Asp Leu Ile Leu Asp Gly
145                 150                 155                 160
```

```
Tyr Lys Met His Pro Arg Gln Phe Gly Asn Phe His Lys Val Glu Asp
            165                 170                 175

Pro Ser Glu Lys Cys Pro Asp Val Arg Pro Asp Asp His Thr Gly Arg
        180                 185                 190

His Pro Thr Glu Asp Asp Asn Arg Cys Ser Lys Tyr Lys Lys Met Cys
            195                 200                 205

Lys Lys Leu Leu Ser Arg Phe Gly Asn Cys Pro Lys Val Val Ala Phe
        210                 215                 220

Asp Asp Tyr Val Ala Thr Cys Thr Glu Asp Met Cys Asn Cys Val Val
225                 230                 235                 240

Asn Ser Ser His Ser Asp Leu Val Ser Cys Ile Cys Ser Thr Leu
            245                 250                 255

Asn Gln Tyr Ser Arg Asp Cys Val Leu Ser Lys Gly Asp Pro Gly Glu
        260                 265                 270

Trp Arg Thr Lys Glu Leu Cys Tyr Gln Glu Cys Pro Ser Asn Met Glu
            275                 280                 285

Tyr Met Glu Cys Gly Asn Ser Cys Ala Asp Thr Cys Ala Asp Pro Glu
        290                 295                 300

Arg Ser Lys Ile Cys Lys Ala Pro Cys Thr Asp Gly Cys Phe Cys Pro
305                 310                 315                 320

Pro Gly Thr Ile Leu Asp Asp Leu Gly Gly Lys Lys Cys Val Pro Arg
            325                 330                 335

Asp Ser Cys Pro Cys Met Phe Gln Gly Lys Val Tyr Ser Gly Gly
        340                 345                 350

Thr Tyr Ser Thr Pro Cys Gln Asn Cys Thr Cys Lys Gly Gly His Trp
            355                 360                 365

Ser Cys Thr Ser Leu Pro Cys Ser Gly Ser Cys Ser Ile Asp Gly Gly
        370                 375                 380

Phe His Ile Thr Thr Phe Asp Asn Lys Lys Phe Asn Phe His Gly Asn
385                 390                 395                 400

Cys His Tyr Val Leu Ala Lys Asn Thr Asp Asp Thr Phe Val Val Ile
            405                 410                 415

Gly Glu Ile Ile Gln Cys Gly Thr Ser Lys Thr Met Thr Cys Leu Lys
        420                 425                 430

Asn Val Leu Val Thr Leu Gly Arg Thr Thr Ile Lys Ile Cys Ser Cys
            435                 440                 445

Gly Ser Ile Tyr Met Asn Asn Phe Ile Val Lys Leu Pro Val Ser Lys
        450                 455                 460

Asp Gly Ile Thr Ile Phe Arg Pro Ser Thr Phe Phe Ile Lys Ile Leu
465                 470                 475                 480

Ser Ser Thr Gly Val Gln Ile Arg Val Gln Met Lys Pro Val Met Gln
            485                 490                 495

Leu Ser Ile Thr Val Asp His Ser Tyr Gln Asn Arg Thr Ser Gly Leu
        500                 505                 510

Cys Gly Asn Phe Asn Asn Ile Gln Thr Asp Asp Phe Arg Thr Ala Thr
            515                 520                 525

Gly Ala Val Glu Asp Ser Ala Ala Phe Gly Asn Ser Trp Lys Thr
        530                 535                 540

Arg Ala Ser Cys Phe Asp Val Glu Asp Ser Phe Glu Asp Pro Cys Ser
545                 550                 555                 560

Asn Ser Val Asp Lys Glu Lys Phe Ala Gln His Trp Cys Ala Leu Leu
            565                 570                 575
```

```
Ser Asn Ile Ser Ser Thr Phe Ala Ala Cys His Ser Val Val Asp Pro
            580                 585                 590

Ser Val Tyr Ile Lys Arg Cys Met Tyr Asp Thr Cys Asn Ala Glu Lys
        595                 600                 605

Ser Glu Val Ala Leu Cys Ser Val Leu Ser Thr Tyr Ser Arg Asp Cys
    610                 615                 620

Ala Ala Ala Gly Met Thr Leu Lys Gly Trp Arg Gln Gly Ile Cys Asp
625                 630                 635                 640

Pro Ser Glu Glu Cys Pro Glu Thr Met Val Tyr Asn Tyr Ser Val Lys
                645                 650                 655

Tyr Cys Asn Gln Ser Cys Arg Ser Leu Asp Glu Pro Asp Pro Leu Cys
            660                 665                 670

Lys Val Gln Ile Ala Pro Met Glu Gly Cys Gly Cys Pro Glu Gly Thr
        675                 680                 685

Tyr Leu Asn Asp Glu Glu Cys Val Thr Pro Asp Asp Cys Pro Cys
    690                 695                 700

Tyr Tyr Lys Gly Lys Ile Val Gln Pro Gly Asn Ser Phe Gln Glu Asp
705                 710                 715                 720

Lys Leu Leu Cys Lys Cys Ile Gln Gly Arg Leu Asp Cys Ile Gly Glu
                725                 730                 735

Thr Val Leu Val Lys Asp Cys Pro Ala Pro Met Tyr Tyr Phe Asn Cys
            740                 745                 750

Ser Ser Ala Gly Pro Gly Ala Ile Gly Ser Glu Cys Gln Lys Ser Cys
        755                 760                 765

Lys Thr Gln Asp Met His Cys Tyr Val Thr Glu Cys Val Ser Gly Cys
770                 775                 780

Met Cys Pro Asp Gly Leu Val Leu Asp Gly Ser Gly Gly Cys Ile Pro
785                 790                 795                 800

Lys Asp Gln Cys Pro Cys Val His Gly His Phe Tyr Lys Pro Gly
                805                 810                 815

Glu Thr Ile Arg Val Asp Cys Asn Thr Cys Thr Cys Asn Lys Arg Gln
            820                 825                 830

Trp Asn Cys Thr Asp Ser Pro Cys Lys Gly Thr Cys Thr Val Tyr Gly
        835                 840                 845

Asn Gly His Tyr Met Ser Phe Asp Gly Glu Lys Phe Asp Phe Leu Gly
850                 855                 860

Asp Cys Asp Tyr Ile Leu Ala Gln Asp Phe Cys Pro Asn Asn Met Asp
865                 870                 875                 880

Ala Gly Thr Phe Arg Ile Val Ile Gln Asn Asn Ala Cys Gly Lys Ser
                885                 890                 895

Leu Ser Ile Cys Ser Leu Lys Ile Thr Leu Ile Phe Glu Ser Ser Glu
            900                 905                 910

Ile Arg Leu Leu Glu Gly Arg Ile Gln Glu Ile Ala Thr Asp Pro Gly
        915                 920                 925

Ala Glu Lys Asn Tyr Lys Val Asp Leu Arg Gly Gly Tyr Ile Val Ile
930                 935                 940

Glu Thr Thr Gln Gly Met Ser Phe Met Trp Asp Gln Lys Thr Thr Val
945                 950                 955                 960

Val Val His Val Thr Pro Ser Phe Gln Gly Lys Val Cys Gly Leu Cys
                965                 970                 975

Gly Asp Phe Asp Gly Arg Ser Arg Asn Asp Phe Thr Thr Arg Gly Gln
            980                 985                 990
```

-continued

```
Ser Val Glu Met Ser Ile Gln Glu Phe Gly Asn Ser Trp Lys Ile Thr
            995                 1000                1005

Ser Thr Cys Ser Asn Ile Asn Met Thr Asp Leu Cys Ala Asp Gln
    1010                1015                1020

Pro Phe Lys Ser Ala Leu Gly Gln Lys His Cys Ser Ile Ile Lys
    1025                1030                1035

Ser Ser Val Phe Glu Ala Cys His Ser Lys Val Asn Pro Ile Pro
    1040                1045                1050

Tyr Tyr Glu Ser Cys Val Ser Asp Phe Cys Gly Cys Asp Ser Val
    1055                1060                1065

Gly Asp Cys Glu Cys Phe Cys Thr Ser Val Ala Ala Tyr Ala Arg
    1070                1075                1080

Ser Cys Ser Thr Ala Gly Val Cys Ile Asn Trp Arg Thr Pro Ala
    1085                1090                1095

Ile Cys Pro Val Phe Cys Asp Tyr Tyr Asn Pro Pro Asp Lys His
    1100                1105                1110

Glu Trp Phe Tyr Lys Pro Cys Gly Ala Pro Cys Leu Lys Thr Cys
    1115                1120                1125

Arg Asn Pro Gln Gly Lys Cys Gly Asn Ile Leu Tyr Ser Leu Glu
    1130                1135                1140

Gly Cys Tyr Pro Glu Cys Ser Pro Asp Lys Pro Tyr Phe Asp Glu
    1145                1150                1155

Glu Arg Arg Glu Cys Val Ser Leu Pro Asp Cys Thr Ser Cys Asn
    1160                1165                1170

Pro Glu Glu Lys Leu Cys Thr Glu Asp Ser Lys Asp Cys Leu Cys
    1175                1180                1185

Cys Tyr Asn Gly Lys Thr Tyr Pro Leu Asn Glu Thr Ile Tyr Ser
    1190                1195                1200

Gln Thr Glu Gly Thr Lys Cys Gly Asn Ala Phe Cys Gly Pro Asn
    1205                1210                1215

Gly Met Ile Ile Glu Thr Phe Ile Pro Cys Ser Thr Leu Ser Val
    1220                1225                1230

Pro Ala Gln Glu Gln Leu Met Gln Pro Val Thr Ser Ala Pro Leu
    1235                1240                1245

Leu Ser Thr Glu Ala Thr Pro Cys Phe Cys Thr Asp Asn Gly Gln
    1250                1255                1260

Leu Ile Gln Met Gly Glu Asn Val Ser Leu Pro Met Asn Ile Ser
    1265                1270                1275

Gly His Cys Ala Tyr Ser Ile Cys Asn Ala Ser Cys Gln Ile Glu
    1280                1285                1290

Leu Ile Trp Ala Glu Cys Lys Val Val Gln Thr Glu Ala Leu Glu
    1295                1300                1305

Thr Cys Glu Pro Asn Ser Glu Ala Cys Pro Pro Thr Ala Ala Pro
    1310                1315                1320

Asn Ala Thr Ser Leu Val Pro Ala Thr Ala Leu Ala Pro Met Ser
    1325                1330                1335

Asp Cys Leu Gly Leu Ile Pro Pro Arg Lys Phe Asn Glu Ser Trp
    1340                1345                1350

Asp Phe Gly Asn Cys Gln Ile Ala Thr Cys Leu Gly Glu Glu Asn
    1355                1360                1365

Asn Ile Lys Leu Ser Ser Ile Thr Cys Pro Pro Gln Gln Leu Lys
    1370                1375                1380
```

```
Leu Cys Val Asn Gly Phe Pro Phe Met Lys His His Asp Glu Thr
    1385                1390                1395

Gly Cys Cys Glu Val Phe Glu Cys Gln Cys Ile Cys Ser Gly Trp
    1400                1405                1410

Gly Asn Glu His Tyr Val Thr Phe Asp Gly Thr Tyr Tyr His Phe
    1415                1420                1425

Lys Glu Asn Cys Thr Tyr Val Leu Val Glu Leu Ile Gln Pro Ser
    1430                1435                1440

Ser Glu Lys Phe Trp Ile His Ile Asp Asn Tyr Tyr Cys Gly Ala
    1445                1450                1455

Ala Asp Gly Ala Ile Cys Ser Met Ser Leu Leu Ile Phe His Ser
    1460                1465                1470

Asn Ser Leu Val Ile Leu Thr Gln Ala Lys Glu His Gly Lys Gly
    1475                1480                1485

Thr Asn Leu Val Leu Phe Asn Asp Lys Lys Val Val Pro Asp Ile
    1490                1495                1500

Ser Lys Asn Gly Ile Arg Ile Thr Ser Ser Gly Leu Tyr Ile Ile
    1505                1510                1515

Val Glu Ile Pro Glu Leu Glu Val Tyr Val Ser Tyr Ser Arg Leu
    1520                1525                1530

Ala Phe Tyr Ile Lys Leu Pro Phe Gly Lys Tyr Asn Asn Thr
    1535                1540                1545

Met Gly Leu Cys Gly Thr Cys Thr Asn Gln Lys Ser Asp Asp Ala
    1550                1555                1560

Arg Lys Arg Asn Gly Glu Val Thr Asp Ser Phe Lys Glu Met Ala
    1565                1570                1575

Leu Asp Trp Lys Ala Pro Val Ser Thr Asn Arg Tyr Cys Asn Pro
    1580                1585                1590

Gly Ile Ser Glu Pro Val Lys Ile Glu Asn Tyr Gln His Cys Glu
    1595                1600                1605

Pro Ser Glu Leu Cys Lys Ile Ile Trp Asn Leu Thr Glu Cys His
    1610                1615                1620

Arg Val Val Pro Pro Gln Pro Tyr Tyr Glu Ala Cys Val Ala Ser
    1625                1630                1635

Arg Cys Ser Gln His Pro Ser Thr Glu Cys Gln Ser Met Gln
    1640                1645                1650

Thr Tyr Ala Ala Leu Cys Gly Leu His Gly Ile Cys Val Asp Trp
    1655                1660                1665

Arg Gly Gln Thr Asn Gly Cys Glu Ala Thr Cys Ala Arg Asp
    1670                1675                1680

Gln Val Tyr Lys Pro Cys Gly Glu Ala Lys Arg Asn Thr Cys Phe
    1685                1690                1695

Ser Arg Glu Val Ile Val Asp Thr Leu Leu Ser Arg Asn Asn Thr
    1700                1705                1710

Pro Val Phe Val Glu Gly Cys Tyr Cys Pro Asp Gly Asn Ile Leu
    1715                1720                1725

Leu Asn Glu His Asp Gly Ile Cys Val Ser Val Cys Gly Cys Thr
    1730                1735                1740

Ala Gln Asp Gly Ser Val Lys Lys Pro Arg Glu Ala Trp Glu His
    1745                1750                1755

Asp Cys Gln Tyr Cys Thr Cys Asp Glu Glu Thr Leu Asn Ile Ser
    1760                1765                1770
```

-continued

| | | | | | | | | | | | |
|---|---|---|---|---|---|---|---|---|---|---|---|
| Cys | Phe | Pro | Arg | Pro | Cys | Ala | Lys | Ser | Pro | Pro | Ile | Asn | Cys | Thr |
| | 1775 | | | | 1780 | | | | | 1785 | | | | |

Positions 1775-2085:

Cys Phe Pro Arg Pro Cys Ala Lys Ser Pro Pro Ile Asn Cys Thr
 1775                1780                1785

Lys Glu Gly Phe Val Arg Lys Ile Lys Pro Arg Leu Asp Asp Pro
 1790                1795                1800

Cys Cys Thr Glu Thr Val Cys Glu Cys Asp Ile Lys Thr Cys Ile
 1805                1810                1815

Ile Asn Lys Thr Ala Cys Asp Leu Gly Phe Gln Pro Val Val Ala
 1820                1825                1830

Ile Ser Glu Asp Gly Cys Cys Pro Ile Phe Ser Cys Ile Pro Lys
 1835                1840                1845

Gly Val Cys Val Ser Glu Gly Val Glu Phe Lys Pro Gly Ala Val
 1850                1855                1860

Val Pro Lys Ser Ser Cys Glu Asp Cys Val Cys Thr Asp Glu Gln
 1865                1870                1875

Asp Ala Val Thr Gly Thr Asn Arg Ile Gln Cys Val Pro Val Lys
 1880                1885                1890

Cys Gln Thr Thr Cys Gln Gln Gly Phe Arg Tyr Val Glu Lys Glu
 1895                1900                1905

Gly Gln Cys Cys Ser Gln Cys Gln Val Ala Cys Val Ala Asn
 1910                1915                1920

Phe Pro Phe Gly Ser Val Thr Ile Glu Val Gly Lys Ser Tyr Lys
 1925                1930                1935

Ala Pro Tyr Asp Asn Cys Thr Gln Tyr Thr Cys Thr Glu Ser Gly
 1940                1945                1950

Gly Gln Phe Ser Leu Thr Ser Thr Val Lys Val Cys Leu Pro Phe
 1955                1960                1965

Glu Glu Ser Asn Cys Val Pro Gly Thr Val Asp Val Thr Ser Asp
 1970                1975                1980

Gly Cys Cys Lys Thr Cys Ile Asp Leu Pro His Lys Cys Lys Arg
 1985                1990                1995

Ser Met Lys Glu Gln Tyr Ile Val His Lys His Cys Lys Ser Ala
 2000                2005                2010

Ala Pro Val Pro Val Pro Phe Cys Glu Gly Thr Cys Ser Thr Tyr
 2015                2020                2025

Ser Val Tyr Ser Phe Glu Asn Asn Glu Met Glu His Lys Cys Ile
 2030                2035                2040

Cys Cys His Glu Lys Lys Ser His Val Glu Lys Val Glu Leu Val
 2045                2050                2055

Cys Ser Glu His Lys Thr Leu Lys Phe Ser Tyr Val His Val Asp
 2060                2065                2070

Glu Cys Gly Cys Val Glu Thr Lys Cys Pro Met Arg Arg Thr
 2075                2080                2085

<210> SEQ ID NO 8
<211> LENGTH: 1185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Cys Ser Thr Trp Gly Gly His Phe Ser Thr Phe Asp Lys Tyr Gln
 1               5                   10                  15

Tyr Asp Phe Thr Gly Thr Cys Asn Tyr Ile Phe Ala Thr Val Cys Asp
                 20                  25                  30

```
Glu Ser Ser Pro Asp Phe Asn Ile Gln Phe Arg Arg Gly Leu Asp Lys
         35                  40                  45

Lys Ile Ala Arg Ile Ile Glu Leu Gly Pro Ser Val Ile Ile Val
 50                  55                  60

Glu Lys Asp Ser Ile Ser Val Arg Ser Val Gly Val Ile Lys Leu Pro
 65                  70                  75                  80

Tyr Ala Ser Asn Gly Ile Gln Ile Ala Pro Tyr Gly Arg Ser Val Arg
                 85                  90                  95

Leu Val Ala Lys Leu Met Glu Met Glu Leu Val Val Met Trp Asn Asn
             100                 105                 110

Glu Asp Tyr Leu Met Val Leu Thr Glu Lys Lys Tyr Met Gly Lys Thr
         115                 120                 125

Cys Gly Met Cys Gly Asn Tyr Asp Gly Tyr Glu Leu Asn Asp Phe Val
     130                 135                 140

Ser Glu Gly Lys Leu Leu Asp Thr Tyr Lys Phe Ala Ala Leu Gln Lys
145                 150                 155                 160

Met Asp Asp Pro Ser Glu Ile Cys Leu Ser Glu Ile Ser Ile Pro
                 165                 170                 175

Ala Ile Pro His Lys Lys Tyr Ala Val Ile Cys Ser Gln Leu Leu Asn
             180                 185                 190

Leu Val Ser Pro Thr Cys Ser Val Pro Lys Asp Gly Phe Val Thr Arg
         195                 200                 205

Cys Gln Leu Asp Met Gln Asp Cys Ser Glu Pro Gly Lys Asn Cys
     210                 215                 220

Thr Cys Ser Thr Leu Ser Glu Tyr Ser Arg Gln Cys Ala Met Ser His
225                 230                 235                 240

Gln Val Val Phe Asn Trp Arg Thr Glu Asn Phe Cys Ser Val Gly Lys
                 245                 250                 255

Cys Ser Ala Asn Gln Ile Tyr Glu Glu Cys Gly Ser Pro Cys Ile Lys
             260                 265                 270

Thr Cys Ser Asn Pro Glu Tyr Ser Cys Ser Ser His Cys Thr Tyr Gly
         275                 280                 285

Cys Phe Cys Pro Glu Gly Thr Val Leu Asp Asp Ile Ser Lys Asn Arg
     290                 295                 300

Thr Cys Val His Leu Glu Gln Cys Pro Cys Thr Leu Asn Gly Glu Thr
305                 310                 315                 320

Tyr Ala Pro Gly Asp Thr Met Lys Ala Ala Cys Arg Thr Cys Lys Cys
                 325                 330                 335

Thr Met Gly Gln Trp Asn Cys Lys Glu Leu Pro Cys Pro Gly Arg Cys
             340                 345                 350

Ser Leu Glu Gly Gly Ser Phe Val Thr Thr Phe Asp Ser Arg Ser Tyr
         355                 360                 365

Arg Phe His Gly Val Cys Thr Tyr Ile Leu Met Lys Ser Ser Ser Leu
     370                 375                 380

Pro His Asn Gly Thr Leu Met Ala Ile Tyr Glu Lys Ser Gly Tyr Ser
385                 390                 395                 400

His Ser Glu Thr Ser Leu Ser Ala Ile Ile Tyr Leu Ser Thr Lys Asp
                 405                 410                 415

Lys Ile Val Ile Ser Gln Asn Glu Leu Leu Thr Asp Asp Glu Leu
             420                 425                 430

Lys Arg Leu Pro Tyr Lys Ser Gly Asp Ile Thr Ile Phe Lys Gln Ser
         435                 440                 445
```

-continued

```
Ser Met Phe Ile Gln Met His Thr Glu Phe Gly Leu Glu Leu Val Val
450                 455                 460

Gln Thr Ser Pro Val Phe Gln Ala Tyr Val Lys Val Ser Ala Gln Phe
465                 470                 475                 480

Gln Gly Arg Thr Leu Gly Leu Cys Gly Asn Tyr Asn Gly Asp Thr Thr
            485                 490                 495

Asp Asp Phe Met Thr Ser Met Asp Ile Thr Glu Gly Thr Ala Ser Leu
        500                 505                 510

Phe Val Asp Ser Trp Arg Ala Gly Asn Cys Leu Pro Ala Met Glu Arg
    515                 520                 525

Glu Thr Asp Pro Cys Ala Leu Ser Gln Leu Asn Lys Ile Ser Ala Glu
530                 535                 540

Thr His Cys Ser Ile Leu Thr Lys Lys Gly Thr Val Phe Glu Thr Cys
545                 550                 555                 560

His Ala Val Val Asn Pro Thr Pro Phe Tyr Lys Arg Cys Val Tyr Gln
                565                 570                 575

Ala Cys Asn Tyr Glu Glu Thr Phe Pro Tyr Ile Cys Ser Ala Leu Gly
            580                 585                 590

Ser Tyr Ala Arg Thr Cys Ser Ser Met Gly Leu Ile Leu Glu Asn Trp
        595                 600                 605

Arg Asn Ser Met Asp Asn Cys Thr Ile Thr Cys Thr Gly Asn Gln Thr
    610                 615                 620

Phe Ser Tyr Asn Thr Gln Ala Cys Glu Arg Thr Cys Leu Ser Leu Ser
625                 630                 635                 640

Asn Pro Thr Leu Glu Cys His Pro Thr Asp Ile Pro Ile Glu Gly Cys
                645                 650                 655

Asn Cys Pro Lys Gly Met Tyr Leu Asn His Lys Asn Glu Cys Val Arg
            660                 665                 670

Lys Ser His Cys Pro Cys Tyr Leu Glu Asp Arg Lys Tyr Ile Leu Pro
        675                 680                 685

Asp Gln Ser Thr Met Thr Gly Gly Ile Thr Cys Tyr Cys Val Asn Gly
    690                 695                 700

Arg Leu Ser Cys Thr Gly Lys Leu Gln Asn Pro Ala Glu Ser Cys Lys
705                 710                 715                 720

Ala Pro Lys Lys Tyr Ile Ser Cys Ser Asp Ser Leu Glu Asn Lys Tyr
                725                 730                 735

Gly Ala Thr Cys Ala Pro Thr Cys Gln Met Leu Ala Thr Gly Ile Glu
            740                 745                 750

Cys Ile Pro Thr Lys Cys Glu Ser Gly Cys Val Cys Ala Asp Gly Leu
        755                 760                 765

Tyr Glu Asn Leu Asp Gly Arg Cys Val Pro Pro Glu Glu Cys Pro Cys
    770                 775                 780

Glu Tyr Gly Gly Leu Ser Tyr Gly Lys Gly Glu Gln Ile Gln Thr Glu
785                 790                 795                 800

Cys Glu Ile Cys Thr Cys Arg Lys Gly Lys Trp Lys Cys Val Gln Lys
                805                 810                 815

Ser Arg Cys Ser Ser Thr Cys Asn Leu Tyr Gly Glu Gly His Ile Thr
            820                 825                 830

Thr Phe Asp Gly Gln Arg Phe Val Phe Asp Gly Asn Cys Glu Tyr Ile
        835                 840                 845

Leu Ala Met Asp Gly Cys Asn Val Asn Arg Pro Leu Ser Ser Phe Lys
850                 855                 860
```

```
Ile Val Thr Glu Asn Val Ile Cys Gly Lys Ser Gly Val Thr Cys Ser
865                 870                 875                 880

Arg Ser Ile Ser Ile Tyr Leu Gly Asn Leu Thr Ile Ile Leu Arg Asp
                885                 890                 895

Glu Thr Tyr Ser Ile Ser Gly Lys Asn Leu Gln Val Lys Tyr Asn Val
            900                 905                 910

Lys Lys Asn Ala Leu His Leu Met Phe Asp Ile Ile Pro Gly Lys
        915                 920                 925

Tyr Asn Met Thr Leu Ile Trp Asn Lys His Met Asn Phe Phe Ile Lys
    930                 935                 940

Ile Ser Arg Glu Thr Gln Glu Thr Ile Cys Gly Leu Cys Gly Asn Tyr
945                 950                 955                 960

Asn Gly Asn Met Lys Asp Asp Phe Glu Thr Arg Ser Lys Tyr Val Ala
                965                 970                 975

Ser Asn Glu Leu Glu Phe Val Asn Ser Trp Lys Glu Asn Pro Leu Cys
            980                 985                 990

Gly Asp Val Tyr Phe Val Val Asp Pro Cys Ser Lys Asn Pro Tyr Arg
        995                 1000                1005

Lys Ala Trp Ala Glu Lys Thr Cys Ser Ile Ile Asn Ser Gln Val
    1010                1015                1020

Phe Ser Ala Cys His Asn Lys Val Asn Arg Met Pro Tyr Tyr Glu
    1025                1030                1035

Ala Cys Val Arg Asp Ser Cys Gly Cys Asp Ile Gly Gly Asp Cys
    1040                1045                1050

Glu Cys Met Cys Asp Ala Ile Ala Val Tyr Ala Met Ala Cys Leu
    1055                1060                1065

Asp Lys Gly Ile Cys Ile Asp Trp Arg Thr Pro Glu Phe Cys Pro
    1070                1075                1080

Val Tyr Cys Glu Tyr Tyr Asn Ser His Arg Lys Thr Gly Ser Gly
    1085                1090                1095

Gly Ala Tyr Ser Tyr Gly Ser Ser Val Asn Cys Thr Trp His Tyr
    1100                1105                1110

Arg Pro Cys Asn Cys Pro Asn Gln Tyr Tyr Lys Tyr Val Asn Ile
    1115                1120                1125

Glu Gly Cys Tyr Asn Cys Ser His Asp Glu Tyr Phe Asp Tyr Glu
    1130                1135                1140

Lys Glu Lys Cys Met Pro Cys Ala Met Gln Pro Thr Ser Val Thr
    1145                1150                1155

Leu Pro Thr Ala Thr Gln Pro Thr Ser Pro Ser Thr Ser Ser Ala
    1160                1165                1170

Ser Thr Val Leu Thr Glu Thr Thr Asn Pro Pro Val
    1175                1180                1185

<210> SEQ ID NO 9
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Lys Val Phe Gly Arg Cys Glu Leu Ala Ala Ala Met Lys Arg His Gly
1               5                   10                  15

Leu Asp Asn Tyr Arg Gly Tyr Ser Leu Gly Asn Trp Val Cys Val Ala
            20                  25                  30
```

```
Lys Phe Glu Ser Asn Phe Asn Thr Gln Ala Thr Asn Arg Asn Thr Asp
                35                  40                  45

Gly Ser Thr Asp Tyr Gly Ile Leu Gln Ile Asn Ser Arg Trp Trp Cys
 50                  55                  60

Asn Asp Gly Arg Thr Pro Gly Ser Arg Asn Leu Cys Asn Ile Pro Cys
 65                  70                  75                  80

Ser Ala Leu Leu Ser Ser Asp Ile Thr Ala Ser Val Asn Cys Ala Lys
                85                  90                  95

Lys Ile Val Ser Asp Gly Asn Gly Met Ser Ala Trp Val Ala Trp Arg
                100                 105                 110

Asn Arg Cys Lys Gly Thr Asp Val Gln Ala Trp Ile Arg Gly Cys Arg
            115                 120                 125

Leu

<210> SEQ ID NO 10
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ile Glu Val Asn Cys Ser Leu Tyr Ala Ser Gly Ile Gly Lys Asp Gly
 1               5                   10                  15

Thr Ser Trp Val Ala Cys Pro Arg Asn Leu Lys Pro Val Cys Gly Thr
                20                  25                  30

Asp Gly Ser Thr Tyr Ser Asn Glu Cys Gly Ile Cys Leu Tyr Asn Arg
                35                  40                  45

Glu His Gly Ala Asn Val Glu Lys Glu Tyr Asp Gly Glu Cys Arg Pro
 50                  55                  60

Lys His Val Met Ile Asp Cys Ser Pro Tyr Leu Gln Val Val Arg Asp
 65                  70                  75                  80

Gly Asn Thr Met Val Ala Cys Pro Arg Ile Leu Lys Pro Val Cys Gly
                85                  90                  95

Ser Asp Ser Phe Thr Tyr Asp Asn Glu Cys Gly Ile Cys Ala Tyr Asn
                100                 105                 110

Ala Glu His His Thr Asn Ile Ser Lys Leu His Asp Gly Glu Cys Lys
            115                 120                 125

Leu Glu Ile Gly Ser Val Asp Cys Ser Lys Tyr Pro Ser Thr Val Ser
        130                 135                 140

Lys Asp Gly Arg Thr Leu Val Ala Cys Pro Arg Ile Leu Ser Pro Val
145                 150                 155                 160

Cys Gly Thr Asp Gly Phe Thr Tyr Asp Asn Glu Cys Gly Ile Cys Ala
                165                 170                 175

His Asn Ala Glu Gln Arg Thr His Val Ser Lys Lys His Asp Gly Lys
            180                 185                 190

Cys Arg Gln Glu Ile Pro Glu Ile Asp Cys Asp Gln Tyr Pro Thr Arg
        195                 200                 205

Lys Thr Thr Gly Gly Lys Leu Leu Val Arg Cys Pro Arg Ile Leu Leu
    210                 215                 220

Pro Val Cys Gly Thr Asp Gly Phe Thr Tyr Asp Asn Glu Cys Gly Ile
225                 230                 235                 240

Cys Ala His Asn Ala Gln His Gly Thr Glu Val Lys Lys Ser His Asp
                245                 250                 255
```

-continued

```
Gly Arg Cys Lys Glu Arg Ser Thr Pro Leu Asp Cys Thr Gln Tyr Leu
        260                 265                 270

Ser Asn Thr Gln Asn Gly Glu Ala Ile Thr Ala Cys Pro Phe Ile Leu
    275                 280                 285

Gln Glu Val Cys Gly Thr Asp Gly Val Thr Tyr Ser Asn Asp Cys Ser
290                 295                 300

Leu Cys Ala His Asn Ile Glu Leu Gly Thr Ser Val Ala Lys Lys His
305                 310                 315                 320

Asp Gly Arg Cys Arg Glu Val Pro Glu Leu Asp Cys Ser Lys Tyr
            325                 330                 335

Lys Thr Ser Thr Leu Lys Asp Gly Arg Gln Val Val Ala Cys Thr Met
                340                 345                 350

Ile Tyr Asp Pro Val Cys Ala Thr Asn Gly Val Thr Tyr Ala Ser Glu
            355                 360                 365

Cys Thr Leu Cys Ala His Asn Leu Glu Gln Arg Thr Asn Leu Gly Lys
        370                 375                 380

Arg Lys Asn Gly Arg Cys Glu Glu Asp Ile Thr Lys Glu His Cys Arg
385                 390                 395                 400

Glu Phe Gln Lys Val Ser Pro Ile Cys Thr Met Glu Tyr Val Pro His
                405                 410                 415

Cys Gly Ser Asp Gly Val Thr Tyr Ser Asn Arg Cys Phe Phe Cys Asn
            420                 425                 430

Ala Tyr Val Gln Ser Asn Arg Thr Leu Asn Leu Val Ser Met Ala Ala
        435                 440                 445

Cys

<210> SEQ ID NO 11
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ala Gly Ala Arg Gly Cys Val Val Leu Leu Ala Ala Ala Leu Met
1               5                   10                  15

Leu Val Gly Ala Val Leu Gly Ser Glu Asp Arg Ser Arg Leu Leu Gly
                20                  25                  30

Ala Pro Val Pro Val Asp Glu Asn Asp Glu Gly Leu Gln Arg Ala Leu
            35                  40                  45

Gln Phe Ala Met Ala Glu Tyr Asn Arg Ala Ser Asn Asp Lys Tyr Ser
        50                  55                  60

Ser Arg Val Val Arg Val Ile Ser Ala Lys Arg Gln Leu Val Ser Gly
65                  70                  75                  80

Ile Lys Tyr Ile Leu Gln Val Glu Ile Gly Arg Thr Thr Cys Pro Lys
                85                  90                  95

Ser Ser Gly Asp Leu Gln Ser Cys Glu Phe His Asp Glu Pro Glu Met
            100                 105                 110

Ala Lys Tyr Thr Thr Cys Thr Phe Val Val Tyr Ser Ile Pro Trp Leu
        115                 120                 125

Asn Gln Ile Lys Leu Leu Glu Ser Lys Cys Gln
    130                 135
```

<210> SEQ ID NO 12
<211> LENGTH: 402
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Phe Phe Tyr Asn Thr Asp Phe Arg Met Gly Ser Ile Ser Ala Ala
1               5                   10                  15

Asn Ala Glu Phe Cys Phe Asp Val Phe Asn Glu Leu Lys Val Gln His
                20                  25                  30

Thr Asn Glu Asn Ile Leu Tyr Ser Pro Leu Ser Ile Ile Val Ala Leu
            35                  40                  45

Ala Met Val Tyr Met Gly Ala Arg Gly Asn Thr Glu Tyr Gln Met Glu
        50                  55                  60

Lys Ala Leu His Phe Asp Ser Ile Ala Gly Leu Gly Gly Ser Thr Gln
65                  70                  75                  80

Thr Lys Val Gln Lys Pro Lys Cys Gly Lys Ser Val Asn Ile His Leu
                85                  90                  95

Leu Phe Lys Glu Leu Leu Ser Asp Ile Thr Ala Ser Lys Ala Asn Tyr
            100                 105                 110

Ser Leu Arg Ile Ala Asn Arg Leu Tyr Ala Glu Lys Ser Arg Pro Ile
        115                 120                 125

Leu Pro Ile Tyr Leu Lys Cys Val Lys Lys Leu Tyr Arg Ala Gly Leu
130                 135                 140

Glu Thr Val Asn Phe Lys Thr Ala Ser Asp Gln Ala Arg Gln Leu Ile
145                 150                 155                 160

Asn Ser Trp Val Glu Lys Gln Thr Glu Gly Gln Ile Lys Asp Leu Leu
                165                 170                 175

Val Ser Ser Ser Thr Asp Leu Asp Thr Thr Leu Val Leu Val Asn Ala
            180                 185                 190

Ile Tyr Phe Lys Gly Met Trp Lys Thr Ala Phe Asn Ala Glu Asp Thr
        195                 200                 205

Arg Glu Met Pro Phe His Val Thr Lys Glu Glu Ser Lys Pro Val Gln
210                 215                 220

Met Met Cys Met Asn Asn Ser Phe Asn Val Ala Thr Leu Pro Ala Glu
225                 230                 235                 240

Lys Met Lys Ile Leu Glu Leu Pro Phe Ala Ser Gly Asp Leu Ser Met
                245                 250                 255

Leu Val Leu Leu Pro Asp Glu Val Ser Gly Leu Glu Arg Ile Glu Lys
            260                 265                 270

Thr Ile Asn Phe Glu Lys Leu Thr Glu Trp Thr Asn Pro Asn Thr Met
        275                 280                 285

Glu Lys Arg Arg Val Lys Val Tyr Leu Pro Gln Met Lys Ile Glu Glu
290                 295                 300

Lys Tyr Asn Leu Thr Ser Val Leu Met Ala Leu Gly Met Thr Asp Leu
305                 310                 315                 320

Phe Ile Pro Ser Ala Asn Leu Thr Gly Ile Ser Ser Ala Glu Ser Leu
                325                 330                 335

Lys Ile Ser Gln Ala Val His Gly Ala Phe Met Glu Leu Ser Glu Asp
            340                 345                 350

Gly Ile Glu Met Ala Gly Ser Thr Gly Val Ile Glu Asp Ile Lys His
        355                 360                 365
```

Ser Pro Glu Leu Glu Gln Phe Arg Ala Asp His Pro Phe Leu Phe Leu
370 375 380

Ile Lys His Asn Pro Thr Asn Thr Ile Val Tyr Phe Gly Arg Tyr Trp
385 390 395 400

Ser Pro

<210> SEQ ID NO 13
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Asp Ser Ile Ser Val Thr Asn Ala Lys Phe Cys Phe Asp Val Phe
1               5                   10                  15

Asn Glu Met Lys Val His His Val Asn Glu Asn Ile Leu Tyr Cys Pro
                20                  25                  30

Leu Ser Ile Leu Thr Ala Leu Ala Met Val Tyr Leu Gly Ala Arg Gly
            35                  40                  45

Asn Thr Glu Ser Gln Met Lys Lys Val Leu His Phe Asp Ser Ile Thr
        50                  55                  60

Gly Ala Gly Ser Thr Thr Asp Ser Gln Cys Gly Ser Ser Glu Tyr Val
65                  70                  75                  80

His Asn Leu Phe Lys Glu Leu Leu Ser Glu Ile Thr Arg Pro Asn Ala
                85                  90                  95

Thr Tyr Ser Leu Glu Ile Ala Asp Lys Leu Tyr Val Asp Lys Thr Phe
            100                 105                 110

Ser Val Leu Pro Glu Tyr Leu Ser Cys Ala Arg Lys Phe Tyr Thr Gly
        115                 120                 125

Gly Val Glu Glu Val Asn Phe Lys Thr Ala Ala Glu Glu Ala Arg Gln
130                 135                 140

Leu Ile Asn Ser Trp Val Glu Lys Glu Thr Asn Gly Gln Ile Lys Asp
145                 150                 155                 160

Leu Leu Val Ser Ser Ile Asp Phe Gly Thr Thr Met Val Phe Ile
                165                 170                 175

Asn Thr Ile Tyr Phe Lys Gly Ile Trp Lys Ile Ala Phe Asn Thr Glu
            180                 185                 190

Asp Thr Arg Glu Met Pro Phe Ser Met Thr Lys Glu Glu Ser Lys Pro
        195                 200                 205

Val Gln Met Met Cys Met Asn Asn Ser Phe Asn Val Ala Thr Leu Pro
210                 215                 220

Ala Glu Lys Met Lys Ile Leu Glu Leu Pro Tyr Ala Ser Gly Asp Leu
225                 230                 235                 240

Ser Met Leu Val Leu Leu Pro Asp Glu Val Ser Gly Leu Glu Arg Ile
                245                 250                 255

Glu Lys Thr Ile Asn Phe Asp Lys Leu Arg Glu Trp Thr Ser Thr Asn
            260                 265                 270

Ala Met Ala Lys Lys Ser Met Lys Val Tyr Leu Pro Arg Met Lys Ile
        275                 280                 285

Glu Glu Lys Tyr Asn Leu Thr Ser Ile Leu Met Ala Leu Gly Met Thr
290                 295                 300

Asp Leu Phe Ser Arg Ser Ala Asn Leu Thr Gly Ile Ser Ser Val Asp
305                 310                 315                 320

```
Asn Leu Met Ile Ser Asp Ala Val His Gly Val Phe Met Glu Val Asn
                325                 330                 335

Glu Glu Gly Thr Glu Ala Thr Gly Ser Thr Gly Ala Ile Gly Asn Ile
            340                 345                 350

Lys His Ser Leu Glu Leu Glu Glu Phe Arg Ala Asp His Pro Phe Leu
        355                 360                 365

Phe Phe Ile Arg Tyr Asn Pro Thr Asn Ala Ile Leu Phe Phe Gly Arg
    370                 375                 380

Tyr Trp Ser Pro
385

<210> SEQ ID NO 14
<211> LENGTH: 18
<212> TYPE: PRT
<213> ORGANISM: Unknown
<220> FEATURE:
<223> OTHER INFORMATION: Description of Unknown:
      signal peptide

<400> SEQUENCE: 14

Met Gln Val Lys Ser Ile Val Asn Leu Leu Leu Ala Cys Ser Leu Ala
1               5                   10                  15

Val Ala

<210> SEQ ID NO 15
<211> LENGTH: 22
<212> TYPE: PRT
<213> ORGANISM: Unknown
<220> FEATURE:
<223> OTHER INFORMATION: Description of Unknown:
      signal peptide

<400> SEQUENCE: 15

Met Gln Phe Asn Trp Asn Ile Lys Thr Val Ala Ser Ile Leu Ser Ala
1               5                   10                  15

Leu Thr Leu Ala Gln Ala
            20

<210> SEQ ID NO 16
<211> LENGTH: 17
<212> TYPE: PRT
<213> ORGANISM: Unknown
<220> FEATURE:
<223> OTHER INFORMATION: Description of Unknown:
      signal peptide

<400> SEQUENCE: 16

Met Tyr Arg Asn Leu Ile Ile Ala Thr Ala Leu Thr Cys Gly Ala Tyr
1               5                   10                  15

Ser

<210> SEQ ID NO 17
<211> LENGTH: 16
<212> TYPE: PRT
<213> ORGANISM: Unknown
<220> FEATURE:
<223> OTHER INFORMATION: Description of Unknown:
      signal peptide

<400> SEQUENCE: 17

Met Asn Leu Tyr Leu Ile Thr Leu Leu Phe Ala Ser Leu Cys Ser Ala
1               5                   10                  15
```

```
<210> SEQ ID NO 18
<211> LENGTH: 25
<212> TYPE: PRT
<213> ORGANISM: Unknown
<220> FEATURE:
<223> OTHER INFORMATION: Description of Unknown:
      signal peptide

<400> SEQUENCE: 18

Met Phe Glu Lys Ser Lys Phe Val Val Ser Phe Leu Leu Leu Leu Gln
1               5                   10                  15

Leu Phe Cys Val Leu Gly Val His Gly
            20                  25

<210> SEQ ID NO 19
<211> LENGTH: 21
<212> TYPE: PRT
<213> ORGANISM: Unknown
<220> FEATURE:
<223> OTHER INFORMATION: Description of Unknown:
      signal peptide

<400> SEQUENCE: 19

Met Gln Phe Asn Ser Val Val Ile Ser Gln Leu Leu Leu Thr Leu Ala
1               5                   10                  15

Ser Val Ser Met Gly
            20

<210> SEQ ID NO 20
<211> LENGTH: 16
<212> TYPE: PRT
<213> ORGANISM: Unknown
<220> FEATURE:
<223> OTHER INFORMATION: Description of Unknown:
      signal peptide

<400> SEQUENCE: 20

Met Lys Ser Gln Leu Ile Phe Met Ala Leu Ala Ser Leu Val Ala Ser
1               5                   10                  15

<210> SEQ ID NO 21
<211> LENGTH: 19
<212> TYPE: PRT
<213> ORGANISM: Unknown
<220> FEATURE:
<223> OTHER INFORMATION: Description of Unknown:
      signal peptide

<400> SEQUENCE: 21

Met Lys Phe Ala Ile Ser Thr Leu Leu Ile Ile Leu Gln Ala Ala Ala
1               5                   10                  15

Val Phe Ala

<210> SEQ ID NO 22
<211> LENGTH: 23
<212> TYPE: PRT
<213> ORGANISM: Unknown
<220> FEATURE:
<223> OTHER INFORMATION: Description of Unknown:
      signal peptide

<400> SEQUENCE: 22

Met Lys Leu Leu Asn Phe Leu Leu Ser Phe Val Thr Leu Phe Gly Leu
1               5                   10                  15

Leu Ser Gly Ser Val Phe Ala
            20
```

```
<210> SEQ ID NO 23
<211> LENGTH: 20
<212> TYPE: PRT
<213> ORGANISM: Unknown
<220> FEATURE:
<223> OTHER INFORMATION: Description of Unknown:
      signal peptide

<400> SEQUENCE: 23

Met Ile Phe Asn Leu Lys Thr Leu Ala Ala Val Ala Ile Ser Ile Ser
1               5                   10                  15

Gln Val Ser Ala
            20

<210> SEQ ID NO 24
<211> LENGTH: 19
<212> TYPE: PRT
<213> ORGANISM: Unknown
<220> FEATURE:
<223> OTHER INFORMATION: Description of Unknown:
      signal peptide

<400> SEQUENCE: 24

Met Lys Ile Ser Ala Leu Thr Ala Cys Ala Val Thr Leu Ala Gly Leu
1               5                   10                  15

Ala Ile Ala

<210> SEQ ID NO 25
<211> LENGTH: 18
<212> TYPE: PRT
<213> ORGANISM: Unknown
<220> FEATURE:
<223> OTHER INFORMATION: Description of Unknown:
      signal peptide

<400> SEQUENCE: 25

Met Ser Tyr Leu Lys Ile Ser Ala Leu Leu Ser Val Leu Ser Val Ala
1               5                   10                  15

Leu Ala

<210> SEQ ID NO 26
<211> LENGTH: 20
<212> TYPE: PRT
<213> ORGANISM: Unknown
<220> FEATURE:
<223> OTHER INFORMATION: Description of Unknown:
      signal peptide

<400> SEQUENCE: 26

Met Leu Ser Thr Ile Leu Asn Ile Phe Ile Leu Leu Leu Phe Ile Gln
1               5                   10                  15

Ala Ser Leu Gln
            20

<210> SEQ ID NO 27
<211> LENGTH: 20
<212> TYPE: PRT
<213> ORGANISM: Unknown
<220> FEATURE:
<223> OTHER INFORMATION: Description of Unknown:
      signal peptide
```

```
<400> SEQUENCE: 27

Met Lys Leu Ser Thr Asn Leu Ile Leu Ala Ile Ala Ala Ala Ser Ala
1               5                   10                  15

Val Val Ser Ala
            20

<210> SEQ ID NO 28
<211> LENGTH: 19
<212> TYPE: PRT
<213> ORGANISM: Unknown
<220> FEATURE:
<223> OTHER INFORMATION: Description of Unknown:
      signal peptide

<400> SEQUENCE: 28

Met Phe Lys Ser Leu Cys Met Leu Ile Gly Ser Cys Leu Leu Ser Ser
1               5                   10                  15

Val Leu Ala

<210> SEQ ID NO 29
<211> LENGTH: 19
<212> TYPE: PRT
<213> ORGANISM: Unknown
<220> FEATURE:
<223> OTHER INFORMATION: Description of Unknown:
      signal peptide

<400> SEQUENCE: 29

Met Lys Leu Ala Ala Leu Ser Thr Ile Ala Leu Thr Ile Leu Pro Val
1               5                   10                  15

Ala Leu Ala

<210> SEQ ID NO 30
<211> LENGTH: 23
<212> TYPE: PRT
<213> ORGANISM: Unknown
<220> FEATURE:
<223> OTHER INFORMATION: Description of Unknown:
      signal peptide

<400> SEQUENCE: 30

Met Ser Phe Ser Ser Asn Val Pro Gln Leu Phe Leu Leu Leu Val Leu
1               5                   10                  15

Leu Thr Asn Ile Val Ser Gly
            20

<210> SEQ ID NO 31
<211> LENGTH: 18
<212> TYPE: PRT
<213> ORGANISM: Unknown
<220> FEATURE:
<223> OTHER INFORMATION: Description of Unknown:
      signal peptide

<400> SEQUENCE: 31

Met Gln Leu Gln Tyr Leu Ala Val Leu Cys Ala Leu Leu Leu Asn Val
1               5                   10                  15

Gln Ser

<210> SEQ ID NO 32
<211> LENGTH: 19
<212> TYPE: PRT
<213> ORGANISM: Unknown
```

```
<220> FEATURE:
<223> OTHER INFORMATION: Description of Unknown:
      signal peptide

<400> SEQUENCE: 32

Met Lys Ile His Ser Leu Leu Leu Trp Asn Leu Phe Phe Ile Pro Ser
1               5                   10                  15

Ile Leu Gly

<210> SEQ ID NO 33
<211> LENGTH: 19
<212> TYPE: PRT
<213> ORGANISM: Unknown
<220> FEATURE:
<223> OTHER INFORMATION: Description of Unknown:
      signal peptide

<400> SEQUENCE: 33

Met Ser Thr Leu Thr Leu Leu Ala Val Leu Leu Ser Leu Gln Asn Ser
1               5                   10                  15

Ala Leu Ala

<210> SEQ ID NO 34
<211> LENGTH: 20
<212> TYPE: PRT
<213> ORGANISM: Unknown
<220> FEATURE:
<223> OTHER INFORMATION: Description of Unknown:
      signal peptide

<400> SEQUENCE: 34

Met Ile Asn Leu Asn Ser Phe Leu Ile Leu Thr Val Thr Leu Leu Ser
1               5                   10                  15

Pro Ala Leu Ala
            20

<210> SEQ ID NO 35
<211> LENGTH: 16
<212> TYPE: PRT
<213> ORGANISM: Unknown
<220> FEATURE:
<223> OTHER INFORMATION: Description of Unknown:
      signal peptide

<400> SEQUENCE: 35

Met Phe Ser Leu Ala Val Gly Ala Leu Leu Thr Gln Ala Phe Gly
1               5                   10                  15

<210> SEQ ID NO 36
<211> LENGTH: 16
<212> TYPE: PRT
<213> ORGANISM: Unknown
<220> FEATURE:
<223> OTHER INFORMATION: Description of Unknown:
      signal peptide

<400> SEQUENCE: 36

Met Lys Ile Leu Ser Ala Leu Leu Leu Phe Thr Leu Ala Phe Ala
1               5                   10                  15

<210> SEQ ID NO 37
<211> LENGTH: 20
<212> TYPE: PRT
<213> ORGANISM: Unknown
```

<220> FEATURE:
<223> OTHER INFORMATION: Description of Unknown:
      signal peptide

<400> SEQUENCE: 37

Met Lys Val Ser Thr Thr Lys Phe Leu Ala Val Phe Leu Leu Val Arg
1               5                   10                  15

Leu Val Cys Ala
            20

<210> SEQ ID NO 38
<211> LENGTH: 19
<212> TYPE: PRT
<213> ORGANISM: Unknown
<220> FEATURE:
<223> OTHER INFORMATION: Description of Unknown:
      signal peptide

<400> SEQUENCE: 38

Met Gln Phe Gly Lys Val Leu Phe Ala Ile Ser Ala Leu Ala Val Thr
1               5                   10                  15

Ala Leu Gly

<210> SEQ ID NO 39
<211> LENGTH: 18
<212> TYPE: PRT
<213> ORGANISM: Unknown
<220> FEATURE:
<223> OTHER INFORMATION: Description of Unknown:
      signal peptide

<400> SEQUENCE: 39

Met Trp Ser Leu Phe Ile Ser Gly Leu Leu Ile Phe Tyr Pro Leu Val
1               5                   10                  15

Leu Gly

<210> SEQ ID NO 40
<211> LENGTH: 21
<212> TYPE: PRT
<213> ORGANISM: Unknown
<220> FEATURE:
<223> OTHER INFORMATION: Description of Unknown:
      signal peptide

<400> SEQUENCE: 40

Met Arg Asn His Leu Asn Asp Leu Val Val Leu Phe Leu Leu Leu Thr
1               5                   10                  15

Val Ala Ala Gln Ala
            20

<210> SEQ ID NO 41
<211> LENGTH: 18
<212> TYPE: PRT
<213> ORGANISM: Unknown
<220> FEATURE:
<223> OTHER INFORMATION: Description of Unknown:
      signal peptide

<400> SEQUENCE: 41

Met Phe Leu Lys Ser Leu Leu Ser Phe Ala Ser Ile Leu Thr Leu Cys
1               5                   10                  15

Lys Ala

-continued

```
<210> SEQ ID NO 42
<211> LENGTH: 20
<212> TYPE: PRT
<213> ORGANISM: Unknown
<220> FEATURE:
<223> OTHER INFORMATION: Description of Unknown:
      signal peptide

<400> SEQUENCE: 42

Met Phe Val Phe Glu Pro Val Leu Leu Ala Val Leu Val Ala Ser Thr
1               5                   10                  15

Cys Val Thr Ala
            20

<210> SEQ ID NO 43
<211> LENGTH: 22
<212> TYPE: PRT
<213> ORGANISM: Unknown
<220> FEATURE:
<223> OTHER INFORMATION: Description of Unknown:
      signal peptide

<400> SEQUENCE: 43

Met Val Ser Leu Arg Ser Ile Phe Thr Ser Ser Ile Leu Ala Ala Gly
1               5                   10                  15

Leu Thr Arg Ala His Gly
            20

<210> SEQ ID NO 44
<211> LENGTH: 22
<212> TYPE: PRT
<213> ORGANISM: Unknown
<220> FEATURE:
<223> OTHER INFORMATION: Description of Unknown:
      signal peptide

<400> SEQUENCE: 44

Met Phe Ser Pro Ile Leu Ser Leu Glu Ile Ile Leu Ala Leu Ala Thr
1               5                   10                  15

Leu Gln Ser Val Phe Ala
            20

<210> SEQ ID NO 45
<211> LENGTH: 16
<212> TYPE: PRT
<213> ORGANISM: Unknown
<220> FEATURE:
<223> OTHER INFORMATION: Description of Unknown:
      signal peptide

<400> SEQUENCE: 45

Met Ile Ile Asn His Leu Val Leu Thr Ala Leu Ser Ile Ala Leu Ala
1               5                   10                  15

<210> SEQ ID NO 46
<211> LENGTH: 19
<212> TYPE: PRT
<213> ORGANISM: Unknown
<220> FEATURE:
<223> OTHER INFORMATION: Description of Unknown:
      signal peptide

<400> SEQUENCE: 46

Met Leu Ala Leu Val Arg Ile Ser Thr Leu Leu Leu Leu Ala Leu Thr
1               5                   10                  15

Ala Ser Ala
```

```
<210> SEQ ID NO 47
<211> LENGTH: 17
<212> TYPE: PRT
<213> ORGANISM: Unknown
<220> FEATURE:
<223> OTHER INFORMATION: Description of Unknown:
      signal peptide

<400> SEQUENCE: 47

Met Arg Pro Val Leu Ser Leu Leu Leu Leu Ala Ser Ser Val Leu
1               5                   10                  15

Ala

<210> SEQ ID NO 48
<211> LENGTH: 24
<212> TYPE: PRT
<213> ORGANISM: Unknown
<220> FEATURE:
<223> OTHER INFORMATION: Description of Unknown:
      signal peptide

<400> SEQUENCE: 48

Met Val Leu Ile Gln Asn Phe Leu Pro Leu Phe Ala Tyr Thr Leu Phe
1               5                   10                  15

Phe Asn Gln Arg Ala Ala Leu Ala
            20

<210> SEQ ID NO 49
<211> LENGTH: 21
<212> TYPE: PRT
<213> ORGANISM: Unknown
<220> FEATURE:
<223> OTHER INFORMATION: Description of Unknown:
      signal peptide

<400> SEQUENCE: 49

Met Lys Phe Pro Val Pro Leu Leu Phe Leu Leu Gln Leu Phe Phe Ile
1               5                   10                  15

Ile Ala Thr Gln Gly
            20

<210> SEQ ID NO 50
<211> LENGTH: 20
<212> TYPE: PRT
<213> ORGANISM: Unknown
<220> FEATURE:
<223> OTHER INFORMATION: Description of Unknown:
      signal peptide

<400> SEQUENCE: 50

Met Val Ser Leu Thr Arg Leu Leu Ile Thr Gly Ile Ala Thr Ala Leu
1               5                   10                  15

Gln Val Asn Ala
            20

<210> SEQ ID NO 51

<400> SEQUENCE: 51

000

<210> SEQ ID NO 52
<211> LENGTH: 31
<212> TYPE: PRT
<213> ORGANISM: Unknown
```

```
<220> FEATURE:
<223> OTHER INFORMATION: Description of Unknown:
      signal peptide

<400> SEQUENCE: 52

Met Val Leu Val Gly Leu Leu Thr Arg Leu Val Pro Leu Val Leu Leu
1               5                   10                  15

Ala Gly Thr Val Leu Leu Leu Val Phe Val Val Leu Ser Gly Gly
            20                  25                  30

<210> SEQ ID NO 53
<211> LENGTH: 16
<212> TYPE: PRT
<213> ORGANISM: Unknown
<220> FEATURE:
<223> OTHER INFORMATION: Description of Unknown:
      signal peptide

<400> SEQUENCE: 53

Met Leu Ser Ile Leu Ser Ala Leu Thr Leu Leu Gly Leu Ser Cys Ala
1               5                   10                  15

<210> SEQ ID NO 54
<211> LENGTH: 20
<212> TYPE: PRT
<213> ORGANISM: Unknown
<220> FEATURE:
<223> OTHER INFORMATION: Description of Unknown:
      signal peptide

<400> SEQUENCE: 54

Met Arg Leu Leu His Ile Ser Leu Leu Ser Ile Ile Ser Val Leu Thr
1               5                   10                  15

Lys Ala Asn Ala
            20

<210> SEQ ID NO 55
<211> LENGTH: 19
<212> TYPE: PRT
<213> ORGANISM: Unknown
<220> FEATURE:
<223> OTHER INFORMATION: Description of Unknown:
      signal peptide

<400> SEQUENCE: 55

Met Arg Phe Pro Ser Ile Phe Thr Ala Val Leu Phe Ala Ala Ser Ser
1               5                   10                  15

Ala Leu Ala

<210> SEQ ID NO 56
<211> LENGTH: 17
<212> TYPE: PRT
<213> ORGANISM: Unknown
<220> FEATURE:
<223> OTHER INFORMATION: Description of Unknown:
      signal peptide

<400> SEQUENCE: 56

Met Phe Lys Ser Val Val Tyr Ser Ile Leu Ala Ala Ser Leu Ala Asn
1               5                   10                  15

Ala
```

```
<210> SEQ ID NO 57
<211> LENGTH: 19
<212> TYPE: PRT
<213> ORGANISM: Unknown
<220> FEATURE:
<223> OTHER INFORMATION: Description of Unknown:
      signal peptide

<400> SEQUENCE: 57

Met Leu Leu Gln Ala Phe Leu Phe Leu Leu Ala Gly Phe Ala Ala Lys
1               5                   10                  15

Ile Ser Ala

<210> SEQ ID NO 58
<211> LENGTH: 21
<212> TYPE: PRT
<213> ORGANISM: Unknown
<220> FEATURE:
<223> OTHER INFORMATION: Description of Unknown:
      signal peptide

<400> SEQUENCE: 58

Met Ala Ser Ser Asn Leu Leu Ser Leu Ala Leu Phe Leu Val Leu Leu
1               5                   10                  15

Thr His Ala Asn Ser
            20

<210> SEQ ID NO 59
<211> LENGTH: 16
<212> TYPE: PRT
<213> ORGANISM: Unknown
<220> FEATURE:
<223> OTHER INFORMATION: Description of Unknown:
      signal peptide

<400> SEQUENCE: 59

Met Asn Ile Phe Tyr Ile Phe Leu Phe Leu Leu Ser Phe Val Gln Gly
1               5                   10                  15

<210> SEQ ID NO 60
<211> LENGTH: 15
<212> TYPE: PRT
<213> ORGANISM: Unknown
<220> FEATURE:
<223> OTHER INFORMATION: Description of Unknown:
      signal peptide

<400> SEQUENCE: 60

Met Leu Ile Ile Val Leu Leu Phe Leu Ala Thr Leu Ala Asn Ser
1               5                   10                  15

<210> SEQ ID NO 61
<211> LENGTH: 36
<212> TYPE: PRT
<213> ORGANISM: Unknown
<220> FEATURE:
<223> OTHER INFORMATION: Description of Unknown:
      signal peptide

<400> SEQUENCE: 61

Met Glu Ser Val Ser Ser Leu Phe Asn Ile Phe Ser Thr Ile Met Val
1               5                   10                  15

Asn Tyr Lys Ser Leu Val Leu Ala Leu Leu Ser Val Ser Asn Leu Lys
                20                  25                  30

Tyr Ala Arg Gly
            35
```

-continued

```
<210> SEQ ID NO 62
<211> LENGTH: 18
<212> TYPE: PRT
<213> ORGANISM: Unknown
<220> FEATURE:
<223> OTHER INFORMATION: Description of Unknown:
      signal peptide

<400> SEQUENCE: 62

Met Phe Ala Phe Tyr Phe Leu Thr Ala Cys Ile Ser Leu Lys Gly Val
1               5                   10                  15

Phe Gly

<210> SEQ ID NO 63
<211> LENGTH: 23
<212> TYPE: PRT
<213> ORGANISM: Unknown
<220> FEATURE:
<223> OTHER INFORMATION: Description of Unknown:
      signal peptide

<400> SEQUENCE: 63

Met Arg Phe Ser Thr Thr Leu Ala Thr Ala Ala Thr Ala Leu Phe Phe
1               5                   10                  15

Thr Ala Ser Gln Val Ser Ala
            20

<210> SEQ ID NO 64
<211> LENGTH: 16
<212> TYPE: PRT
<213> ORGANISM: Unknown
<220> FEATURE:
<223> OTHER INFORMATION: Description of Unknown:
      signal peptide

<400> SEQUENCE: 64

Met Lys Phe Ala Tyr Ser Leu Leu Leu Pro Leu Ala Gly Val Ser Ala
1               5                   10                  15

<210> SEQ ID NO 65
<211> LENGTH: 16
<212> TYPE: PRT
<213> ORGANISM: Unknown
<220> FEATURE:
<223> OTHER INFORMATION: Description of Unknown:
      signal peptide

<400> SEQUENCE: 65

Met Lys Phe Phe Ala Ile Ala Ala Leu Phe Ala Ala Ala Ala Val Ala
1               5                   10                  15

<210> SEQ ID NO 66
<211> LENGTH: 15
<212> TYPE: PRT
<213> ORGANISM: Unknown
<220> FEATURE:
<223> OTHER INFORMATION: Description of Unknown:
      signal peptide

<400> SEQUENCE: 66

Met Gln Phe Phe Ala Val Ala Leu Phe Ala Thr Ser Ala Leu Ala
1               5                   10                  15

<210> SEQ ID NO 67
<211> LENGTH: 18
<212> TYPE: PRT
<213> ORGANISM: Unknown
```

```
<220> FEATURE:
<223> OTHER INFORMATION: Description of Unknown:
      signal peptide

<400> SEQUENCE: 67

Met Lys Trp Val Thr Phe Ile Ser Leu Leu Phe Leu Phe Ser Ser Ala
1               5                   10                  15

Tyr Ser

<210> SEQ ID NO 68
<211> LENGTH: 18
<212> TYPE: PRT
<213> ORGANISM: Unknown
<220> FEATURE:
<223> OTHER INFORMATION: Description of Unknown:
      signal peptide

<400> SEQUENCE: 68

Met Arg Ser Leu Leu Ile Leu Val Leu Cys Phe Leu Pro Leu Ala Ala
1               5                   10                  15

Leu Gly

<210> SEQ ID NO 69
<211> LENGTH: 15
<212> TYPE: PRT
<213> ORGANISM: Unknown
<220> FEATURE:
<223> OTHER INFORMATION: Description of Unknown:
      signal peptide

<400> SEQUENCE: 69

Met Lys Val Leu Ile Leu Ala Cys Leu Val Ala Leu Ala Leu Ala
1               5                   10                  15

<210> SEQ ID NO 70
<211> LENGTH: 18
<212> TYPE: PRT
<213> ORGANISM: Unknown
<220> FEATURE:
<223> OTHER INFORMATION: Description of Unknown:
      signal peptide

<400> SEQUENCE: 70

Met Phe Asn Leu Lys Thr Ile Leu Ile Ser Thr Leu Ala Ser Ile Ala
1               5                   10                  15

Val Ala

<210> SEQ ID NO 71
<211> LENGTH: 20
<212> TYPE: PRT
<213> ORGANISM: Unknown
<220> FEATURE:
<223> OTHER INFORMATION: Description of Unknown:
      signal peptide

<400> SEQUENCE: 71

Met Tyr Arg Lys Leu Ala Val Ile Ser Ala Phe Leu Ala Thr Ala Arg
1               5                   10                  15

Ala Gln Ser Ala
            20

<210> SEQ ID NO 72
<211> LENGTH: 42
<212> TYPE: PRT
<213> ORGANISM: Unknown
```

-continued

```
<220> FEATURE:
<223> OTHER INFORMATION: Description of Unknown:
      signal peptide

<400> SEQUENCE: 72

Ala Tyr Val Pro Ser Glu Pro Trp Ser Thr Leu Thr Pro Asp Ala Ser
1               5                   10                  15

Leu Glu Ser Ala Leu Lys Asp Tyr Ser Gln Thr Phe Gly Ile Ala Ile
            20                  25                  30

Lys Ser Leu Asp Ala Asp Lys Ile Lys Arg
        35                  40

<210> SEQ ID NO 73
<211> LENGTH: 6
<212> TYPE: PRT
<213> ORGANISM: Unknown
<220> FEATURE:
<223> OTHER INFORMATION: Description of Unknown:
      signal peptide

<400> SEQUENCE: 73

Ile Thr Leu Pro Lys Arg
1               5

<210> SEQ ID NO 74
<211> LENGTH: 15
<212> TYPE: PRT
<213> ORGANISM: Unknown
<220> FEATURE:
<223> OTHER INFORMATION: Description of Unknown:
      signal peptide

<400> SEQUENCE: 74

Ala Pro Leu Glu His Gln Gln Gln His His Lys His Glu Lys Arg
1               5                   10                  15

<210> SEQ ID NO 75
<211> LENGTH: 21
<212> TYPE: PRT
<213> ORGANISM: Unknown
<220> FEATURE:
<223> OTHER INFORMATION: Description of Unknown:
      signal peptide

<400> SEQUENCE: 75

Ala Pro Ala Pro Lys Pro Glu Asp Cys Thr Thr Thr Val Gln Lys Arg
1               5                   10                  15

His Gln His Lys Arg
            20

<210> SEQ ID NO 76
<211> LENGTH: 16
<212> TYPE: PRT
<213> ORGANISM: Unknown
<220> FEATURE:
<223> OTHER INFORMATION: Description of Unknown:
      signal peptide

<400> SEQUENCE: 76

Ala Pro Val Ala Pro Ala Glu Glu Ala Ala Asn His Leu His Lys Arg
1               5                   10                  15

<210> SEQ ID NO 77
<211> LENGTH: 28
<212> TYPE: PRT
<213> ORGANISM: Unknown
```

```
<220> FEATURE:
<223> OTHER INFORMATION: Description of Unknown:
      signal peptide

<400> SEQUENCE: 77

Lys Asn Val Val Asp Phe Ser Arg Phe Gly Asp Ala Lys Ile Ser Pro
1               5                   10                  15

Asp Asp Thr Asp Leu Glu Ser Arg Glu Arg Lys Arg
            20                  25

<210> SEQ ID NO 78
<211> LENGTH: 18
<212> TYPE: PRT
<213> ORGANISM: Unknown
<220> FEATURE:
<223> OTHER INFORMATION: Description of Unknown:
      signal peptide

<400> SEQUENCE: 78

Leu Pro Lys Asn Val Leu Glu Glu Gln Gln Ala Lys Asp Asp Leu Ala
1               5                   10                  15

Lys Arg

<210> SEQ ID NO 79
<211> LENGTH: 66
<212> TYPE: PRT
<213> ORGANISM: Unknown
<220> FEATURE:
<223> OTHER INFORMATION: Description of Unknown:
      signal peptide

<400> SEQUENCE: 79

Ala Pro Val Asn Thr Thr Thr Glu Asp Glu Thr Ala Gln Ile Pro Ala
1               5                   10                  15

Glu Ala Val Ile Gly Tyr Leu Asp Leu Glu Gly Asp Phe Asp Val Ala
            20                  25                  30

Val Leu Pro Phe Ser Asn Ser Thr Asn Asn Gly Leu Leu Phe Ile Asn
        35                  40                  45

Thr Thr Ile Ala Ser Ile Ala Ala Lys Glu Glu Gly Val Ser Leu Asp
    50                  55                  60

Lys Arg
65

<210> SEQ ID NO 80
<211> LENGTH: 4
<212> TYPE: PRT
<213> ORGANISM: Unknown
<220> FEATURE:
<223> OTHER INFORMATION: Description of Unknown:
      signal peptide

<400> SEQUENCE: 80

Glu Ala Glu Ala
1

<210> SEQ ID NO 81
<211> LENGTH: 13
<212> TYPE: PRT
<213> ORGANISM: Unknown
<220> FEATURE:
<223> OTHER INFORMATION: Description of Unknown:
      signal peptide
```

```
<400> SEQUENCE: 81

Leu Glu His Thr His Arg Arg Gly Ser Leu Val Lys Arg
1               5                   10

<210> SEQ ID NO 82
<211> LENGTH: 33
<212> TYPE: PRT
<213> ORGANISM: Unknown
<220> FEATURE:
<223> OTHER INFORMATION: Description of Unknown:
      signal peptide

<400> SEQUENCE: 82

Leu Asp Cys Ser Gly Asp Val Phe Phe Gly Tyr Thr Arg Gly Asp Lys
1               5                   10                  15

Thr Asp Val His Lys Ser Gln Ala Leu Thr Ala Val Lys Asn Ile Lys
            20                  25                  30

Arg

<210> SEQ ID NO 83
<211> LENGTH: 13
<212> TYPE: PRT
<213> ORGANISM: Unknown
<220> FEATURE:
<223> OTHER INFORMATION: Description of Unknown:
      signal peptide

<400> SEQUENCE: 83

Met Pro Thr Ser Glu Arg Gln Gln Gly Leu Glu Glu Arg
1               5                   10

<210> SEQ ID NO 84
<211> LENGTH: 7
<212> TYPE: PRT
<213> ORGANISM: Unknown
<220> FEATURE:
<223> OTHER INFORMATION: Description of Unknown:
      signal peptide

<400> SEQUENCE: 84

Ser Val Ile Asn Tyr Lys Arg
1               5

<210> SEQ ID NO 85
<211> LENGTH: 6
<212> TYPE: PRT
<213> ORGANISM: Unknown
<220> FEATURE:
<223> OTHER INFORMATION: Description of Unknown:
      signal peptide

<400> SEQUENCE: 85

Gln Pro Leu Glu Asp Arg
1               5

<210> SEQ ID NO 86
<211> LENGTH: 6
<212> TYPE: PRT
<213> ORGANISM: Unknown
<220> FEATURE:
<223> OTHER INFORMATION: Description of Unknown:
      signal peptide
```

```
<400> SEQUENCE: 86

Arg Gly Val Phe Arg Arg
1               5
```

RECOMBINANT ANIMAL-FREE FOOD COMPOSITIONS AND METHODS OF MAKING THEM

CROSS REFERENCE TO RELATED APPLICATIONS

This application is a continuation of U.S. patent application Ser. No. 15/522,986, filed Apr. 28, 2017, which is a 371 International Application PCT/US2015/060147, filed Nov. 11, 2015, which claims the benefit of U.S. Provisional Patent Application No. 62/078,385, filed Nov. 11, 2014, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 2, 2019, is named 49160701301SL.txt and is 83,577 bytes in size.

BACKGROUND OF THE INVENTION

The growing consumer demand for health-conscious fast food options has seen egg white demand at all-time highs in recent years. The success of recently introduced "healthy option" menu items in fast food chains (e.g., McDonald's "egg white delight" breakfast sandwich) and the growing awareness of the link between coronary heart disease and excessive cholesterol consumption have moved consumers to eschew cholesterol-rich egg yolk in favor of relatively high protein, low carbohydrate egg white preparations. This trend has contributed to all-time lows in worldwide dried egg white stocks while the cost of liquid egg whites increased 80% through 2013. This trend is expected to continue, with 2014 July prices double what they were a year earlier and tripling over those in 2012. The dramatic rise in price affects manufacturers of ready-made foodstuffs in particular (e.g., makers of baking mixes), where egg whites are a key ingredient.

Egg-free alternatives to egg protein production aim to offer a solution to the appalling conditions of hen-laying chickens, which ultimately bear the strain of producer's efforts to cut costs and meet a growing worldwide demand. Aside from an increasingly health conscious consumer base, there is widespread recognition of the inhumane conditions of hens subjected to large scale industrial hatchery practices, supported by a scientific consensus of their capability for complex social behaviors and evidence of stress apparent in factory-farmed versus free-roaming egg-laying hens. Such aversion to the inhumane aspects of the industrial hatchery may fuel acceptance and ultimately preference of animal-free egg white alternatives over factory-farmed eggs.

Animal-free egg protein production potentials are not dependent on the productivity of egg-laying hens and are unaffected by market uncertainties due to widespread outbreaks of disease or shortages or price increases in feedstocks. Furthermore, as has been suggested by recent worldwide outbreaks of avian-borne diseases, the risk of avian-to-human transmission is exacerbated by farming practices that rely on frequent human contact and the maintenance of dense hen populations. Adoption of an animal-free approach to egg protein production can be viewed as a protective measure against the risk of future avian-to-human disease transmission.

There is a need for alternative egg-free, egg white protein production methods which uncouple production and price from uncertainties in worldwide egg stocks and price variations respectively. Such methods would be attractive options to, for example, fast-food chains which wish to incorporate egg-white options into their menu, as well as manufacturers of egg-white-based food mixes.

SUMMARY OF THE INVENTION

In one aspect, the present disclosure provides a method of producing an egg white protein composition, the method comprising: recombinantly expressing two or more egg white proteins; and mixing the two or more egg white proteins. In some embodiments, the egg white proteins may be selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof. In any one of the preceding embodiments, the recombinantly expressing the two or more egg white proteins may occur in one or more host cells. In any one of the preceding embodiments, the method may further comprise secreting the two or more egg white proteins from the one or more host cells. In any one of the preceding embodiments, the recombinantly expressing the two or more egg white proteins may occur using cell-free protein synthesis. In any one of the preceding embodiments, the method may further comprise adding a food additive to the egg white protein composition. In any one of the preceding embodiments, the method may further comprise desugaring, stabilizing, or removing glucose from the egg white protein composition. In any one of the preceding embodiments, the method may further comprise pasteurizing or ultrapasteurizing the egg white protein composition. In any one of the preceding embodiments, the method may further comprise drying the egg white protein composition. In any one of the preceding embodiments, the method may further comprise enzymatically, chemically, or mechanically digesting one or more of the two or more egg white proteins.

In one aspect, the present disclosure provides a processed consumable product comprising one or more recombinant egg white proteins or fragments thereof. In some embodiments, the one or more egg white proteins may be selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof. In any one of the preceding embodiments, the processed consumable product may comprise two or more, three or more, four or more, five or more, or six or more egg white proteins or fragments thereof. In any one of the preceding embodiments, the processed consumable product may lack one or more, two or more, three or more, five or more, ten or more, or twenty or more egg white proteins. In any one of the preceding embodiments, the processed consumable product may lack ovomucoid. In any one of the preceding embodiments, the processed consumable product may lack one or more, two or more, three or more, five or more, ten or more, or twenty or more egg yolk proteins. In any one of the preceding embodiments, the processed consumable product may be selected from the group consisting of food product, beverage product, dietary supplement, food additive, pharmaceutical product, hygiene product, and any combination thereof, such as from the group consisting of food product and beverage product.

In one aspect, the present disclosure provides a method of producing a consumable product, the method comprising: recombinantly expressing one or more egg white proteins; and mixing the one or more egg white proteins with one or more ingredients to produce a consumable product. In some embodiments, the one or more ingredients may comprise food additives. In any one of the preceding embodiments, the one or more ingredients may comprise egg white proteins. In any one of the preceding embodiments, the one or more ingredients may comprise recombinant egg white proteins. In any one of the preceding embodiments, the one or more ingredients may not comprise egg white proteins. In any one of the preceding embodiments, the one or more egg white proteins may comprise two or more, three or more, four or more, or five or more egg white proteins.

In one aspect, the present disclosure provides a method for producing an egg white protein or fragment thereof, the method comprising: recombinantly expressing the egg white protein or fragment thereof in a host cell, wherein the host cell may comprise a polynucleotide encoding the egg white protein or fragment thereof, and wherein the egg white protein may be selected from the group consisting of ovoglobulin G2, ovoglobulin G3, α-ovomucin, β-ovomucin, ovoglycoprotein, flavoprotein, ovomacroglobulin, cystatin, and any combination thereof, such as from the group consisting of ovoglobulin G2, ovoglobulin G3, ovoglycoprotein, flavoprotein, ovomacroglobulin, cystatin, and any combination thereof. In some embodiments, the method may further comprise secreting the egg white protein or fragment thereof from the host cell. In any one of the preceding embodiments, the method may further comprise purifying the egg white protein or fragment thereof. In any one of the preceding embodiments, the method may further comprise recombinantly expressing a second egg white protein or fragment thereof in the host cell. In any one of the preceding embodiments, the fragment may comprise at least 10%, 20%, 30%, 40%, or 50% of the egg white protein.

In one aspect, the present disclosure provides a method for producing two or more egg white proteins or fragments thereof, the method comprising recombinantly expressing the two or more egg white proteins or fragments thereof in a host cell. In some embodiments, the host cell may comprise one or more polynucleotides encoding the two or more egg white proteins or fragments thereof. In any one of the preceding embodiments, the method may further comprise secreting the two or more egg white proteins or fragments thereof from the host cell. In any one of the preceding embodiments, the method may further comprise purifying the two or more egg white proteins or fragments thereof. In any one of the preceding embodiments, the two or more egg white proteins may be selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof.

In one aspect, the present disclosure provides an isolated recombinant egg white protein selected from the group consisting of ovoglobulin G2, ovoglobulin G3, α-ovomucin, β-ovomucin, ovoglycoprotein, flavoprotein, ovomacroglobulin, cystatin, and any combination thereof, such as from the group consisting of ovoglobulin G2, ovoglobulin G3, ovoglycoprotein, flavoprotein, ovomacroglobulin, cystatin, and any combination thereof. In some embodiments, the isolated recombinant egg white protein may have a glycosylation, acetylation, or phosphorylation pattern different from the egg white protein in an egg white. In any one of the preceding embodiments, the isolated recombinant egg white protein may have a melting temperature different from the egg white protein in an egg white, such as a higher or lower melting temperature relative to the egg white protein in an egg white. In any one of the preceding embodiments, the isolated recombinant egg white protein may comprise one or more amino acid insertions, deletions, or substitutions relative to the egg white protein in an egg white. In any one of the preceding embodiments, the isolated recombinant egg white protein may be selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and any combination thereof.

In one aspect, the present disclosure provides an isolated mutant ovomucoid, comprising tryptophan. In some embodiments, the isolated mutant ovomucoid may be recombinantly expressed. In any one of the preceding embodiments, the isolated mutant ovomucoid may be a complete protein. In any one of the preceding embodiments, the isolated mutant ovomucoid may comprise one or more, two or more, three or more, four or more, five or more, or six or more amino acid insertions or substitutions relative to SEQ ID: NO: 3 when optimally aligned. In any one of the preceding embodiments, the isolated mutant ovomucoid may comprise one or more amino acid substitutions, wherein the amino acid substitutions may comprise one or more, two or more, three or more, four or more, five or more, or six or more tyrosine to tryptophan substitutions. In any one of the preceding embodiments, the isolated mutant ovomucoid may comprise up to four, five, six, or ten amino acid insertions or substitutions relative to SEQ ID: NO: 3 when optimally aligned. In any one of the preceding embodiments, the isolated mutant ovomucoid may comprise one or more, two or more, three or more, or four or more tryptophan residues. In any one of the preceding embodiments, the isolated mutant ovomucoid may comprise one or more, two or more, three or more, or four or more tryptophan residues at the N-terminus or C-terminus. In any one of the preceding embodiments, the isolated mutant ovomucoid may comprise a methionine at position 162 and an alanine at position 167 relative to SEQ ID NO: 3 when optimally aligned. In any one of the preceding embodiments, the isolated mutant ovomucoid may have reduced allergenicity relative to wild-type ovomucoid. In any one of the preceding embodiments, the isolated mutant ovomucoid may have enhanced digestibility relative to wild-type ovomucoid.

In one aspect, the present disclosure provides an egg white protein composition comprising: an isolated recombinant egg white protein or an isolated mutant ovomucoid described herein; and one or more egg white proteins. In some embodiments, the one or more egg white proteins may be recombinantly expressed.

In one aspect, the present disclosure provides an egg white protein composition comprising two or more recombinant egg white proteins.

In some embodiments, for an egg white protein composition described herein, the two or more recombinant egg white proteins may be selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof. In any one of the preceding embodiments, the egg white protein composition may comprise ovalbumin. In any one of the preceding embodiments, the egg white protein composition may comprise an isolated recombinant egg white protein described herein. In any one of the preceding embodiments, the egg white protein composition may comprise an isolated mutant ovomucoid described herein. In any one of the preceding embodiments, the egg white proteins may have sequences derived from a single species. In any one of the preceding embodiments, the species may be *Gallus gallus domesticus*. In any one of the preceding embodiments, the species may be other than *Gallus gallus domesticus*. In any one of the preceding embodiments, the egg white proteins may have sequences derived from more than one species. In any one of the preceding embodiments, the egg white proteins may have sequences derived from a bird selected from the group consisting of poultry, fowl, waterfowl, game bird, chicken, quail, turkey, duck, ostrich, goose, gull, guineafowl, pheasant, emu, and any combination thereof. In any one of the preceding embodiments, the egg white protein composition may comprise three or more, four or more, or five or more egg white proteins. In any one of the preceding embodiments, the egg white protein composition may comprise up to 5, 10, 15, or 20 egg white proteins. In any one of the preceding embodiments, the egg white protein composition may further comprise water. In any one of the preceding embodiments, the egg white protein composition may have a percentage of water up to 95%. In any one of the preceding embodiments, the egg white protein composition may have a percentage of water within the range from 80% to 95%. In any one of the preceding embodiments, the egg white protein composition may comprise at least 90% protein by dry weight. In any one of the preceding embodiments, the egg white protein composition may further comprise a food additive. In any one of the preceding embodiments, the food additive may be selected from the group consisting of a sweetener, salt, carbohydrate, and any combination thereof.

In any one of the preceding embodiments, the egg white protein composition may lack cholesterol. In any one of the preceding embodiments, the egg white protein composition may comprise less than 5% fat by dry weight. In any one of the preceding embodiments, the egg white protein composition may lack fat, saturated fat, or trans fat. In any one of the preceding embodiments, the egg white protein composition may lack glucose. In any one of the preceding embodiments, the egg white protein composition may lack one or more egg white proteins, such as ovomucoid or flavoprotein. In any one of the preceding embodiments, the one or more egg white proteins may be selected from the group consisting of tenp, clusterin, CH21, VMO-1, vitellogenin, zona pellucida C protein, ovotransferrin BC type, ovoinhibitor precursor, ovomucoid precursor, clusterin precursor, Hep21 protein precursor, ovoglycoprotein precursor, extracellular fatty acid-binding protein, extracellular fatty acid-binding protein precursor, prostaglandin D2 syntmay havee brain precursor, marker protein, vitellogenin-1, vitellogenin-2, vitellogenin-2 precursor, vitellogenin-3, riboflavin binding protein, hemopexin, serum albumin precursor, apolipoprotein D, ovosecretoglobulin, Hep21, glutathione peroxidase 3, lipocalin-type prostaglandin D syntmay havee/chondrogenesis-associated lipocalin, apovitellenin-1, dickkopf-related protein 3, gallinacin-11 (VMO-II, β-defensin-11), serum albumin (α-livetin), gallin, secretory trypsin inhibitor, lymphocyte antigen 86, actin, Ig µ chain C region, sulfhydryl oxidase 1, histone H4, angiopoietin-like protein 3, ubiquitin, ovocalyxin-32, polymeric immunoglobulin receptor, peptidyl-prolyl-cis/trans isomerase B, aminopeptidase Ey, pleiotrophin, midkine, renin/prorenin receptor, TIMP-2, TIMP-3, histone H2B variants, Ig λ chain, FAMC3 protein, α-enolase, 60S acidic ribosomal protein P1, cytotactin/tenascin, CEPU-1, selenoprotein, elongation factor 1-α 1, epididymal secretory protein, El, 14-3-3 Protein ξ (zeta), olfactomedin-like protein 3, glutathione S-transferase 2, β-2-microglobulin, RGD-CAP, apolipoprotein B, golgi apparatus protein 1, cochlin, proteasome subunit α type-7, apolipoprotein A-I, eukaryotic initiation factor 4A-II, ASPIC/cartilage acidic protein 1, triosephosphate isomerase, proteasome subunit α-type, Ig λ chain C-region, procollagen-lysine 2-oxoglutarate 5-dioxgenase 1, ADP-ribosylation factor 5, calmodulin, protein disulfide-isomerase, annexin I, elongation factor 2, peroxiredoxin-1, HSP70, protein disulfide isomerase A3, calreticulin, 40S ribosomal protein SA/laminin receptor 1, α-Actinin-4, tumor necrosis factor-related apoptosis-inducing ligand, vitamin D-binding protein, semaphorin-3C, endoplasmin, catalase, hepatic α-amylase, transitional ER ATPase, cadherin-1, angiotensin-converting enzyme, bone morphogenetic protein 1, guanine nucleotide-binding protein subunit β2-like 1, histidine ammonia lyase, annexin A2, β-catenin, RAB-GDP dissociation inhibitor, lamin-A, ovocleidin-116, aminopeptidase, HSP90-α, hypoxia up-regulated protein 1, heat shock cognate protein HSP90 β, ATP-citrate syntmay havee, myosin-9, and any combination thereof. In any one of the preceding embodiments, the egg white protein composition may lack two or more, three or more, five or more, ten or more, or twenty or more egg white proteins. In any one of the preceding embodiments, the egg white protein composition is not an egg, egg white, or egg yolk.

In any one of the preceding embodiments, the egg white protein composition may further comprise one or more egg white proteins selected from the group consisting of tenp, clusterin, CH21, VMO-1, vitellogenin, zona pellucida C protein, ovotransferrin BC type, ovoinhibitor precursor, ovomucoid precursor, clusterin precursor, Hep21 protein precursor, ovoglycoprotein precursor, extracellular fatty acid-binding protein, extracellular fatty acid-binding protein precursor, prostaglandin D2 syntmay havee brain precursor, marker protein, vitellogenin-1, vitellogenin-2, vitellogenin-2 precursor, vitellogenin-3, riboflavin binding protein, hemopexin, serum albumin precursor, apolipoprotein D, ovosecretoglobulin, Hep21, glutathione peroxidase 3, lipocalin-type prostaglandin D syntmay havee/chondrogenesis-associated lipocalin, apovitellenin-1, dickkopf-related protein 3, gallinacin-11 (VMO-II, β-defensin-11), serum albumin (α-livetin), gallin, secretory trypsin inhibitor, lymphocyte antigen 86, actin, Ig μ chain C region, sulfhydryl oxidase 1, histone H4, angiopoietin-like protein 3, ubiquitin, ovocalyxin-32, polymeric immunoglobulin receptor, peptidyl-prolyl-cis/trans isomerase B, aminopeptidase Ey, pleiotrophin, midkine, renin/prorenin receptor, TIMP-2, TIMP-3, histone H2B variants, Ig λ chain, FAMC3 protein, α-enolase, 60S acidic ribosomal protein Pl, cytotactin/tenascin, CEPU-1, selenoprotein, elongation factor 1-α 1, epididymal secretory protein, El, 14-3-3 Protein ξ (zeta), olfactomedin-like protein 3, glutathione S-transferase 2, β-2-microglobulin, RGD-CAP, apolipoprotein B, golgi apparatus protein 1, cochlin, proteasome subunit α type-7, apolipoprotein A-I, eukaryotic initiation factor 4A-II, ASPIC/cartilage acidic protein 1, triosephosphate isomerase, proteasome subunit α-type, Ig λ chain C-region, procollagen-lysine 2-oxoglutarate 5-dioxgenase 1, ADP-ribosylation factor 5, calmodulin, protein disulfide-isomerase, annexin I, elongation factor 2, peroxiredoxin-1, HSP70, protein disulfide isomerase A3, calreticulin, 40S ribosomal protein SA/laminin receptor 1, α-Actinin-4, tumor necrosis factor-related apoptosis-inducing ligand, vitamin D-binding protein, semaphorin-3C, endoplasmin, catalase, hepatic α-amylase, transitional ER ATPase, cadherin-1, angiotensin-converting enzyme, bone morphogenetic protein 1, guanine nucleotide-binding protein subunit β2-like 1, histidine ammonia lyase, annexin A2, β-catenin, RAB-GDP dissociation inhibitor, lamin-A, ovocleidin-116, aminopeptidase, HSP90-α, hypoxia up-regulated protein 1, heat shock cognate protein HSP90 β, ATP-citrate syntmay havee, and myosin-9, and any combination thereof.

In any one of the preceding embodiments, the egg white protein composition may have a pH within the range from 6 to 10. In any one of the preceding embodiments, the egg white protein composition may have a foam height within the range from 10 mm to 60 mm, such as from 30 mm to 60 mm. In any one of the preceding embodiments, the egg white protein composition may have a foam height of at least 30 mm. In any one of the preceding embodiments, the egg white protein composition may have a foam height greater than a foam height of an egg white. In any one of the preceding embodiments, the egg white protein composition may have a foam seep up to 10 mm or up to 5 mm at 30 minutes after whipping. In any one of the preceding embodiments, the egg white protein composition may have a foam seep less than a foam seep of an egg white at 30 minutes after whipping. In any one of the preceding embodiments, the egg white protein composition may have a foam strength within the range from 30 g to 100 g, such as from 40 g to 100 g. In any one of the preceding embodiments, the egg white protein composition may have a foam strength greater than a foam strength of an egg white. In any one of the preceding embodiments, the egg white protein composition may have a gel strength within the range from 100 g to 1500 g, from 500 g to 1500 g, or from 700 g to 1500 g. In any one of the preceding embodiments, the egg white protein composition may have a gel strength greater than a gel strength of an egg white. In any one of the preceding embodiments, the egg white protein composition may have a shelf life of at least one, two, three, or six months. In any one of the preceding embodiments, the egg white protein composition may have reduced allergenicity relative to an egg white. In any one of the preceding embodiments, the egg white protein composition may be a liquid. In any one of the preceding embodiments, the egg white protein composition may be a solid or powder. In any one of the preceding embodiments, the egg white protein composition may be frozen.

In one aspect, the present disclosure provides a polynucleotide encoding an isolated recombinant egg white protein or isolated mutant ovomucoid described herein. In some embodiments, the polynucleotide may be codon optimized. In any one of the preceding embodiments, the polynucleotide may be DNA or RNA. In any one of the preceding embodiments, the polynucleotide may further encode a signal peptide. In any one of the preceding embodiments, the signal peptide may be at the N-terminus of the egg white protein or polypeptide. In any one of the preceding embodiments, the signal peptide may be selected from the group consisting of acid phosphatase, albumin, alkaline extracellular protease, α-mating factor, amylase, β-casein, carbohydrate binding module family 21-starch binding domain, carboxypeptidase Y, cellobiohydrolase I, dipeptidyl protease, glucoamylase, heat shock protein, hydrophobin, inulase, invertase, killer protein or killer toxin, leucine-rich artificial signal peptide CLY-L8, lysozyine, phytohemagglutinin, maltose binding protein, P-factor, *Pichia pastoris* Dse, *Pichia pastoris* Exg, *Pichia pastoris* Pirl, *Pichia pastoris* Scw, Pir4, and any combination thereof. In any one of the preceding embodiments, the signal peptide may be selected from the group consisting of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, and SEQ ID NOS 72-86 and any combination thereof. In any one of the preceding embodiments, the signal peptide may be up to 100 amino acids in length. In any one of the preceding embodiments, the polynucleotide may further encode a signal peptidase cleavage or recognition site. In any one of the preceding embodiments, the signal peptidase may be selected from the group consisting of KEX2, Krpl, Enterokinase (EKT), thrombin, factor Xa (FXa), Tobacco Etch Virus (TEV), 3C Prescission, and any combination thereof.

In one aspect, the present disclosure provides an expression vector comprising a polynucleotide described herein. In some embodiments, the expression vector may further comprise a promoter. In any one of the preceding embodiments, the promoter may be a constitutive promoter, an inducible promoter, or a hybrid promoter. In any one of the preceding embodiments, the promoter may be selected from the group consisting of acu-5, adhl+, alcohol dehydrogenase (ADH1, ADH2, ADH4), AHSB4m, AINV, alcA, α-amylase, alternative oxidase (AOD), alcohol oxidase I (AOX1), alcohol oxidase 2 (AOX2), AXDH, B2, CaMV, cellobiohydrolase I (cbhl), ccg-1, cDNA1, cellular filament polypeptide (cfp), cpc-2, ctr4+, CUP1, dihydroxyacetone syntmay havee (DAS), enolase (ENO, ENO1), formaldehyde dehydrogenase (FLD1), FMD, formate dehydrogenase (FMDH), G1, G6, GAA, GAL1, GAL2, GAL3, GAL4, GAL5, GAL6, GAL7, GAL8, GAL9, GAL10, GCW14, gdhA, gla-1, α-glucoamylase (glaA), glyceraldehyde-3-phosphate dehydrogenase (gpdA, GAP, GAPDH), phosphoglycerate mutase (GPM1), glycerol kinase (GUT1), HSP82, invl+, isocitrate lyase (ICL1), acetohydroxy acid isomeroreductase (ILV5), KAR2, KEX2, β-galactosidase (lac4), LEU2, me1O, MET3, methanol oxidase (MOX), nmtl, NSP, pcbC, PET9, peroxin 8 (PEX8), phosphoglycerate kinase (PGK, PGK1), phol, PHO5, PH089, phosphatidylinositol syntmay havee (PIS1), PYK1, pyruvate kinase (pkil), RPS7, sorbitol dehydrogenase (SDH), 3-phosphoserine aminotransferase (SERI), SSA4, SV40, TEF, translation elongation factor 1 alpha (TEF1), THI11 homoserine kinase (THR1), tpi, TPS1, triose phosphate isomerase (TPI1), XRP2, YPT1, and any combination thereof. In any one of the preceding embodiments, the expression vector may further comprise an auxotrophic marker. In any one of the preceding embodiments, the auxotrophic marker may be selected from the group consisting of adel, arg4, his4, ura3, met2, and any combination thereof. In any one of the preceding embodiments, the expression vector may further comprise a selectable marker. In any one of the preceding embodiments, the selectable marker may be a resistance gene. In any one of the preceding embodiments, the resistance gene may confer resistance to zeocin, ampicillin, blasticidin, kanamycin, nurseothricin, chloroamphenicol, tetracycline, triclosan, ganciclovir, or any combination thereof. In any one of the preceding embodiments, the expression vector may comprise a plasmid.

In one aspect, the present disclosure provides a host cell transformed to express one or more heterologous egg white proteins, wherein the host cell are not selected from the group consisting of *Escherichia coli, Pichia pastoris*, rice, *Aspergillus niger, Aspergillus oryzae, Acremonium chrysogenum, Saccharomyces cerevisiae*, insect, mice, corn, *Pseudozyma*, tobacco, zebrafish, and any combination thereof.

In one aspect, the present disclosure provides a host cell transformed to express one or more heterologous egg white proteins, wherein the one or more egg white proteins are not selected from the group consisting of ovalbumin, ovotransferrin, lysozyme, ovostatin, ovomucoid, ovoinhibitor, avidin, and any combination thereof.

In one aspect, the present disclosure provides a host cell comprising a polynucleotide described herein.

In one aspect, the present disclosure provides a host cell comprising an expression vector described herein. In some embodiments, the expression vector may be genomically integrated. In any one of the preceding embodiments, the host cell may comprise multiple copies of the expression vector.

In any one of the preceding embodiments, the host cell may be selected from the group consisting of bacteria, fungi, plant, insect, mammalian, and any combination thereof. In any one of the preceding embodiments, the fungi may be a yeast or filamentous fungi. In any one of the preceding embodiments, the yeast may be selected from the group consisting of *Arxula* spp., *Arxula adeninivorans, Kluyveromyces* spp., *Kluyveromyces lactis, Pichia* spp., *Pichia angusta, Pichia pastoris, Saccharomyces* spp., *Saccharomyces cerevisiae, Schizosaccharomyces* spp., *Schizosaccharomyces pombe, Yarrowia* spp., *Yarrowia lipolytica*, and any combination thereof. In any one of the preceding embodiments, the fungi may be selected from the group consisting of *Agaricus* spp., *Agaricus bisporus, Aspergillus* spp., *Aspergillus awamori, Aspergillus fumigatus, Aspergillus nidulans, Aspergillus niger, Aspergillus oryzae, Colletotrichum* spp., *Colletotrichum gloeosporiodes, Endothia* spp., *Endothia parasitica, Fusarium* spp., *Fusarium graminearum, Fusarium solani, Mucor* spp., *Mucor miehei, Mucor pusillus, Myceliophthora* spp., *Myceliophthora thermophila, Neurospora* spp., *Neurospora crassa, Penicillium* spp., *Penicillium camemberti, Penicillium canescens, Penicillium chrysogenum, Penicillium (Talaromyces) emersonii, Penicillium funiculosum, Penicillium purpurogenum, Penicillium roqueforti, Pleurotus* spp., *Pleurotus ostreatus, Rhizomucor* spp., *Rhizomucor miehei, Rhizomucor pusillus, Rhizopus* spp., *Rhizopus arrhizus, Rhizopus oligosporus, Rhizopus oryzae, Trichoderma* spp., *Trichoderma altroviride, Trichoderma reesei, Trichoderma vireus*, and any combination thereof. In any one of the preceding embodiments, the host cell may be selected from the group consisting of *Aspergillus oryzae, Bacillus subtilis, Escherichia coli, Myceliophthora thermophila, Neurospora crassa, Pichia pastoris*, and any combination thereof. In any one of the preceding embodiments, the host cell may be approved as generally regarded as safe by the U.S. Food and Drug Administration. In any one of the preceding embodiments, the host cell may be auxotrophic.

In one aspect, the present disclosure provides a cell culture comprising a host cell described herein.

In one aspect, the present disclosure provides a method for making a consumable product, the method comprising substituting a portion of an egg-based ingredient with an isolated recombinant egg white protein, isolated mutant ovomucoid, or egg white protein composition described herein.

In one aspect, the present disclosure provides a method for making a consumable product, the method comprising adding an isolated recombinant egg white protein, isolated mutant ovomucoid, or egg white protein composition described herein.

In one aspect, the present disclosure provides a method of using a recombinant egg white protein as a processing agent to make a processed consumable product. In some embodiments, the method may further comprise removing the recombinant egg white protein.

In one aspect, the present disclosure provides a method of using an isolated recombinant egg white protein, isolated mutant ovomucoid, or egg white protein composition described herein as a processing agent to make a processed consumable product. In some embodiments, the method may further comprise removing the isolated recombinant egg white protein, isolated mutant ovomucoid, or egg white protein composition.

In any one of the preceding embodiments, the processing agent acts as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a consumable product comprising an isolated recombinant egg white protein, isolated mutant ovomucoid, or egg white protein composition described herein. In some embodiments, the consumable product may be selected from the group consisting of food product, beverage product, pharmaceutical product, hygiene product, and any combination thereof.

In one aspect, the present disclosure provides a method of using a recombinant egg white protein as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a method of using an isolated recombinant egg white protein, isolated mutant ovomucoid, or egg white protein composition described herein as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a method for diagnosing a food allergy, the method comprising introducing an isolated recombinant egg white protein, isolated mutant ovomucoid, or egg white protein composition described herein to a subject. In some embodiments, the introducing may be performed using a skin prick test, blood test, or oral food challenge.

In one aspect, the present disclosure provides a method for treating a food allergy, the method comprising substituting an egg white allergen with an isolated recombinant egg white protein, isolated mutant ovomucoid, or egg white protein composition described herein or increasing a tolerance to an egg white allergen of a subject by consuming an isolated recombinant egg white protein, isolated mutant ovomucoid, or egg white protein composition described herein.

In one aspect, the present disclosure provides a method for inhibiting malolactic fermentation in wine, the method comprising providing an egg white lysozyme to wine. In some embodiments, the egg white lysozyme may be recombinantly expressed.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is an amino acid sequence of ovalbumin (SEQ ID NO: 1).

FIG. 2 is an amino acid sequence of ovotransferrin (SEQ ID NO: 2).

FIG. 3 is an amino acid sequence of ovomucoid (SEQ ID NO: 3).

FIG. 4 is an amino acid sequence of G162M F167A ovomucoid (SEQ ID NO: 4).

FIG. 5 is an amino acid sequence of ovoglobulin G2 (SEQ ID NO: 5).

FIG. 6 is an amino acid sequence of ovoglobulin G3 (SEQ ID NO: 6).

FIG. 7 is an amino acid sequence of α-ovomucin (SEQ ID NO: 7).

FIG. 8 is a partial amino acid sequence of β-ovomucin (SEQ ID NO: 8).

FIG. 9 is an amino acid sequence of lysozyme (SEQ ID NO: 9).

FIG. 10 is an amino acid sequence of ovoinhibitor (SEQ ID NO: 10).

FIG. 11 is an amino acid sequence of cystatin (SEQ ID NO: 11).

FIG. 12 is an amino acid sequence of ovalbumin related protein X (SEQ ID NO: 12).

FIG. 13 is an amino acid sequence of ovalbumin related protein Y (SEQ ID NO: 13).

DETAILED DESCRIPTION OF THE INVENTION

Figure 14:
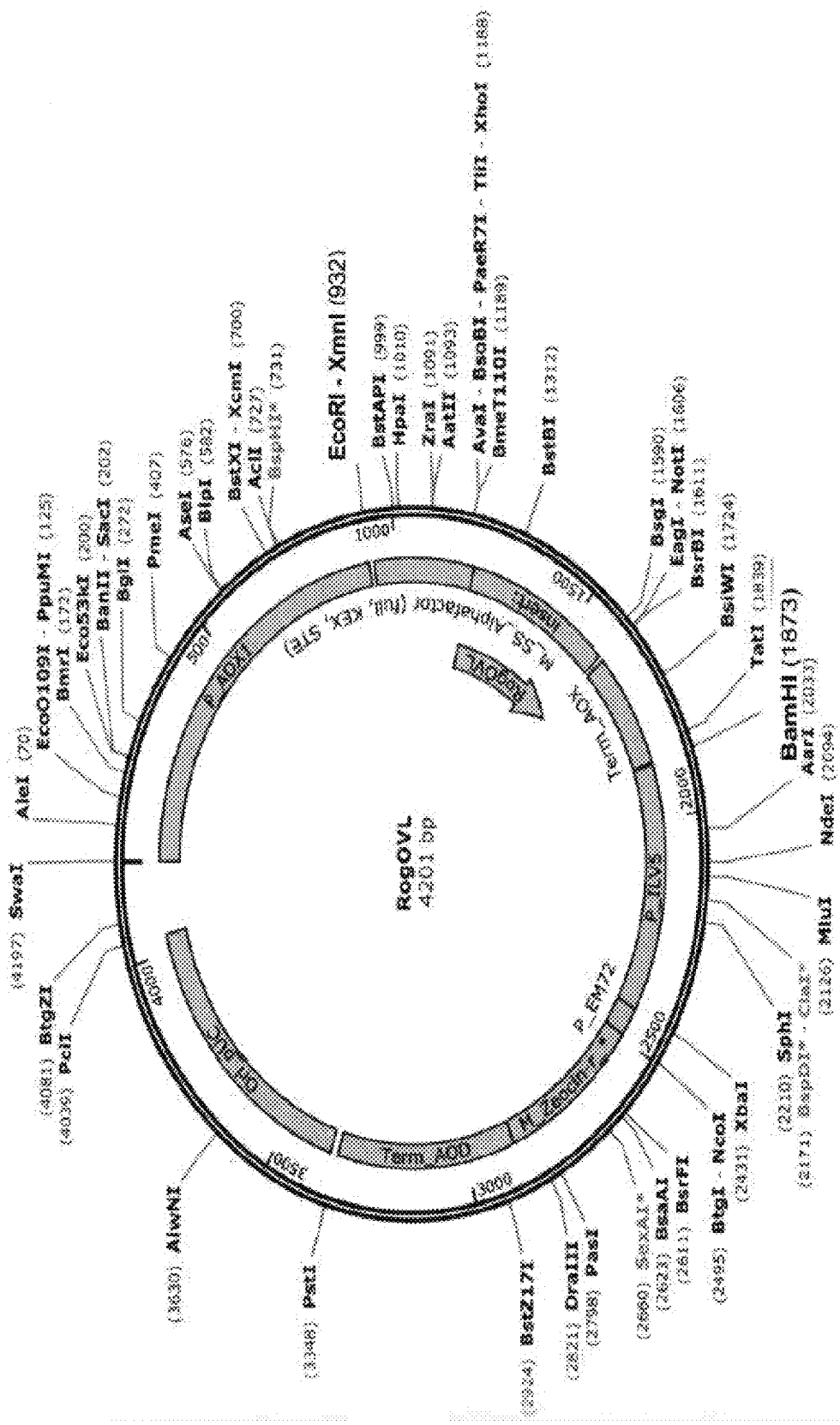
FIG. 14 shows a schematic diagram of an ovoglobulin expression vector, in accordance with examples.
Figure 15:
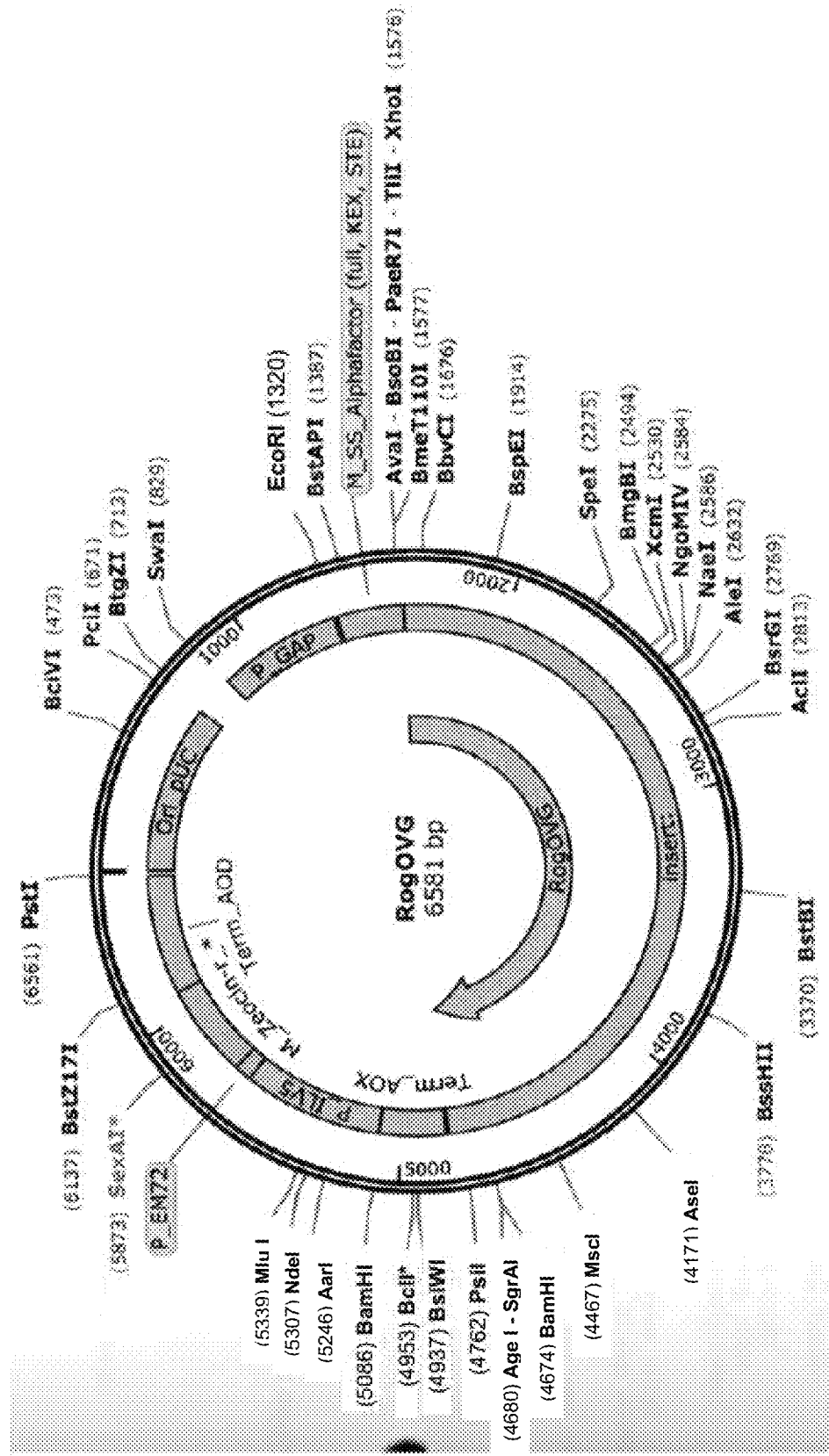
FIG. 15 shows a schematic diagram of a lysozyme expression vector, in accordance with examples.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 15%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide", "nucleotide", "nucleotide sequence", "nucleic acid", and "oligonucleotide" are used interchangeably. They refer to a polymeric form of nucleotides of any length, including deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, expression vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a detectable label.

"Expression" refers to the process by which a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide", and "protein" are used interchangeably herein to refer to polymers of amino acids of any length. The polymer may be linear or branched, may comprise modified amino acids, and may be interrupted by non amino acids. The terms also encompass an amino acid polymer that has been modified, for example, by disulfide bond formation, glycosylation, lipidation, acetylation, phosphorylation, or any other manipulation, such as conjugation with a detectable label.

As used herein the term "amino acid" includes natural and/or unnatural or synthetic amino acids, including glycine, cysteine, and both the D or L optical isomers, and amino acid analogs and peptidomimetics. In some embodiments, an amino acid is a proteinogenic, natural, standard, non-standard, non-canonical, essential, non-essential, or non-natural amino acid. In some embodiments, an amino acid has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, an amino acid has a nucleophilic or electrophilic side chain.

"Control" refers to an alternative subject or sample used in an experiment for comparison purpose. In some embodiments, a control comprises egg white from a chicken egg.

The terms "determining", "measuring", "evaluating", "assessing", "assaying", and "analyzing" can be used interchangeably herein to refer to any form of measurement, and include determining if an element is present or not (for example, detection). These terms can include both quantitative and/or qualitative determinations. Assessing may be relative or absolute. "Detecting the presence of can include determining the amount of something present and/or determining whether it is present or absent.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 96%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

Sequence identity, such as for the purpose of assessing percent complementarity, may be measured by any suitable alignment algorithm, including but not limited to the Needleman-Wunsch algorithm (see e.g., the EMBOSS Needle aligner available at The World Wide Web (at) ebi.ac.uk/Tools/psa/emboss_needle/nucleotide.html, optionally with default settings), the BLAST algorithm (see e.g., the BLAST alignment tool available at The World Wide Web (at) blast.ncbi.nlm.nih.gov/Blast.cgi, optionally with default settings), and the Smith-Waterman algorithm (see e.g., the EMBOSS Water aligner available at The World Wide Web (at) ebi.ac.uk/Tools/psa/emboss_water/nucleotide.html, optionally with default settings). Optimal alignment may be assessed using any suitable parameters of a chosen algorithm, including default parameters.

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (e.g., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 80% to 100% and integer values therebetween. Typically, the percent identities between a disclosed sequence and a claimed sequence are at least 80%, at least 85%, at least 90%, at least 95%, or at least 98%. In general, an exact match indicates 100% identity over the length of the reference sequence.

The term "effective amount" or "therapeutically effective amount" refers to that amount of a compound described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

The term "mammal" includes humans and both domestic animals such as laboratory animals and household pets (e.g., cats, dogs, swine, cattle, sheep, goats, horses, rabbits), and non-domestic animals such as wildlife and the like. Mammals include, but are not limited to, murines, simians, humans, farm animals, sport animals, domesticated animals, and pets. Tissues, cells, and their progeny of a biological entity obtained in vivo or cultured in vitro are also encompassed.

The term "bird" includes both domesticated birds and non-domesticated birds such as wildlife and the like. Birds include, but are not limited to, poultry, fowl, waterfowl, game bird, ratite (e.g., flightless bird), chicken (*Gallus gallus domesticus*), quail, turkey, duck, ostrich (*Struthio camelus*), Somali ostrich (*Struthio molybdophanes*), goose, gull, guineafowl, pheasant, emu (*Dromaius novaehollandiae*), American rhea (*Rhea americana*), Darwin's rhea (*Rhea pennata*), and kiwi. Tissues, cells, and their progeny of a biological entity obtained in vivo or cultured in vitro are also encompassed. A bird may lay eggs.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

In certain embodiments, the proteins or compounds disclosed herein are isotopically labeled. Isotopically-labeled proteins or compounds (e.g., an isotopologue) may have one or more atoms replaced by an atom having a different atomic mass or mass number. Non-limiting examples of isotopes that can be incorporated into the disclosed compounds include isotopes of hydrogen, carbon, nitrogen, oxygen, phosphorous, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}$-I, and $^{125}I$, respectively. Certain isotopically-labeled compounds, for example, those incorporating a stable isotope, are useful in mass spectrometry studies. For instance, a stable isotopic protein may be used as a reference standard in a mass spectrometry based assay. Certain isotopically-labeled compounds, for example, those incorporating a radioactive isotope, are useful in drug and/or substrate tissue distribution studies. The radioactive isotopes tritium ($^{3}H$) and carbon-14 ($^{14}C$) are particularly useful for this purpose in view of their ease of incorporation and ready means of detection. These radiolabeled compounds could be useful to help determine or measure the effectiveness of the compounds, by characterizing, for example, the site or mode of action, or binding affinity to a pharmacologically important site of action. Substitution with heavier isotopes such as deuterium ($^{2}H$) may afford certain therapeutic advantages resulting from greater metabolic stability, for example, increased in vivo half-life or reduced dosage requirements, and hence are preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds can generally be prepared by conventional techniques known to those skilled in the art or by processes analogous to those described herein using an appropriate isotopically-labeled reagent in place of the non-labeled reagent.

"Optional" and "optionally" mean that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

As used herein, the term "consumable product" refers to a product, which comprises an isolated recombinant egg white protein or egg white protein composition and other ingredients and may be consumed (e.g., by eating, chewing, drinking, tasting, ingesting, or swallowing). Consumable products include food products, beverage products, dietary supplements, food additives, pharmaceutical products, and hygiene products, as non-limiting examples. Food products include, but are not limited to, baked goods (e.g., cake, muffin, cookie, bread, bagel, pastry, doughnut), scramble, omelette, quiche, pasta, noodle, crepe, waffle, dough, batter, cookie dough, meatloaf, meatball, hamburger, animal feed, fruits, vegetables, tofu, bean curd, cheese, seafood, meat, ice cream, mayonnaise, custard, pudding, souffle, emulsion, foam, meringue, frosting, confectionery, marshmallow, marzipan, soup, condiments, sauces, spices, dairy products, and dressings. Beverage products include, but are not limited to, soft drink, flavored water, juice, sports drink, energy drink, smoothie, shake, alcoholic beverage (e.g., wine, sake, beer, spirits), cocktail, liqueur, carbonated beverage, caffeinated beverage, coffee, cocoa, tea, eggnog, and dairy drinks. Dietary supplements include multivitamins, whole food supplements, diet supplements, herbal supplement, protein blend, mass gainer, ready to drink protein, protein bar, protein shake, protein powder, protein shot, protein isolate, energy bar, energy gel, energy chew, energy formula, endurance formula, energy supplement, nutritional supplement, sports nutritional supplement, infant formula (e.g., powder or liquid), and meal replacement. Pharmaceutical products include, but are not limited to, cough syrups, capsules, and tablets. Hygiene products include, but are not limited to, cosmetics, skin care, beauty products, shampoo, conditioner, lotion, cream, face wash, tooth paste, chewing gum, and mouth wash.

Processing of a consumable product to form a processed consumable product may include, but is not limited to, freezing, chilling, heating, baking, roasting, broiling, boiling, blanching, packaging, canning, bleaching, enriching, drying, pressing, grinding, mixing, parcooking, cooking, proofing, marinating, cutting, slicing, dicing, crushing, shredding, chopping, shaking, coring, spiralizing, rolling, juicing, straining, filtering, kneading, whisking, beating, whipping, grating, stuffing, peeling, deseeding, smoking, curing, salting, preserving, pickling, fermenting, homogenizing, pasteurizing, sterilizing, stabilizing, blending, pureeing, fortifying, refining, hydrogenating, aging, extending shelf life, or adding enzymes.

As used herein, the term "solvent" refers to a liquid, which may be mixed with or used to dissolve a composition or one or more components of a composition such as a protein. Non-limiting examples of a solvent include water, ethanol, and isopropanol. The solvent can be potable. The solvent can be water. Non-limiting examples of water include purified water, distilled water, double distilled water, deionized water, distilled deionized water, drinking water, well water, tap water, spring water, bottled water, carbonated water, mineral water, flavored water, or any combination thereof. A solvent may be a combination of two or more distinct solvents.

Overview of Animal-Free Egg-White Production System

Provided herein are methods to produce protein components of egg white through recombinant expression in a host cell (e.g., yeast) and/or to purify egg white proteins from secretions of in vitro cultured oviduct cells. The purified proteins can be stored using established methods (e.g., spray drying), packaged as a powdered product, or sold in reconstituted form as an egg white protein composition that resembles animal-derived egg whites in consistency, taste, functional properties, and/or appearance. Different formulations of protein constituents of the egg white protein composition can be achieved as the absence or abundance of individual constituents can be adjusted independently. In one embodiment, ovomucoid, a major food allergen in egg white that can cause immediate food-hypersensitivity in children, can be eliminated in the final formulation, or modified genetically and/or glycosylated to produce a reduced allergenicity egg white product.

Bird eggs are a common food source and a versatile ingredient in cooking. Eggs generally contain an eggshell, membrane, egg white, and egg yolk. The egg white or albumen contains approximately 10% proteins, 88% water, and 1-2% carbohydrates, minerals, and lipids. Egg white proteins may include, but are not limited to, ovalbumin (~54%), ovotransferrin or conalbumin (~12%), ovomucoid (~11%), ovoglobulin G2 (~4%), ovoglobulin G3 (~4%), ovomucin (~3.5%), lysozyme (~3.4%), ovoinhibitor (~1.5%), ovoglycoprotein (~1.0%), flavoprotein or ovoflavoprotein (~0.8%), ovomacroglobulin (~0.5%), cystatin (~0.05%), avidin (~0.05%), ovostatin, ovalbumin related protein X, ovalbumin related protein Y, tenp, clusterin, CH21, VMO-1, vitellogenin, zona pellucida C protein, ovotransferrin BC type, ovoinhibitor precursor, ovomucoid precursor, clusterin precursor, Hep21 protein precursor, ovoglycoprotein precursor, extracellular fatty acid-binding protein, extracellular fatty acid-binding protein precursor, prostaglandin D2 synthase brain precursor, marker protein, vitellogenin-1, vitellogenin-2, vitellogenin-2 precursor, vitellogenin-3, riboflavin binding protein, hemopexin, serum albumin precursor, apolipoprotein D, ovosecretoglobulin, Hep21, glutathione peroxidase 3, lipocalin-type prostaglandin D synthase/chondrogenesis-associated lipocalin, apovitellenin-1, dickkopf-related protein 3, gallinacin-11 (VMO-II, β-defensin-11), serum albumin (α-livetin), gallin, secretory trypsin inhibitor, lymphocyte antigen 86, actin, Ig μ chain C region, sulfhydryl oxidase 1, histone H4, angiopoietin-like protein 3, ubiquitin, ovocalyxin-32, polymeric immunoglobulin receptor, peptidyl-prolyl-cis/trans isomerase B, aminopeptidase Ey, pleiotrophin, midkine, renin/prorenin receptor, TIMP-2, TIMP-3, histone H2B variants, Ig λ chain, FAMC3 protein, α-enolase, 60S acidic ribosomal protein P1, cytotactinitenascin, CEPU-1, selenoprotein, elongation factor 1-α 1, epididymal secretory protein, El, 14-3-3 Protein ξ (zeta), olfactomedin-like protein 3, glutathione S-transferase 2, β-2-microglobulin, RGD-CAP, apolipoprotein B, golgi apparatus protein 1, cochlin, proteasome subunit α type-7, apolipoprotein A-I, eukaryotic initiation factor 4A-II, ASPIC/cartilage acidic protein 1, triosephosphate isomerase, proteasome subunit α-type, Ig λ chain C-region, procollagen-lysine 2-oxoglutarate 5-dioxgenase 1, ADP-ribosylation factor 5, calmodulin, protein disulfide-isomerase, annexin I, elongation factor 2, peroxiredoxin-1, HSP70, protein disulfide isomerase A3, calreticulin, 40S ribosomal protein SA/laminin receptor 1, α-Actinin-4, tumor necrosis factor-related apoptosis-inducing ligand, vitamin D-binding protein, semaphorin-3C, endoplasmin, catalase, hepatic α-amylase, transitional ER ATPase, cadherin-1, angiotensin-converting enzyme, bone morphogenetic protein 1, guanine nucleotide-binding protein subunit β2-like 1, histidine ammonia lyase, annexin A2, β-catenin, RAB-GDP dissociation inhibitor, lamin-A, ovocleidin-116, aminopeptidase, HSP90-α, hypoxia up-regulated protein 1, heat shock cognate protein HSP90 β, ATP-citrate synthase, and myosin-9.

In one aspect, the present disclosure provides a method of producing an egg white protein composition, the method comprising: recombinantly expressing two or more egg white proteins; and mixing the two or more egg white proteins. In some cases, the egg white proteins are selected from the group consisting of ovalbumin, ovotransferrin, ovomucoid, G162M Fl 67A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof. The recombinantly expressing the two or more egg white proteins may occur in one or more host cells. The method may further comprise secreting the two or more egg white proteins from the one or more host cells. The recombinantly expressing the two or more egg white proteins may occur using cell-free protein synthesis. The method may further comprise adding a food additive to the egg white protein composition. The method may further comprise desugaring, stabilizing, or removing glucose from the egg white protein composition. The method may further comprise pasteurizing or ultrapasteurizing the egg white protein composition. The method may further comprise drying the egg white protein composition. The method may further comprise enzymatically, chemically, or mechanically digesting one or more of the two or more egg white proteins. Treatment of one or more of the egg white proteins may improve functional properties of the composition, for example, providing enhanced foaming or solubility.

In one aspect, the present disclosure provides a processed consumable product comprising one or more recombinant egg white proteins or fragments thereof. In some cases, the one or more egg white proteins are selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof. In some cases, the processed consumable product comprises two or more, three or more, four or more, five or more, or six or more egg white proteins or fragments thereof. In some cases, the processed consumable product lacks one or more, two or more, three or more, five or more, ten or more, twenty or more, or fifty or more egg white proteins. The processed consumable product may lack ovomucoid. In some cases, the processed consumable product may lack one or more, two or more, three or more, five or more, ten or more, or twenty or more egg yolk proteins. In some cases, the processed consumable product is selected from the group consisting of food product, beverage product, dietary supplement, food additive, pharmaceutical product, hygiene product, and any combination thereof, such as from the group consisting of food product, beverage product, and any combination thereof.

In one aspect, the present disclosure provides a method of producing a consumable product, the method comprising: recombinantly expressing one or more egg white proteins; and mixing the one or more egg white proteins with one or more ingredients to produce a consumable product. In some cases, the one or more ingredients comprise food additives, egg white proteins, or recombinant egg white proteins. In some cases, the one or more ingredients do not comprise egg white proteins. In some cases, the one or more egg white proteins may comprise two or more, three or more, four or more, or five or more egg white proteins.

In one aspect, the present disclosure provides a method for producing an egg white protein or fragment thereof, the method comprising: recombinantly expressing the egg white protein or fragment thereof in a host cell, wherein the host cell comprises a polynucleotide encoding the egg white protein or fragment thereof, and wherein the egg white protein is selected from the group consisting of ovoglobulin G2, ovoglobulin G3, α-ovomucin, β-ovomucin, ovoglycoprotein, flavoprotein, ovomacroglobulin, cystatin, and any combination thereof, such as from the group consisting of ovoglobulin G2, ovoglobulin G3, ovoglycoprotein, flavoprotein, ovomacroglobulin, cystatin, and any combination thereof. The method may further comprise secreting the egg white protein or fragment thereof from the host cell. The method may further comprise purifying the egg white protein or fragment thereof. The method may further comprise recombinantly expressing a second egg white protein or fragment thereof in the host cell. In some cases, the fragment comprises at least 10%, 20%, 30%, 40%, or 50% of the egg white protein.

In some cases, a fragment of a protein may be about or at least 10, 50, 100, 200, 300, 400, 500, 600, 700, 800, 900, 1000, 1100, 1200, 1300, 1400, 1500, 1600, 1700, 1800, 1900, or 2000 amino acids in length. In some cases, a fragment of a protein may be up to 10, 50, 100, 200, 300, 400, 500, 600, 700, 800, 900, 1000, 1100, 1200, 1300, 1400, 1500, 1600, 1700, 1800, 1900, or 2000 amino acids in length.

In some cases, a fragment of a protein may be about or at least 1%, 5%, 10%, 15%, 20%, 25%, 30%, 35%, 40%, 45%, 50%, 55%, 60%, 65%, 70%, 75%, 80%, 85%, 90%, 95%, or 100% of the protein. In some cases, a fragment of a protein may be up to 1%, 5%, 10%, 15%, 20%, 25%, 30%, 35%, 40%, 45%, 50%, 55%, 60%, 65%, 70%, 75%, 80%, 85%, 90%, 95%, or 100% of the protein. In some cases, a fragment of a protein may be about or at least 10, 50, 100, 200, 300, 400, 500, 600, 700, 800, 900, or 1000 kDa. In some cases, a fragment of a protein may be up to 10, 50, 100, 200, 300, 400, 500, 600, 700, 800, 900, or 1000 kDa.

In one aspect, the present disclosure provides a method for producing two or more egg white proteins or fragments thereof, the method comprising recombinantly expressing the two or more egg white proteins or fragments thereof in a host cell. The host cell may comprise one or more polynucleotides encoding the two or more egg white proteins or fragments thereof. The method may further comprise secreting the two or more egg white proteins or fragments thereof from the host cell. The method may further comprise purifying the two or more egg white proteins or fragments thereof. In some cases, the two or more egg white proteins are selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof.

In one aspect, the present disclosure provides an isolated recombinant egg white protein selected from the group consisting of ovoglobulin G2, ovoglobulin G3, α-ovomucin, β-ovomucin, ovoglycoprotein, flavoprotein, ovomacroglobulin, cystatin, and any combination thereof, such as from the group consisting of ovoglobulin G2, ovoglobulin G3, ovoglycoprotein, flavoprotein, ovomacroglobulin, cystatin, and any combination thereof. The isolated recombinant egg white protein may have a glycosylation, acetylation, or phosphorylation pattern different from the egg white protein in an egg white. The isolated recombinant egg white protein may have a melting temperature different from the egg white protein in an egg white, such as a higher or lower melting temperature relative to the egg white protein in an egg white. In some cases, the isolated recombinant egg white protein has a melting temperature of about or at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some cases, the isolated recombinant egg white protein has a melting temperature of up to 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some cases, the isolated recombinant egg white protein may comprise one or more amino acid insertions, deletions, or substitutions relative to the egg white protein in an egg white. In some cases, an isolated recombinant egg white protein may have about or at least 0, 1, 2, 3, 4, 5, 6, 7, 8, 9, 10, 15, 20, 25, 30, 40, 50, 60, 70, 80, 90, 100, 150, 200, 250, 300, 350, 400, 450, 500, 600, 700, 800, 900, or 1000 amino acid insertions, deletions, and/or substitutions relative to the egg white protein in an egg white. In some cases, an isolated recombinant egg white protein may have up to 0, 1, 2, 3, 4, 5, 6, 7, 8, 9, 10, 15, 20, 25, 30, 40, 50, 60, 70, 80, 90, 100, 150, 200, 250, 300, 350, 400, 450, 500, 600, 700, 800, 900, or 1000 amino acid insertions, deletions, and/or substitutions relative to the egg white protein in an egg white. In some cases, the isolated recombinant egg white protein is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and any combination thereof.

In one aspect, the present disclosure provides an isolated mutant ovomucoid, comprising tryptophan. The isolated mutant ovomucoid may be recombinantly expressed. The isolated mutant ovomucoid may be a complete protein. In some cases, the isolated mutant ovomucoid comprises one or more, two or more, three or more, four or more, five or more, or six or more amino acid insertions or substitutions relative to SEQ ID: NO: 3 when optimally aligned. In some cases, the isolated mutant ovomucoid comprises one or more amino acid substitutions, wherein the amino acid substitutions comprise one or more, two or more, three or more, four or more, five or more, or six or more tyrosine to tryptophan substitutions (e.g., at position 37, 46, 73, 102, 141, or 161 relative to SEQ ID NO: 3 or SEQ ID NO: 4 when optimally aligned). In some cases, the isolated mutant ovomucoid comprises up to four, five, six, or ten amino acid insertions or substitutions relative to SEQ ID: NO: 3 when optimally aligned. In some cases, the isolated mutant ovomucoid comprises one or more, two or more, three or more, or four or more tryptophan residues. In some cases, the isolated mutant ovomucoid comprises one or more, two or more, three or more, or four or more tryptophan residues at the N-terminus or C-terminus. The isolated mutant ovomucoid may comprise a methionine at position 162 and an alanine at position 167 relative to SEQ ID NO: 3 when optimally aligned.

The isolated mutant ovomucoid may have reduced allergenicity relative to wild-type ovomucoid. In some cases, an isolated mutant ovomucoid has an allergenicity of about or at least 0%, 1%, 5%, 10%, 15%, 20%, 25%, 30%, 35%, 40%, 45%, 50%, 55%, 60%, 65%, 70%, 75%, 80%, 85%, 90%, or 95% relative to wild-type ovomucoid. In some cases, an isolated mutant ovomucoid has an allergenicity of up to 0%, 1%, 5%, 10%, 15%, 20%, 25%, 30%, 35%, 40%, 45%, 50%, 55%, 60%, 65%, 70%, 75%, 80%, 85%, 90%, or 95% relative to wild-type ovomucoid. In some cases, reduced allergenicity may be measured using a skin prick test, blood test, or oral food challenge.

The isolated mutant ovomucoid may have enhanced digestibility relative to wild-type ovomucoid. In some cases, an isolated mutant ovomucoid has a digestibility of about or at least 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to wild-type ovomucoid. In some cases, an isolated mutant ovomucoid has a digestibility of up to 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to wild-type ovomucoid. In some cases, enhanced digestibility may be measured as a rate of protein metabolism or rate of degradation or digestion by a protease or an acid, in vivo or in vitro.

An isolated mutant ovomucoid may have a glycosylation, acetylation, or phosphorylation pattern different from a wild-type ovomucoid. An isolated mutant ovomucoid may have a melting temperature different from a wild-type ovomucoid. An isolated mutant ovomucoid may comprise one or more amino acid insertions, deletions, or substitutions relative to a wild-type ovomucoid. In some cases, an isolated mutant ovomucoid may have about or at least 0, 1, 2, 3, 4, 5, 6, 7, 8, 9, 10, 11, 12, 13, 14, 15, 16, 17, 18, 19, 20, 25, 30, 40, 50, 60, 70, 80, 90, or 100, amino acid insertions, deletions, and/or substitutions relative to a wild-type ovomucoid. In some cases, an isolated mutant ovomucoid may have up to 0, 1, 2, 3, 4, 5, 6, 7, 8, 9, 10, 11, 12, 13, 14, 15, 16, 17, 18, 19, 20, 25, 30, 40, 50, 60, 70, 80, 90, or 100 amino acid insertions, deletions, and/or substitutions relative to a wild-type ovomucoid.

In one aspect, the present disclosure provides an egg white protein composition comprising: an isolated recombinant egg white protein or an isolated mutant ovomucoid described herein; and one or more egg white proteins. The one or more egg white proteins may be recombinantly expressed.

In one aspect, the present disclosure provides an egg white protein composition comprising two or more recombinant egg white proteins. In some cases, the two or more recombinant egg white proteins are selected from the group consisting of ovalbumin, ovotransferrin, ovomucoid, G162M F167A ovomucoid, ovoglobulin G2, ovoglobulin G3, α-ovomucin, β-ovomucin, lysozyme, ovoinhibitor, ovoglycoprotein, flavoprotein, ovomacroglobulin, ovostatin, cystatin, avidin, ovalbumin related protein X, ovalbumin related protein Y, and any combination thereof, such as from the group consisting of ovalbumin, ovotransferrin, ovomucoid, G162M F167A ovomucoid, ovoglobulin G2, ovoglobulin G3, lysozyme, ovoinhibitor, ovoglycoprotein, flavoprotein, ovomacroglobulin, ovostatin, cystatin, avidin, ovalbumin related protein X, ovalbumin related protein Y, and any combination thereof. The egg white protein composition may comprise ovalbumin. The egg white protein composition may comprise an isolated recombinant egg white protein described herein. The egg white protein composition may comprise an isolated mutant ovomucoid described herein.

The egg white proteins may have sequences derived from a single species, such as from *Gallus gallus domesticus*. In some cases, the single species is not *Gallus gallus domesticus*. The egg white proteins may have sequences derived from more than one species. In some cases, the egg white proteins have sequences derived from a bird selected from the group consisting of poultry, fowl, waterfowl, game bird, chicken, quail, turkey, duck, ostrich, goose, gull, guineafowl, pheasant, emu, and any combination thereof. In some cases, the egg white protein composition comprises three or more, four or more, or five or more or more egg white proteins. In some cases, the egg white protein composition comprises up to 5, 10, 15, or 20 egg white proteins. An egg white protein composition may comprise an isolated mutant ovomucoid disclosed herein.

In some cases, a recombinant egg white protein may comprise one or more amino acid insertions, deletions, or substitutions relative to the egg white protein in an egg white. In some cases, a recombinant egg white protein may have about or at least 0, 1, 2, 3, 4, 5, 6, 7, 8, 9, 10, 15, 20, 25, 30, 40, 50, 60, 70, 80, 90, 100, 150, 200, 250, 300, 350, 400, 450, 500, 600, 700, 800, 900, or 1000 amino acid insertions, deletions, and/or substitutions relative to the egg white protein in an egg white. In some cases, a recombinant egg white protein may have up to 0, 1, 2, 3, 4, 5, 6, 7, 8, 9, 10, 15, 20, 25, 30, 40, 50, 60, 70, 80, 90, 100, 150, 200, 250, 300, 350, 400, 450, 500, 600, 700, 800, 900, or 1000 amino acid insertions, deletions, and/or substitutions relative to the egg white protein in an egg white. For instance, a recombinant lysozyme may have an amino acid substitution (e.g., replacement of tryptophan with tyrosine) at position 62 relative to SEQ ID NO: 9 when optimally aligned.

The egg white protein composition may further comprise water. In some cases, the egg white protein composition has a percentage of water up to 5%, 10%, 15%, 20%, 25%, 30%, 35%, 40%, 45%, 50%, 55%, 60%, 65%, 70%, 75%, 80%, 85%, 90%, or 95%. In some cases, the egg white protein composition has a percentage of water within the range from 80% to 95%. In some cases, the egg white protein composition comprises at least 50%, 60%, 70%, 80%, 90%, 95%, or 99% protein by dry weight. The egg white protein composition may further comprise a food additive. In some cases, the food additive is selected from the group consisting of a sweetener, salt, carbohydrate, and any combination thereof.

The egg white protein composition may lack cholesterol. In some cases, the egg white protein composition comprises less than 10%, 5%, 4%, 3%, 2%, 1%, or 0.5% fat by dry weight. The egg white protein composition may lack fat, saturated fat, or trans fat. The egg white protein composition may lack glucose. The egg white protein composition may lack one or more egg white proteins such as ovomucoid or flavoprotein. For instance, ovomucoid is an egg white allergen, and its absence in an egg white protein composition may reduce the allergenicity of the egg white protein composition. As another example, flavoprotein may provide a yellow tinge to egg white, and its absence in an egg white protein composition may whiten the egg white protein composition or yield a brighter white color in products made with the egg white protein composition such as a meringue relative to natural egg whites. In some cases, the egg white protein composition lacks two or more, three or more, five or more, ten or more, twenty or more, or fifty or more egg white proteins. In some cases, the egg white protein composition is not an egg, egg white, or egg yolk.

In some cases, the egg white protein composition is acidic, neutral, or basic. In some cases, pH is about or at least 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10. In some cases, pH is up to 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10. In some cases, the egg white protein composition may have a pH within the range from 6 to 10.

An egg white protein composition may have a foam height greater than a foam height of an egg white. In some cases, the egg white protein composition has a foam height within the range from 10 mm to 60 mm, such as from 30 mm to 60 mm. In some cases, an egg white protein composition has a foam height of about or at least 1, 5, 10, 15, 20, 25, 26, 27, 28, 29, 30, 31, 32, 33, 34, 35, 36, 37, 38, 39, 40, 41, 42, 43, 44, 45, 50, 55, or 60 mm. In some cases, an egg white protein composition has a foam height of up to 1, 5, 10, 15, 20, 25, 26, 27, 28, 29, 30, 31, 32, 33, 34, 35, 36, 37, 38, 39, 40, 41, 42, 43, 44, 45, 50, 55, or 60 mm. In some cases, an egg white protein composition has a foam height of about or at least 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white. In some cases, an egg white protein composition has a foam height of up to 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white.

An egg white protein composition may have a foam seep less than a foam seep of an egg white (e.g., at 30 minutes after whipping). In some cases, the egg white protein composition may have a foam seep up to 10 mm or up to 5 mm (e.g., at 30 minutes after whipping). In some cases, an egg white protein composition has a foam seep of about or at least 0, 1, 2, 3, 4, 5, 6, 7, 8, 9, 10, 11, 12, 13, 14, 15, 20, 25, or 30 mm. In some cases, an egg white protein composition has a foam seep of up to 0, 1, 2, 3, 4, 5, 6, 7, 8, 9, 10, 11, 12, 13, 14, 15, 20, 25, or 30 mm. In some cases, foam seep is measured at 1 min, 5 min, 10 min, 15 min, 20 min, 30 min, 40 min, 50 min, 1 h, 2 h, 3 h, 4 h, 5 h, 6 h, 7 h, 8 h, 9 h, 10 h, 15 h, 20 h, 24 h, 25 h, 30 h, or more than 30 h after whipping. In some cases, an egg white protein composition has a foam seep of about or at least 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white. In some cases, an egg white protein composition has a foam seep of up to 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white.

An egg white protein composition may have a foam strength greater than a foam strength of an egg white. In some cases, the egg white protein composition may have a foam strength within the range from 30 g to 100 g, such as within the range from 40 g to 100 g. In some cases, an egg white protein composition has a foam strength of about or at least 5, 10, 20, 30, 35, 40, 45, 50, 55, 60, 65, 70, 75, 80, 90, 100, 110, 120, 130, 140, 150, or 200 g. In some cases, an egg white protein composition has a foam strength of up to 5, 10, 20, 30, 35, 40, 45, 50, 55, 60, 65, 70, 75, 80, 90, 100, 110, 120, 130, 140, 150, or 200 g. In some cases, an egg white protein composition has a foam strength of about or at least 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white. In some cases, an egg white protein composition has a foam strength of up to 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white.

An egg white protein composition may have a gel strength greater than a gel strength of an egg white. In some cases, the egg white protein composition may have a gel strength within the range from 100 g to 1500 g, from 500 g to 1500 g, or from 700 g to 1500 g. In some cases, an egg white protein composition has a gel strength of about or at least 10, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 g. In some cases, an egg white protein composition has a gel strength of up to 10, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 g. In some cases, an egg white protein composition has a gel strength of about or at least 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white. In some cases, an egg white protein composition has a gel strength of up to 0%, 1%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 210%, 220%, 230%, 240%, 250%, 260%, 270%, 280%, 290%, 300%, 350%, 400%, 450%, or 500% relative to an egg white.

In some cases, the egg white protein composition may have a shelf life of at least one, two, three, or six months.

An egg white protein composition may have reduced allergenicity relative to an egg white. Reduced allergenicity may be achieved, for instance, through removal of one or more egg white proteins (e.g., ovomucoid, ovalbumin, ovotransferrin, lysozyme) or removal or mutation (e.g., one or more amino acid insertions, deletions, and/or substitutions) of one or more allergenic sites or domains within an egg white protein. In some cases, an egg white protein composition has an allergenicity of about or at least 0%, 1%, 5%, 10%, 15%, 20%, 25%, 30%, 35%, 40%, 45%, 50%, 55%, 60%, 65%, 70%, 75%, 80%, 85%, 90%, or 95% relative to an egg white. In some cases, an egg white protein composition has an allergenicity of up to 0%, 1%, 5%, 10%, 15%, 20%, 25%, 30%, 35%, 40%, 45%, 50%, 55%, 60%, 65%, 70%, 75%, 80%, 85%, 90%, or 95% relative to an egg white. In some cases, reduced allergenicity may be measured using a skin prick test, blood test, or oral food challenge.

An egg white protein composition may be formulated as a liquid, solid, or powder. An egg white protein composition may be refrigerated or frozen.

In one aspect, the present disclosure provides a polynucleotide encoding an isolated recombinant egg white protein or isolated mutant ovomucoid described herein. A polynucleotide may be codon optimized. A polynucleotide may be DNA or RNA.

A polynucleotide described herein can be obtained using chemical synthesis, molecular cloning or recombinant methods, DNA or gene assembly methods, artificial gene synthesis, PCR, or any combination thereof. Methods of chemical polynucleotide synthesis are well known in the art and need not be described in detail herein. One of skill in the art can use the sequences provided herein and a commercial DNA synthesizer to produce a desired DNA sequence. For preparing polynucleotides using recombinant methods, a polynucleotide comprising a desired sequence can be inserted into a suitable cloning or expression vector, and the cloning or expression vector in turn can be introduced into a suitable host cell for replication and amplification, as further discussed herein. Polynucleotides may be inserted into host cells by any means known in the art. Cells may be transformed by introducing an exogenous polynucleotide, for example, by direct uptake, endocytosis, transfection, F-mating, PEG-mediated protoplast fusion, *Agrobacterium tumefaciens*-mediated transformation, biolistic transformation, chemical transformation, or electroporation. Once introduced, the exogenous polynucleotide can be maintained within the cell as a non-integrated expression vector (such as a plasmid) or integrated into the host cell genome. The polynucleotide so amplified can be isolated from the host cell by methods well known within the art. Alternatively, nucleic acid amplification methods (e.g., PCR) allow reproduction of DNA sequences.

RNA can be obtained by using the isolated DNA in an appropriate expression vector and inserting it into a suitable host cell. When the cell replicates and the DNA is transcribed into RNA, the RNA can then be isolated using methods well known to those of skill in the art. Alternatively, RNA can be obtained by transcribing the isolated DNA, for example, by an in vitro transcription reaction using an RNA polymerase. Alternatively, RNA can be obtained using chemical synthesis.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the expression vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

A polynucleotide described herein may further encode a signal peptide. A signal peptide, also known as a signal sequence, targeting signal, localization signal, localization sequence, secretion signal, transit peptide, leader sequence, or leader peptide, may support secretion of a protein or polynucleotide. Extracellular secretion of a recombinant or heterologously expressed protein from a host cell may facilitate protein purification. For example, recovery of a recombinant protein from a cell culture supernatant may be preferable to lysing host cells to release a complex mixture of proteins including intracellular proteins of the host cell. Secretion may reduce deleterious effects that intracellular overexpression of a heterologous protein may have on a host cell such as toxicity or decreased growth rate. Secretion may allow increased protein production compared to intracellular expression in a host cell of limited volume to store the synthesized proteins. Secretory production of a protein may facilitate post-translational modification or processing (e.g., protein folding, formation of disulfide bonds, glycosylation).

A secreted protein may initially be expressed as a precursor with an N-terminal signal peptide. A signal peptide may contain a positively charged N-terminus of 1-5 residues (n-region), a central hydrophobic core of 6-16 amino acids (h-region), and a polar region of 3-7 amino acids that is a recognition site for a signal peptidase (c-region). A signal peptide may be located at the N-terminus of a preprotein that is destined for secretion out of the cell. In some cases, e.g., chicken ovalbumin and human plasminogen activator, a signal peptide is internal. A signal peptide may be 15 to 50 amino acids in length.

A signal peptide may direct the expressed precursor preprotein across the membrane of the endoplasmic reticulum. A signal peptide may be cleaved off from the rest of the protein by a signal peptidase, for example, during translocation or shortly after completion of translocation. A protein may be transported to the Golgi apparatus and secreted unless it carries a signal for retention in intracellular compartments.

A signal peptide may be located at the N-terminus of an egg white protein or mutant ovomucoid.

A signal peptide may be derived from a precursor (e.g., prepropeptide, preprotein) of a protein. Signal peptides may be derived from a precursor of a protein including, but not limited to, acid phosphatase (e.g., *Pichia pastoris* PHO1), albumin (e.g., chicken), alkaline extracellular protease (e.g., *Yarrowia lipolytica* XRP2), α-mating factor (α-MF, MAT α) (e.g., *Saccharomyces cerevisiae*), amylase (e.g., α-amylase, *Rhizopus oryzae*, *Schizosaccharomyces pombe* putative amylase SPCC63.02c (Amyl)), β-casein (e.g., bovine), carbohydrate binding module family 21 (CBM21)-starch binding domain, carboxypeptidase Y (e.g., *Schizosaccharomyces pombe* Cpyl), cellobiohydrolase I (e.g., *Trichoderma reesei* CBH1), dipeptidyl protease (e.g., *Schizosaccharomyces pombe* putative dipeptidyl protease SPBC1711.12 (Dppl)), glucoamylase (e.g., *Aspergillus awamori*), heat shock protein (e.g., bacterial Hsp70), hydrophobin (e.g., *Trichoderma reesei* HBFI, *Trichoderma reesei* HBFII), inulase, invertase *Saccharomyces cerevisiae* SUC2), killer protein or killer toxin (e.g., 128 kDa pGKL killer protein, α-subunit of the K1 killer toxin (e.g., *Kluyveromyces lactic*), K1 toxin KILM1, K28 pre-pro-toxin, *Pichia acaciae*), leucine-rich artificial signal peptide CLY-L8, lysozyme (e.g., chicken CLY), phytohemagglutinin (PHA-E) (e.g., *Phaseolus vulgaris*), maltose binding protein (MBP) (e.g., *Escherichia coli*), P-factor (e.g., *Schizosaccharomyces pombe* P3), *Pichia pastoris* Dse, *Pichia pastoris* Exg, *Pichia pastoris* Pir 1, *Pichia pastoris* Scw, and cell wall protein Pir4 (protein with internal repeats). A signal peptide may comprise a sequence in Table 1. In some cases, a signal peptide may be selected from the group consisting of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, and SEQ ID NOS 72-86 and any combination thereof.

In some cases, a signal peptide is about or at least 5, 10, 15, 20, 25, 30, 50, or 100 amino acids in length. In some cases, a signal peptide is up to 5, 10, 15, 20, 25, 30, 50, or 100 amino acids in length. In some cases, a signal peptide may be within the range from 5 to 50 amino acids in length or within the range from 5 to 30 amino acids in length.

A signal peptide may be modified or comprise one or more amino acid insertions, deletions, and/or substitutions, for instance, using codon optimization, directed evolution, insertion of spacers, and/or deletion mutagenesis.

A polynucleotide may further encode a signal peptidase cleavage or recognition site. A signal peptidase includes, but is not limited to, KEX2, Krpl, Enterokinase (EKT), thrombin, factor Xa (FXa), Tobacco Etch Virus (TEV), and 3C Prescission.

TABLE 1

| | Sequences of exemplary signal peptides |
|---|---|
| SEQ ID NO: 14 | MQVKSIVNLLLACSLAVA |
| SEQ ID NO: 15 | MQFNWNIKTVASILSALTLAQA |
| SEQ ID NO: 16 and 72 | MYRNLIIATALTCGAYS...AYVPSEPWSTLTPDASLESALKDYSQTF GIAIKSLDADKIKR |
| SEQ ID NO: 17 and 73 | MNLYLITLLFASLCSA...ITLPKR |
| SEQ ID NO: 18 | MFEKSKFVVSFLLLLQLFCVLGVHG |
| SEQ ID NO: 19 | MQFNSVVISQLLLTLASVSMG |
| SEQ ID NO: 20 and 74 | MKSQLIFMALASLVAS...APLEHQQQHHKHEKR |
| SEQ ID NO: 21 | MKFAISTLLIILQAAAVFA |
| SEQ ID NO: 22 | MKLLNFLLSFVTLFGLLSGSVFA |
| SEQ ID NO: 23 | MIFNLKTLAAVAISISQVSA |
| SEQ ID NO: 24 and 75 | MKISALTACAVTLAGLAIA...APAPKPEDCTTTVQKRHQHKR |
| SEQ ID NO: 25 | MSYLKISALLSVLSVALA |
| SEQ ID NO: 26 | MLSTILNIFILLLFIQASLQ |
| SEQ ID NO: 27 and 76 | MKLSTNLILAIAAASAVVSA...APVAPAEEAANHLHKR |
| SEQ ID NO: 28 | MFKSLCMLIGSCLLSSVLA |

TABLE 1-continued

Sequences of exemplary signal peptides

| SEQ ID NO: 29 | MKLAALSTIALTILPVALA |
|---|---|
| SEQ ID NO: 30 | MSFSSNVPQLFLLLVLLTNIVSG |
| SEQ ID NO: 31 and 77 | MQLQYLAVLCALLLNVQS...KNVVDFSRFGDAKISPDDTDLESRER KR |
| SEQ ID NO: 32 | MKIHSLLLWNLFFIPSILG |
| SEQ ID NO: 33 | MSTLTLLAVLLSLQNSALA |
| SEQ ID NO: 34 and 78 | MINLNSFLILTVTLLSPALA...LPKNVLEEQQAKDDLAKR |
| SEQ ID NO: 35 | MFSLAVGALLLTQAFG |
| SEQ ID NO: 36 | MKILSALLLLFTLAFA |
| SEQ ID NO: 37 | MKVSTTKFLAVFLLVRLVCA |
| SEQ ID NO: 38 | MQFGKVLFAISALAVTALG |
| SEQ ID NO: 39 | MWSLFISGLLTYPLVLG |
| SEQ ID NO: 40 | MRNHLNDLVVLFLLLTVAAQA |
| SEQ ID NO: 41 | MFLKSLLSFASILTLCKA |
| SEQ ID NO: 42 | MFVFEPVLLAVLVASTCVTA |
| SEQ ID NO: 43 | MVSLRSIFTSSILAAGLTRAHG |
| SEQ ID NO: 44 | MFSPILSLEIILALATLQSVFA |
| SEQ ID NO: 45 | MIINHLVLTALSIALA |
| SEQ ID NO: 46 | MLALVRISTLLLLALTASA |
| SEQ ID NO: 47 | MRPVLSLLLLLASSVLA |
| SEQ ID NO: 48 | MVLIQNFLPLFAYTLFFNQRAALA |
| SEQ ID NO: 49 | MKFPVPLLFLLQLFFIIATQG |
| SEQ ID NO: 50 | MVSLTRLLITGIATALQVNA |
| SEQ ID NO: 51 | e base of the beaker to t |
| SEQ ID NO: 52 | MVLVGLLTRLVPLVLLAGTVLLLVFVVLSGG |
| SEQ ID NO: 53 | MLSILSALTLLGLSCA |
| SEQ ID NO: 54 | MRLLHISLLSIISVLTKANA |
| SEQ ID NO: 55, 79, and 80 | MRFPSTTAVLFAASSALA...APVNTTTEDETAQIPAEAVIGYLDLEG DFDVAVLPFSNSTNNGLLFINTTIASIAAKEEGVSLDKR...EAEA |
| SEQ ID NO: 56 | MFKSVVYSILAASLANA |
| SEQ ID NO: 57 | MLLQAFLFLLAGFAAKISA |
| SEQ ID NO: 58 | MASSNLLSLALFLVLLTHANS |
| SEQ ID NO: 59 and 81 | MNIFYIFLFLLSFVQG...LEHTHRRGSLVKR |
| SEQ ID NO: 60 and 82 | MLIIVLLFLATLANS...LDCSGDVFFGYTRGDKTDVHKSQALTAVK NIKR |
| SEQ ID NO: 61 and 83 | MESVSSLFNIFSTIMVNYKSLVLALLSVSNLKYARG...MPTSERQQG LEER |
| SEQ ID NO: 62 | MFAFYFLTACISLKGVFG |
| SEQ ID NO: 63 | MRFSTTLATAATALFFTASQVSA |
| SEQ ID NO: 64 and 84 | MKFAYSLLLPLAGVSA...SVINYKR |

TABLE 1-continued

Sequences of exemplary signal peptides

| | | |
|---|---|---|
| SEQ ID NO: 65 and 85 | MKFFAIAALFAAAAVA...QPLEDR | |
| SEQ ID NO: 66 | MQFFAVALFATSALA | |
| SEQ ID NO: 67 and 86 | MKWVTFISLLFLFSSAYS...RGVFRR | |
| SEQ ID NO: 68 | MRSLLILVLCFLPLAALG | |
| SEQ ID NO: 69 | MKVLILACLVALALA | |
| SEQ ID NO: 70 | MFNLKTILISTLASIAVA | |
| SEQ ID NO: 71 | MYRKLAVISAFLATARAQSA | |

In one aspect, the disclosure provides an expression vector comprising any of the polynucleotides described herein. A polynucleotide may be located in an expression vector. An expression vector may be a construct, which is capable of delivering, and preferably expressing, one or more gene(s) or sequence(s) of interest in a host cell. Examples of expression vectors include, but are not limited to, viral vectors (e.g., adenoviruses, adeno-associated viruses, and retroviruses), naked DNA or RNA expression vectors, plasmids, cosmids, phage vectors, DNA or RNA expression vectors associated with cationic condensing agents, DNA or RNA expression vectors encapsulated in liposomes, and certain eukaryotic cells, such as producer cells. An expression vector may allow easy and efficient replication, cloning, and/or selection.

Accordingly, an expression vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. Expression vector components may generally include, but are not limited to, one or more of the following: a signal sequence; an origin of replication; one or more marker genes; and suitable transcriptional controlling elements (such as promoters, enhancers and terminator). For expression (e.g., translation), one or more translational controlling elements are also usually required, such as ribosome binding sites, translation initiation sites, internal ribosome entry site, and stop codons. The expression vector may be used to transduce, transform or infect a cell, thereby causing the cell to express nucleic acids and/or proteins other than those native to the cell. The expression vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such expression vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining cloning and expression vectors are well-known (see, e.g., Green and Sambrook, Molecular Cloning: A Laboratory Manual, 4th edition, Cold Spring Harbor Laboratory Press, New York (2012)).

An expression vector may further comprise a promoter. Promoters include, but are not limited to, a constitutive promoter, inducible promoter, and hybrid promoter. Promoters include, but are not limited to, acu-5, adhl+, alcohol dehydrogenase (ADH1, ADH2, ADH4), AHSB4m, AINV, alcA, α-amylase, alternative oxidase (AOD), alcohol oxidase I (AOX1), alcohol oxidase 2 (AOX2), AXDH, B2, CaMV, cellobiohydrolase I (cbhl), ccg-1, cDNA1, cellular filament polypeptide (cfp), cpc-2, ctr4+, CUP1, dihydroxyacetone synthase (DAS), enolase (ENO, ENO1), formaldehyde dehydrogenase (FLD1), FMD, formate dehydrogenase (FMDH), G1, G6, GAA, GALL, GAL2, GAL3, GAL4, GAL5, GAL6, GAL7, GAL8, GAL9, GAL10, GCW14, gdhA, gla-1, α-glucoamylase (glaA), glyceraldehyde-3-phosphate dehydrogenase (gpdA, GAP, GAPDH), phosphoglycerate mutase (GPM1), glycerol kinase (GUT1), HSP82, invl+, isocitrate lyase (ICL1), acetohydroxy acid isomeroreductase (ILV5), KAR2, KEX2, β-galactosidase (lac4), LEU2, me1O, MET3, methanol oxidase (MOX), nmtl, NSP, pcbC, PET9, peroxin 8 (PEX8), phosphoglycerate kinase (PGK, PGK1), phol, PHO5, PHO89, phosphatidylinositol synthase (PIS1), PYK1, pyruvate kinase (pkil), RPS7, sorbitol dehydrogenase (SDH), 3-phosphoserine aminotransferase (SERI), SSA4, SV40, TEF, translation elongation factor 1 alpha (TEF1), THI11, homoserine kinase (THR1), tpi, TPS1, triose phosphate isomerase (TPI1), XRP2, and YPT1.

An expression vector may further comprise an auxotrophic marker (e.g., ade1, arg4, his4, ura3, met2). An expression vector may further comprise a selectable marker (e.g., a resistance gene). In some cases, a resistance gene may confer resistance to zeocin, ampicillin, blasticidin, kanamycin, nurseothricin, chloroamphenicol, tetracycline, triclosan, or ganciclovir. An expression vector may comprise a plasmid.

In one aspect, the present disclosure provides a host cell transformed to express one or more heterologous egg white proteins, wherein the host cell is not selected from the group consisting of *Escherichia coli*, *Pichia pastoris*, rice, *Aspergillus niger*, *Aspergillus oryzae*, *Acremonium chrysogenum*, *Saccharomyces cerevisiae*, insect, mice, corn, *Pseudozyma*, tobacco, zebrafish, and any combination thereof.

In one aspect, the present disclosure provides a host cell transformed to express one or more heterologous egg white proteins, wherein the one or more egg white proteins are not selected from the group consisting of ovalbumin, ovotransferrin, lysozyme, ovostatin, ovomucoid, ovoinhibitor, avidin, and any combination thereof.

In one aspect, the present disclosure provides a host cell comprising a polynucleotide or expression vector described herein. Any host cell capable of expressing heterologous DNA can be used for the purpose of isolating a protein or the polynucleotides encoding a protein. Suitable host cells include, but are not limited to, mammalian (e.g., human such as HEK or HeLa; mouse such as a 3T3 or cells derived from Swiss, BALB/c or NIH mice; hamster such as CHO; monkey such as COS), bacterial (e.g., *Escherichia coli, Bacillus subtilis, Pseudomonas, Streptomyces*), fungal (e.g., *Saccharomyces cerevisiae, Schizosaccharomyces pombe, Kluyveromyces lactis*), or insect (e.g., *Drosophila melanogaster*, High Five, *Spodoptera frugipedera* Sf9) host cells. The host cells can be transfected, e.g., by conventional means such as electroporation with at least one expression vector of the disclosure. The expression vectors containing the polynucleotides of interest can be introduced into a host cell by any of a number of appropriate means, including electroporation, chemical transformation, transfection employing calcium chloride, rubidium chloride, calcium phosphate, DEAE-dextran, or other substances; microprojectile bombardment; lipofection; PEG-mediated protoplast fusion; *Agrobacterium tumefaciens*-mediated transformation; biolistic transformation; and infection (e.g., where the vector is an infectious agent such as vaccinia virus). The choice of introducing expression vectors or polynucleotides will often depend on features of the host cell. The transfected or transformed host cell may then be cultured under conditions that allow expression of the protein. In some embodiments, a protein is purified from a host cell.

An expression vector may be genomically integrated. A host cell may comprise multiple copies of an expression vector. In some cases, a host cell may be selected from the group consisting of bacteria, fungi, plant, insect, mammalian, and any combination thereof. In some cases, fungi may be yeast or filamentous fungi. Yeast includes, but is not limited to, *Arxula* spp., *Arxula adeninivorans, Kluyveromyces* spp., *Kluyveromyces lactis, Pichia* spp., *Pichia angusta, Pichia pastoris, Saccharomyces* spp., *Saccharomyces cerevisiae, Schizosaccharomyces* spp., *Schizosaccharomyces pombe, Yarrowia* spp., and *Yarrowia lipolytica*. Fungi include, but are not limited to, *Agaricus* spp., *Agaricus bisporus, Aspergillus* spp., *Aspergillus awamori, Aspergillus fumigatus, Aspergillus nidulans, Aspergillus niger, Aspergillus oryzae, Colletotrichum* spp., *Colletotrichum gloeosporiodes, Endothia* spp., *Endothia parasitica, Fusarium* spp., *Fusarium graminearum, Fusarium solani, Mucor* spp., *Mucor miehei, Mucor pusillus, Myceliophthora* spp., *Myceliophthora thermophila, Neurospora* spp., *Neurospora crassa, Penicillium* spp., *Penicillium camemberti, Penicillium canescens, Penicillium chrysogenum, Penicillium (Talaromyces) emersonii, Penicillium funiculosum, Penicillium purpurogenum, Penicillium roqueforti, Pleurotus* spp., *Pleurotus ostreatus, Rhizomucor* spp., *Rhizomucor miehei, Rhizomucor pusillus, Rhizopus* spp., *Rhizopus arrhizus, Rhizopus oligosporus, Rhizopus oryzae, Trichoderma* spp., *Trichoderma altroviride, Trichoderma reesei*, and *Trichoderma vireus*. In some cases, a host cell may be selected from the group consisting of *Aspergillus oryzae, Bacillus subtilis, Escherichia coli, Myceliophthora thermophila, Neurospora crassa, Pichia pastoris*, and any combination thereof. A host cell may be approved as generally regarded as safe by the U.S. Food and Drug Administration. A host cell may be auxotrophic. A host cell may be glycoengineered, for instance, by having its glycosylation pathways humanized or engineered to more closely resemble another organism (e.g., a bird or chicken).

In one aspect, the present disclosure provides a cell culture comprising a host cell described herein.

In some embodiments, a polypeptide or protein is produced using in vitro or cell-free protein synthesis, for example using a cell-free translation system comprising a cell extract such as *Escherichia coli* cell extract, rabbit reticulocyte cell extract, wheat germ cell extract, or insect cell extract. The expressed protein may be recovered, isolated, and/or optionally purified from the cell, cell extract, or from the culture medium, by appropriate means known to one of skill in the art. For example, the proteins are isolated in soluble form following cell lysis, or extracted using known techniques, e.g., in guanidine chloride. The proteins may be further purified using any of a variety of conventional methods including, but not limited to: liquid chromatography such as normal or reversed phase, using HPLC, FPLC and the like; affinity chromatography such as with inorganic ligands or monoclonal antibodies; size exclusion chromatography; immobilized metal chelate chromatography; gel electrophoresis; and the like. One of skill in the art may select the most appropriate isolation and purification techniques. Still other suitable host cells, as well as methods for transfection, culture, amplification, screening, production, and purification are known in the art.

In one aspect, the present disclosure provides a method for making a consumable product, the method comprising substituting a portion of an egg-based ingredient with an isolated recombinant egg white protein, isolated mutant ovomucoid, or egg white protein composition described herein.

In one aspect, the present disclosure provides a method for making a consumable product, the method comprising adding an isolated recombinant egg white protein, isolated mutant ovomucoid, or egg white protein composition described herein.

In one aspect, the present disclosure provides a method of using a recombinant egg white protein as a processing agent to make a processed consumable product. In some cases, the method further comprises removing the recombinant egg white protein. The recombinant egg white protein may or may not be consumed in the processed consumable product. The processed consumable product may contain trace amounts of the recombinant egg white protein. In some cases, the processed consumable product does not contain the recombinant egg white protein.

In one aspect, the present disclosure provides a method of using an isolated recombinant egg white protein, isolated mutant ovomucoid, or egg white protein composition described herein as a processing agent to make a processed consumable product. In some cases, the method further comprises removing the isolated recombinant egg white protein, isolated mutant ovomucoid, or egg white protein composition. In some cases, the processing agent acts as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a consumable product comprising an isolated recombinant egg white protein, isolated mutant ovomucoid, or egg white protein composition described herein. A consumable product includes, but is not limited to, food product, beverage product, pharmaceutical product, and hygiene product.

In one aspect, the present disclosure provides a method of using a recombinant egg white protein as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a method of using an isolated recombinant egg white protein, isolated mutant ovomucoid, or egg white protein composition described herein as an emulsifier, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, preservative, antimicrobial (e.g., antibacterial, antifungal, antiviral, antiparasitic), food spoilage inhibitor, malolactic fermentation inhibitor, texture improvement agent, egg replacement, or any combination thereof.

In one aspect, the present disclosure provides a method for diagnosing a food allergy, the method comprising introducing an isolated recombinant egg white protein, isolated mutant ovomucoid, or egg white protein composition described herein to a subject. In some cases, the introducing is performed using a skin prick test, blood test, or oral food challenge.

In one aspect, the present disclosure provides a method for treating a food allergy, the method comprising substituting an egg white allergen with an isolated recombinant egg white protein, isolated mutant ovomucoid, or egg white protein composition described herein or increasing a tolerance to an egg white allergen of a subject by consuming an isolated recombinant egg white protein, isolated mutant ovomucoid, or egg white protein composition described herein.

In one aspect, the present disclosure provides a method for inhibiting malolactic fermentation in a consumable product (e.g., wine), the method comprising providing an egg white lysozyme to the consumable product. The egg white lysozyme may be recombinantly expressed.

In one aspect, the present disclosure provides a method for using lysozyme (e.g., egg white lysozyme) as an antimicrobial, antiviral, preservative, or any combination thereof, for instance in food, animal feed, fruits, vegetables, pharmaceuticals, tofu, bean curd, cheese, seafood, meat, wine, sake, or beer (e.g., non-pasteurized beer). In one aspect, the present disclosure provides a method for using lysozyme (e.g., egg white lysozyme) to inhibit growth of a food spoiling organism, inhibit late-blowing (e.g., in cheese), increase shelf life, aid digestibility, treat gastrointestinal diseases, improve food safety, boost the immunity system, replace or reduce sulfites, in skin care, to cure or prevent acne or bed sores, in optical conditions, in dental conditions, in oral conditions, to treat headaches, to treat colds, to treat throat infections, or any combination thereof. The lysozyme may be recombinantly expressed.

In one aspect, the present disclosure provides a method for using ovalbumin (e.g., egg white ovalbumin) as a reference protein for immunization or biochemical studies; as a standard in the investigation of composition, physical properties, and/or structure of proteins; as a blocking agent (e.g., in immunohistochemistry or in western blots); for the detection of anti-hemoglobin monoclonal antibodies (e.g., in enzyme-linked immunosorbent assays (ELISA)); as a protein standard in molecular weight determination (e.g., by SDS-PAGE or size exclusion chromatography); in cell culture systems or in diagnostics to stabilize enzymes and hormones that would otherwise lose their functional integrity; as a protein carrier or stabilizer; or any combination thereof. The ovalbumin may be recombinantly expressed.

In one aspect, the present disclosure provides a method for using ovotransferrin (e.g., egg white ovotransferrin) as an iron-binding protein (e.g., to make iron in a bacterial culture medium nutritionally unavailable to harmful microorganisms, such as *Schigella dysenteriae*); as a culture media ingredient for the maturation of cells; to provide iron to cells; to detoxify culture media (e.g., by binding metal ions, such as zinc, iron, and aluminum); as a preservative; as an antiviral, antibiotic, or antimicrobial; as a lactoferrin substitute; or any combination thereof. The ovotransferrin may be recombinantly expressed.

In one aspect, the present disclosure provides a method for using avidin (e.g., egg white avidin) as a biotin binding agent; in an immunoassay; in histochemistry; in cytochemistry; in biotin purification; in chromosome visualization; in protein purification; in affinity chromatography; in affinity cytochemistry; in the study of cell surface molecular interactions; in signal amplification in immunoassay; in diagnostics; in drug delivery, targeting, or neutralization; in gene mapping; in an avidin-conjugated probe (e.g., enzymes, antigens, antibodies, lectins, hormones, nucleic acids, cells, sub-cellular organelles); or any combination thereof. The avidin may be recombinantly expressed.

In one aspect, the present disclosure provides a method for using an isolated recombinant egg white protein, isolated mutant ovomucoid, or egg white protein composition as a protein supplement. In one aspect, the present disclosure provides a method for using one or more egg white proteins as a protein supplement. In some cases, the protein supplement is formulated as a solid (e.g., powder), liquid, gel, shake, or protein bar.

Egg white protein compositions may be treated, for example, to remove glucose, preserve color, or stabilize compositions for longer storage. Glucose may be removed from a composition for long storage stability. A composition may be clarified, filtered, desugared (e.g., stabilized, glucose-free), spray dried, and/or pasteurized. Pasteurization may occur in a "hot room" maintained at a temperature of at least 130° F. (54° C.) for a minimum of seven to ten days. Pasteurization at a higher temperature may improve gel strength. Salmonella may be eliminated if the moisture content of the composition is kept at approximately 6%. Whipping ability may improve when stored in the hot room at low moisture levels. Pasteurization may occur using high temperature, short-time (HTST) pasteurization equipment. Spray drying may occur before or after pasteurization. A composition may be ultra-pasteurized. Compositions may be clarified, filtered, pasteurized, homogenized, and/or frozen at −10° to −40° F. (−23.3° to −40° C.). Compositions may be a liquid, a refrigerated liquid, frozen, or dried.

Proteins and compositions herein can be added to or mixed with one or more food additives. Food additives can add volume and/or mass to a composition. A food additive may improve functional performance and/or physical characteristics. For example, a food additive may prevent gelation or increased viscosity due to the lipid portion of the lipoproteins in the freeze-thaw cycle. An anticaking agent may be added to make a free-flowing composition. Carbohydrates can be added to increase resistance to heat damage, e.g., less protein denaturation during drying and improve stability and flowability of dried compositions. Whipping additives may be added to dried compositions (e.g., at a level of less than 0.1% by weight of the liquid prior to drying) to improve whipping ability and aeration properties. Food additives include, but are not limited to, food coloring, pH adjuster, natural flavoring, artificial flavoring, flavor enhancer, batch marker, food acid, filler, anticaking agent (e.g., sodium silicoaluminate), antigreening agent (e.g., citric acid), food stabilizer, foam stabilizer or binding agent, antioxidant, acidity regulatory, bulking agent, color retention agent, whipping agent (e.g., ester-type whipping agent, triethyl citrate, sodium lauryl sulfate), emulsifier (e.g., lecithin), humectant, thickener, pharmaceutical excipient, solid diluent, salts, nutrient, sweetener, glazing agent, preservative, vitamins, dietary elements, carbohydrates, polyol, gums, starches, flour, oil, and bran.

Food coloring includes, but is not limited to, FD&C Yellow #5, FD&C Yellow #6, FD&C Red #40, FD&C Red #3, FD&C Blue No. 1, FD&C Blue No. 2, FD&C Green No. 3, carotenoids (e.g., saffron, β-carotene), annatto, betanin, butterfly pea, caramel coloring, chlorophyllin, elderberry juice, lycopene, carmine, pandan, paprika, turmeric, curcuminoids, quinoline yellow, carmoisine, Ponceau 4R, Patent Blue V, and Green S.

pH adjuster includes, but is not limited to, Tris buffer, potassium phosphate, sodium hydroxide, potassium hydroxide, citric acid, sodium citrate, sodium bicarbonate, and hydrochloric acid.

Foam stabilizer or binding agent includes, but is not limited to, kappa carrageenan, iota carrageenan, lambda carrageenan, triethyl citrate, xanthan gum, methyl cellulose, hydroxyethyl cellulose, hydroxymethyl cellulose, and polyacrylimides.

Salts include, but are not limited, to acid salt, alkali salt, organic salt, inorganic salt, phosphates, chloride salts, sodium chloride, potassium chloride, magnesium chloride, magnesium perchlorate, calcium chloride, ammonium chloride, iron chlorides, and zinc chloride.

Nutrient includes, but is not limited to, macronutrient, macronutrient, essential nutrient, non-essential nutrient, dietary fiber, amino acid, essential fatty acids, omega-3 fatty acids, and conjugated linoleic acid.

Sweeteners include, but are not limited to, sugar substitute, artificial sweetener, acesulfame potassium, advantame, alitame, aspartame, sodium cyclamate, dulcin, glucin, neohesperidin dihydrochalcone, neotame, P-4000, saccharin, aspartame-acesulfame salt, sucralose, brazzein, curculin, glycyrrhizin, glycerol, inulin, mogroside, mabinlin, malto-oligosaccharide, mannitol, miraculin, monatin, monellin, osladin, pentadin, stevia, trilobatin, and thaumatin.

Carbohydrates include, but are not limited to, sugar, sucrose, glucose, fructose, galactose, lactose, maltose, mannose, allulose, tagatose, xylose, arabinose, high fructose corn syrup, high maltose corn syrup, corn syrup (e.g., glucose-free corn syrup), monosaccharides, disaccharides, and polysaccharides (e.g., polydextrose, maltodextrin).

Polyols include, but are not limited to, xylitol, maltitol, erythritol, sorbitol, threitol, arabitol, hydrogenated starch hydrolysates, isomalt, lactitol, mannitol, and galactitol (dulcitol).

Gums include, but are not limited to, gum arabic, gellan gum, guar gum, locust bean gum, acacia gum, cellulose gum, and xanthan gum.

Vitamins include, but are not limited to, niacin, riboflavin, pantothenic acid, thiamine, folic acid, vitamin A, vitamin B6, vitamin B12, vitamin D, vitamin E, lutein, zeaxanthin, choline, inositol, and biotin.

Dietary elements include, but are not limited to, calcium, iron, magnesium, phosphorus, potassium, sodium, zinc, copper, manganese, selenium, chlorine, iodine, sulfur, cobalt, molybdenum, and bromine.

A method of making a composition may comprise drying and/or concentrating. In some cases, drying forms a dry, dehydrated, concentrated, and/or solid composition. Some non-limiting examples of drying methods include thermal drying, evaporation (e.g., by means of vacuum or air), distillation, boiling, heating in an oven, vacuum drying, spray drying, freeze drying, lyophilization, and any combination thereof. The mechanism of drying can affect the hydration and molecular structure of the composition to yield different physical properties. The composition can be dried until the composition comprises about or at least about 0.001, 0.005, 0.01, 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 86, 87, 88, 89, 90, 91, 92, 93, 94, 95, or more than 95% solvent (e.g., water) by weight. The composition can be dried until the composition comprises up to about 0.001, 0.005, 0.01, 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 86, 87, 88, 89, 90, 91, 92, 93, 94 or 95% solvent (e.g., water) by weight. For example, a composition can be dried via any standard drying method (e.g., 12-80 hours in an oven at 60° C., using industrial air blowers, etc.) to remove a solvent to form a dry or solid composition. In another example, a composition can be concentrated (e.g., from 80% water to 20% water).

A method of making a composition may comprise diluting and/or hydrating. In some cases, the diluting may comprise addition of a solvent. The composition can be diluted until the composition comprises about or at least about 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 86, 87, 88, 89, 90, 95, 96, 97, 98, 99, 99.5, or 99.9% water by weight. The composition can be diluted until the composition comprises up to about 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 86, 87, 88, 89, 90, 95, 96, 97, 98, 99, 99.5, or 99.9% water by weight. For example, a composition can be diluted (e.g., from 20% water to 80% water). In another example, a dry composition can be hydrated (e.g., from a dry solid to 80% water).

EXAMPLES

Example 1

Recombinant Expression of Egg White Proteins in a Host Cell

A DNA plasmid or DNA oligonucleotide containing a gene sequence encoding an egg white protein is incubated with a restriction enzyme that cleaves the gene sequence at flanking restriction sequence sites. The gene sequence is isolated by agarose gel electrophoresis and gel extraction methods. The purified gene sequence is incubated with DNA ligase, DNA nucleotides as necessary, and an expression plasmid cleaved at restriction sites that leaves ends complementary to those of the isolated gene sequence, to ligate the gene downstream of a promoter (which can confer constitutive expression in a host cell, e.g., the glyceraldehyde-3-phosphate dehydrogenase promoter, or inducible expression dependent on the presence of a substance in the medium that the host cell line grows in) in the expression plasmid.

For example, a plasmid containing the gene sequence for ovalbumin flanked by the EcoRI and Sacll restriction sites respectively in the 5'→3' direction can be cut with EcoRI and SacII restriction enzymes, isolated on an agarose gel, and ligated into a pGAPZ expression vector cut with EcoRI and Sacll.

The ligation reaction is transformed using standard methods (e.g., electroporation) into a competent cell line (e.g., Dh5alpha cell line) and plated on agar plates containing an antibiotic (e.g., Zeocin) to select for colonies of competent cells that have been transformed with the expression vector. After incubating plates for a period of time and at a temperature appropriate for growth of colonies that can be manually selected (e.g., for 16 hours at 37° C.), individual colonies are picked. The expression vector from successful transformants is isolated and purified by standard molecular biological methods (e.g., silica gel membrane or column, phenol chloroform extraction).

The expression vector is transformed into a host cell (e.g., Pichia pastoris) using standard molecular biology methods (e.g., electroporation of an electrocompetent host cell, or transformation of the host cell in the presence of polyethylene glycol or dimethyl sulfoxide). Successful transformants of the host cell by the expression vector can be selected for by spreading a solution of the transformation reaction onto a plated media (e.g., agar plate) whereby the media is appropriate for the growth of the host cell and contains a selection agent (e.g., an antibiotic corresponding to a resistance gene carried on the expression vector). The plated media is incubated for an appropriate amount of time and at an appropriate temperature until individual colonies of the host cell can be isolated from the plate (e.g., 30° C. for one week). The resultant clones are individually isolated and plated separately on fresh selection plates and incubated again. Individual colonies from these plates are used to inoculate individual culture vessels containing appropriate growth medium for the host cell with the same selection agent as used in the initial round. After an appropriate amount of time (e.g., overnight at 30° C. in a shaker flask), successful transformation of the host cell with the expression vector can be determined in each culture vessel by the presence of protein coded by the gene sequence versus a control vessel that is inoculated with a colony from a negative control plate as determined by standard molecular biology methods (e.g., Western blot). Colonies from selection plates corresponding to culture vessels showing protein expression can be used to inoculate vessels containing media appropriate for the host cell to promote growth of the host cell and secretion of the protein into the media. Alternatively, colonies from plates corresponding to culture vessels showing protein expression can be stored for later use (e.g., at −80° C. in a DMSO solution).

Example 2

Choice of a Host Cell and Comparison of Recombinant Proteins to Native Proteins

DNA sequences encoding a protein component of egg white can be synthesized and cloned into an expression vectors for expression in a host cell (e.g., yeast, filamentous fungi).

For example, the yeast strain *Pichia pastoris* may be a suitable a host species for the recombinant vectors, due to its efficiency in recombinant expression and protein secretion, particularly for proteins with disulfide bonds. *Pichia pastoris* is grown in glycerol-containing BMGY media for two days and switched to methanol-containing BMMY media to induce recombinant protein production and grown for two days to a week in a flask with shaking at 30° C.

Recombinant proteins can be compared to native protein, for instance through protein conformation, activity, acetylation pattern, phosphorylation pattern, glycosylation pattern, gelation properties, or other functional properties.

The above scheme is to be optimized in order that protein yields/(L of culture)/day can be increased to achieve optimal output capacity and production cost.

Example 3

Purification of Recombinant Proteins

Purified recombinant proteins can be obtained from cultures of transformed cell lines. The desired yield of the protein (e.g., in grams) can be obtained with appropriate sized fermentation vessels and culturing time. Secreted recombinant proteins can be purified from the culture supernatant (e.g., by spinning down culture media in a centrifuge). For example, host cells are removed from the cell culture supernatant by centrifugation. The proteins in the supernatant are then purified by hollow fiber diafiltration. In a second example, proteins may be purified with a mild salt extraction, followed by centrifugation.

Alternative vessel designs can allow continuous circulation of media, and filtration in a separate vessel to collect protein secretions without interrupting cell growth (e.g., a hollow fiber bioreactor).

Purified recombinant proteins can be dialyzed with an aqueous buffer of appropriate pH that is suitable for gelation upon heating to obtain a wet egg white protein composition or for downstream lyophilization (e.g., spray drying) to obtain a powdered egg white protein composition.

Figure 16:
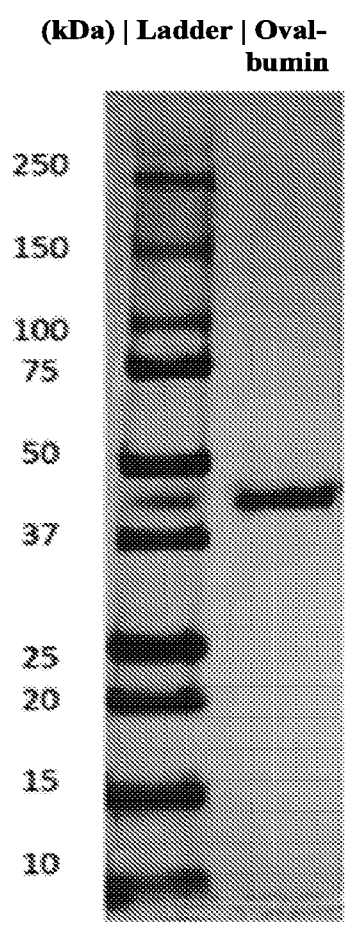
FIG. 16 shows a gel image of recombinant ovalbumin with a protein ladder, in accordance with examples.
Figure 17:
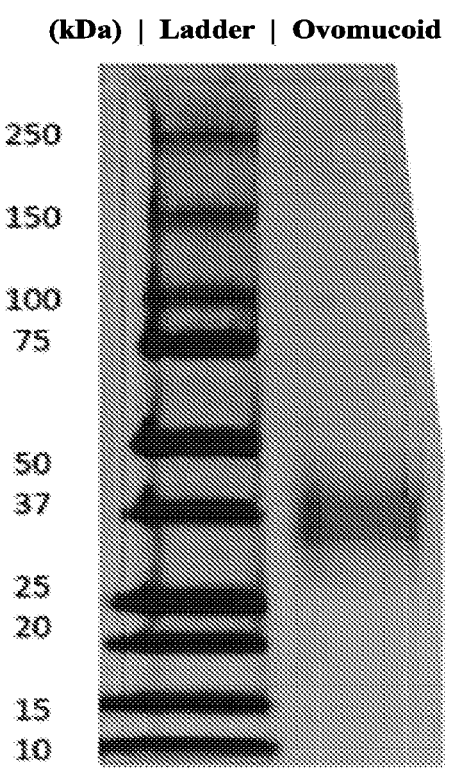
FIG. 17 shows a gel image of recombinant ovomucoid with a protein ladder, in accordance with examples.

Purified recombinant proteins can be characterized by Coomassie stained 4-20% sodium dodecyl sulfate polyacrylamide gel electrophoresis (SDS-PAGE), as shown for example in FIG. 16 and FIG. 17.

Example 4

Combination of Purified Recombinant Proteins Into an Egg White Protein Composition The construction of recombinant vectors and purification of their protein products in a transformed cell line can be carried out separately for each egg white protein constituent that is to be included in the final formulation for the egg white protein composition. Desired combinations and amounts of these purified proteins in the composition can be added into one volume to achieve specific final concentrations of each protein. For example, one formulation could include constituent recombinant proteins added together in final concentrations that match their corresponding concentration in animal derived egg whites.

An egg white protein composition can be stored and refrigerated as a wet egg white protein composition. Alternatively, an egg white protein composition may first be heated to induce gelation (e.g., at a temperature sufficient to induce denaturation of the most unstable constituent protein), and then stored as a refrigerated product or lyophilized for a powdered egg white protein composition. Alternatively, egg white proteins may be combined in lyophilized form to form an egg white protein composition and then dissolved in solution. The concentration and components of salts and food additives in the solution may vary depending on formulation.

Varying amounts of protein components can be mixed together in proportions matching those found in animal derived egg whites, and spray dried to be packaged as dried egg white protein, which can be reconstituted with the addition of water. Alternatively, the egg protein mix can be subjected to heating, and consequent gelation of the substance can be packaged as a refrigerated ready-made egg white. Factors such as protein mix composition, pH, percentage of water, rate of heating can be varied to produce variations in consistency and palatability.

Example 5

Isolation of Egg White From an Egg

An egg is brought to room temperature (e.g., 25° C.) by leaving the uncracked egg outside for at least 30 minutes. The egg white is separated from the yolk.

Example 6

Foaming and Foam Stability of Whipped Egg White or Egg White Protein Composition Egg white or egg white protein composition (10 mL) is added to a 50 mL Pyrex beaker. The beaker is placed on a Dremel rotary tool work station stand with a Dremel 3000 variable speed rotary tool mounted to it with a 0.5 inch steel brush attachment. The stand is adjusted such that when the Dremel is lowered into the beaker, the brush barely touches the bottom of the beaker and is fully submerged in the egg white. From this submerged starting position, the Dremel tool is turned on to speed setting 3. The steel brush whips the egg white for 1 minute. After 1 minute, the Dremel tool is turned off, the attachment is raised, and the beaker is removed.

Using calipers with at least 0.5 mm accuracy, the foam height is measured as the distance from the liquid-foam interface to the foam-air interface. If no liquid is visible, the foam height is measured as the distanced from the base of the beaker to the top of the foam-air interface.

To measure seeping and/or foam stability, the amount of liquid is measured 10 minutes after shutting off the Dremel tool using the calipers as the distance from the base of the beaker to the liquid-foam interface. The amount of liquid is measured again 30 minutes after shutting off the Dremel tool.

The foam height of the whipped egg white is approximately 30 mm.

The foam height of the whipped egg white protein composition may be approximately 36.25 mm.

The foam seep of the whipped egg white is approximately 2.5 mm after 10 min and 8 mm after 30 min.

The foam seep of the whipped egg white protein composition may be approximately 0 mm after 10 min and 0.5 mm after 30 min.

Example 7

Foam Strength and Texture Analysis of Whipped Egg White or Egg White Protein Composition A recrystallization dish is filled with at least 40 mm of whipped egg white foam or whipped egg white protein composition foam. A trigger value of 3 g is set along with a deformation of 20 mm using a Brookfield TA-MP probe on a Brookfield CT3 Texture Analyzer. The zero height is set to be less than 5 mm above the surface of the egg white foam or egg white protein composition foam. Testing is performed on the Normal setting at least in triplicate and immediately after whipping egg white or egg white protein composition. The whipped egg white or whipped egg white protein composition is tested within 30 minutes of whipping to minimize error due to seepage. Different surface areas of the foam are chosen between tests that are not previously tested so that any collapsed foam bubbles from previous testing do not introduce error in subsequent tests. The initial noise prior to the trigger value is taken into account for error measurements. The difference in peak load between the 3 runs performed per sample is also recorded.

Figure 18:
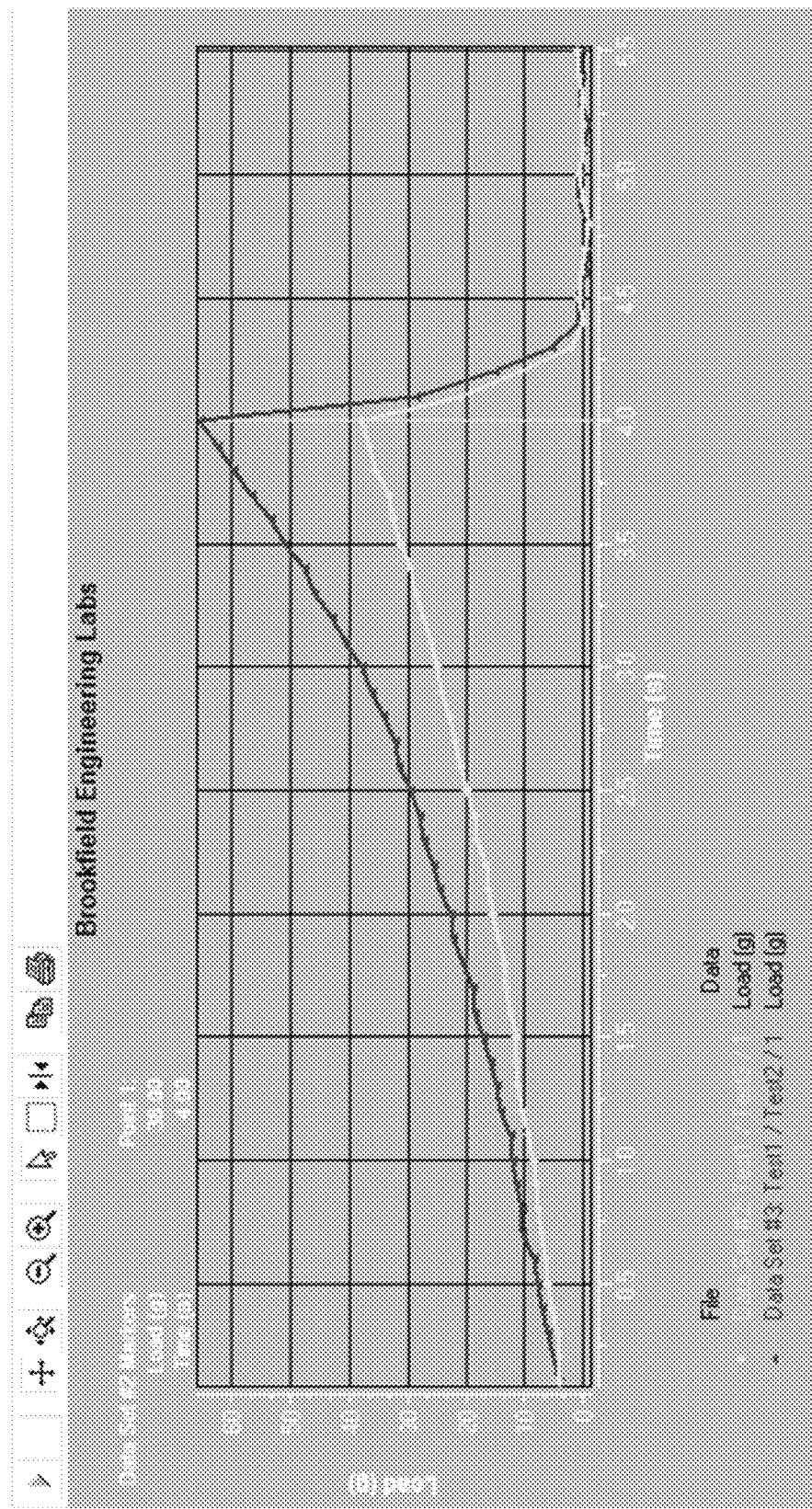
FIG. 18 shows a schematic diagram of foam strength of an egg white protein composition and an egg white, in accordance with examples.

The foam strength of the whipped egg white is approximately 38 g, as shown for example in FIG. 18.

The foam strength of the whipped egg white protein composition is approximately 62 g, as shown for example in FIG. 18.

Example 8

Gel Strength of Cooked Egg White or Egg White Protein Composition

Egg white or egg white protein composition (10 mL) is added to a 50 mL conical falcon tube. The tube is boiled in a water bath at 95° C. for 9 minutes. The tube is removed and allowed to cool to room temperature. The tube is placed in a tube holder on a Brookfield CT3 Texture Analyzer and a Brookfield TA-10 probe is lowered to ~2 mm above the surface of the cooked egg white or egg white protein composition. The analyzer is run with a trigger value of 3 g and a deformation of 2 mm. The gel strength of the cooked egg white or egg white protein composition is measured as the peak hardness seen over the 2 mm deformation on the first run.

The gel strength of the cooked egg white is approximately 500 to 700 g.

The gel strength of the cooked egg white protein composition is approximately 150 to 500 g.

Example 9

Emulsifying Capacity and Emulsion Stability of Egg White or Egg White Protein Composition To evaluate the emulsifying capacity, oil is added gradually to a solution containing egg white or egg white protein composition. The amount of oil required for transition from an oil in water to a water in oil emulsion is determined.

To evaluate the stability of the emulsion, the amount of oil or water separated from the emulsion is determined after leaving the emulsion under certain conditions.

Example 10

Angel Food Cake With Egg White or Egg White Protein Composition

Egg white or egg white protein composition (30 g) is brought to room temperature and placed in the mixing bowl of a KitchenAid stand mixer with a whipping attachment. The egg white or egg white protein composition is beaten on speed 5 until soft peaks form. Finely granulated sugar (18 g)

is slowly added. The mixture is beaten on speed 8 until stiff peaks form. In a separate bowl, sugar (18 g) and flour (24 g) are sifted together. The sugar and flour mixture is folded into the mixture on speed 2. The batter is spooned into a round angel food cake pan and baked in a preheated oven at 200° F. for 30 minutes. After the pan is removed from the oven, it is immediately inverted and allowed to cool before the cake is removed from the pan.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An animal-free egg white composition comprising recombinantly-produced proteins wherein the recombinant-proteins are ovalbumin, ovotransferrin, and lysozyme;
   wherein the animal-free egg white composition comprising recombinantly-produced proteins resembles an animal-derived egg white in consistency, taste, and appearance.

2. An egg white composition, wherein the egg white composition is an animal-free egg-white composition, wherein the animal free-egg white composition comprises a protein content, wherein the protein content consists of recombinant egg white proteins, wherein the recombinant egg white proteins in the animal-free egg white composition consists of:
   a) recombinant ovalbumin;
   b) recombinant ovomucoid;
   c) recombinant lysozyme; and
   d) recombinant ovotransferrin;
   wherein
      a conformation of the recombinant ovalbumin is similar to native ovalbumin,
      a conformation of the recombinant ovomucoid is similar to native ovomucoid,
      a conformation of the recombinant lysozyme is similar to native lysozyme and
      a conformation of the recombinant ovotransferrin is similar to native ovotransferrin;
   wherein
      the proportion of recombinant ovalbumin in the animal-free egg white composition is similar to the proportion of ovalbumin in an animal-derived egg white,
      the proportion of recombinant ovomucoid in the animal-free egg white composition is similar to the proportion of ovomucoid in an animal-derived egg white,
      the proportion of recombinant lysozyme in the animal-free egg white composition is similar to the proportion of lysozyme in an animal-derived egg white, and
      the proportion of recombinant ovotransferrin in the animal-free egg white composition is similar to the proportion of ovotransferrin in an animal-derived egg white;
   and wherein
      the animal-free egg white composition comprising recombinantly-produced proteins resembles an animal-derived egg white in consistency, taste, and appearance.

3. The animal-free egg white composition of claim 1, wherein the dry weight proportion of the recombinantly-produced proteins is substantially similar to their dry weight proportion in an animal-derived egg white.

4. The egg white composition of claim 2, wherein the dry weight proportion of the recombinant proteins is about 54 ovalbumin: 12 ovotransferrin: 11 ovomucoid: 3.4 lysozyme.

5. The egg white composition of claim 2, wherein the protein content consists of about 54% ovalbumin, about 12% ovotransferrin, about 11% ovomucoid and about 3.4% lysozyme.

6. The animal-free egg white composition of claim 1, wherein the composition is dried.

7. The animal-free egg white composition of claim 6, wherein the composition is spray-dried.

8. The animal-free egg white composition of claim 1, wherein the composition is heat-treated.

9. The animal-free egg white composition of claim 1, wherein the composition is gelled.

10. The animal-free egg white composition of claim 1, wherein the recombinantly-produced proteins are produced in a yeast cell.

11. The animal-free egg white composition of claim 10, wherein the yeast cell is a *Pichia pastoris* cell.

12. The animal-free egg white composition of claim 1, wherein the recombinantly-produced proteins are secreted from a *Pichia pastoris* cell.

13. The animal-free egg white composition of claim 1, wherein the composition is packaged as a ready-made egg white.

14. The egg white composition of claim 2, wherein the allergenicity of the egg-white composition is reduced as compared to an animal-derived egg white.

15. The egg-white composition of claim 2, wherein the glycosylation pattern of one or more recombinant proteins is different from animal-derived proteins.

16. A method of producing an animal-free egg white composition comprising:
   a) recombinantly expressing ovalbumin in one or more host cells, wherein the one or more host cells comprise a yeast expression system;
   b) collecting secreted ovalbumin from the one or more host cells;
   c) purifying the recombinantly expressed and collected ovalbumin secreted by the one or more host cells;
   d) recombinantly expressing ovomucoid in one or more host cells, wherein the one or more host cells comprise a yeast expression system;
   e) collecting secreted ovomucoid from the one or more host cells;
   f) purifying the recombinantly expressed and collected ovomucoid secreted by the one or more host cells;
   g) recombinantly expressing lysozyme in one or more host cells, wherein the one or more host cells comprise a yeast expression system;
   h) collecting secreted lysozyme from the one or more host cells;
   i) purifying the recombinantly expressed and collected lysozyme secreted by the one or more host cells;
   j) recombinantly expressing ovotransferrin in one or more host cells, wherein the one or more host cells comprise a yeast expression system;
   k) collecting secreted ovotransferrin from the one or more host cells;
   l) purifying the recombinantly expressed and collected ovotransferrin secreted by the one or more host cells; and
   m) combining the purified ovalbumin, the purified ovomucoid, the purified lysozyme, and the purified ovotransferrin to form an animal-free egg white composition in amounts such that a dry weight proportion of the purified ovalbumin, the purified ovomucoid, the purified lysozyme, and the purified ovotransferrin is substantially similar to the dry weight proportion of, respectively, ovalbumin, ovomucoid, lysozyme, and ovotransferrin in an animal-derived egg white;

wherein the protein content of the animal-free egg white composition consists of the purified ovalbumin, the purified ovomucoid, the purified lysozyme and the purified ovotransferrin; and wherein the animal-free egg white composition is formulated as a refrigerated wet-egg white formulation, a powdered egg white product, or a refrigerated gel-egg white formulation, wherein the animal-free egg white composition comprising recombinantly-produced proteins resembles an animal-derived egg white in consistency, taste, and appearance.

17. The animal-free egg white composition of claim 1, wherein a glycosylation pattern of the recombinantly-produced ovalbumin, ovotransferrin, and lysozyme is different, respectively, from animal-derived ovalbumin, ovotransferrin, and lysozyme.

18. The egg white composition of claim 2, wherein the animal-free egg white composition is spray-dried.

\* \* \* \* \*